(12) United States Patent
Curran

(10) Patent No.: US 9,972,489 B2
(45) Date of Patent: May 15, 2018

(54) COMPOSITION AND METHOD FOR MAKING PICOCRYSTALLINE ARTIFICIAL BORANE ATOMS

(71) Applicant: SemiNuclear, Inc., Plano, TX (US)

(72) Inventor: Patrick Curran, Dallas, TX (US)

(73) Assignee: SemiNuclear, Inc., Plano, TX (US)

( * ) Notice: Subject to any disclaimer, the term of this patent is extended or adjusted under 35 U.S.C. 154(b) by 0 days. days.

(21) Appl. No.: 15/363,230

(22) Filed: Nov. 29, 2016

(65) Prior Publication Data

US 2017/0076942 A1     Mar. 16, 2017

Related U.S. Application Data

(63) Continuation-in-part of application No. 15/167,672, filed on May 27, 2016.
(Continued)

(51) Int. Cl.
*C23C 16/54*     (2006.01)
*C23C 16/46*     (2006.01)
(Continued)

(52) U.S. Cl.
CPC .......... *H01L 21/02521* (2013.01); *C07F 7/21* (2013.01); *C23C 16/30* (2013.01);
(Continued)

(58) Field of Classification Search
CPC ........... H01B 1/06; C23C 16/30; C23C 16/38; C23C 16/40; C23C 16/401; C07F 7/21;
(Continued)

(56) References Cited

U.S. PATENT DOCUMENTS 3,455,745 A   7/1969   Kern et al.
3,607,367 A   9/1971   McCandless et al.
(Continued)

FOREIGN PATENT DOCUMENTS

CN          101074478          5/2016

OTHER PUBLICATIONS

Kiran Shrestha "Electrical Conduction Mechanisms in the disordered material system p-type hydrogenated amorphous silicon", Dec. 2014, 90 pages.
(Continued)

*Primary Examiner* — Jonathan C Langman
(74) *Attorney, Agent, or Firm* — Locke Lord LLP

(57) ABSTRACT

Materials containing picocrystalline quantum dots that form artificial atoms are disclosed. The picocrystalline quantum dots (in the form of boron icosahedra with a nearly-symmetrical nuclear configuration) can replace corner silicon atoms in a structure that demonstrates both short range and long-range order as determined by x-ray diffraction of actual samples. A novel class of boron-rich compositions that self-assemble from boron, silicon, hydrogen and, optionally, oxygen is also disclosed. The preferred stoichiometric range for the compositions is $(B_{12}H_w)_x Si_y O_z$ with $3 \leq w \leq 5$, $2 \leq x \leq 4$, $2 \leq y \leq 5$ and $0 \leq z \leq 3$. By varying oxygen content and the presence or absence of a significant impurity such as gold, unique electrical devices can be constructed that improve upon and are compatible with current semiconductor technology.

27 Claims, 84 Drawing Sheets

Related U.S. Application Data

(60) Provisional application No. 62/167,418, filed on May 28, 2015.

(51) Int. Cl.
| | |
|---|---|
| H01L 21/02 | (2006.01) |
| C30B 7/10 | (2006.01) |
| C23C 16/38 | (2006.01) |
| C23C 16/40 | (2006.01) |
| C30B 29/40 | (2006.01) |
| C07F 7/21 | (2006.01) |
| C23C 16/30 | (2006.01) |
| H01B 1/06 | (2006.01) |

(52) U.S. Cl.
CPC .............. *C23C 16/38* (2013.01); *C23C 16/40* (2013.01); *C23C 16/401* (2013.01); *C30B 7/105* (2013.01); *C30B 29/406* (2013.01); *H01B 1/06* (2013.01); *H01L 21/0245* (2013.01); *H01L 21/0259* (2013.01); *H01L 21/0262* (2013.01); *H01L 21/02208* (2013.01); *H01L 21/02381* (2013.01); *H01L 21/02488* (2013.01); *H01L 21/02491* (2013.01); *H01L 21/02505* (2013.01); *H01L 21/02565* (2013.01); *H01L 21/02579* (2013.01); *H01L 21/02581* (2013.01); *H01L 21/02595* (2013.01)

(58) Field of Classification Search
CPC ... C07F 5/022; C30B 7/105; H01L 21/02579; H01L 21/02208; H01L 21/02211
See application file for complete search history.

(56) References Cited

U.S. PATENT DOCUMENTS

| | | | |
|---|---|---|---|
| 4,818,625 A | 4/1989 | Lavendel et al. | |
| 5,126,284 A | 6/1992 | Curran | |
| 5,272,237 A | 12/1993 | Keller et al. | |
| 5,598,025 A | 1/1997 | Murakoshi et al. | |
| 6,479,919 B1 | 11/2002 | Aselage et al. | |
| 6,517,808 B1 | 2/2003 | Hawthorne et al. | |
| 2001/0035206 A1 | 11/2001 | Inamasu et al. | |
| 2004/0005768 A1 | 1/2004 | Hersee et al. | |
| 2009/0025556 A1 | 1/2009 | Mirkin et al. | |
| 2010/0047952 A1 | 2/2010 | Ohnuma et al. | |
| 2010/0163873 A1 | 7/2010 | Cho et al. | |
| 2010/0233633 A1 | 9/2010 | Nguyen et al. | |
| 2011/0260047 A1 | 10/2011 | Lee | |
| 2012/0043483 A1 | 2/2012 | Bowen et al. | |
| 2015/0099078 A1 | 4/2015 | Fish | |
| 2016/0318810 A1 | 11/2016 | Goswami et al. | |

OTHER PUBLICATIONS

Machine English translation of the description of CN101074478 to Ping et al., retrieved from the ESpacenet website. Internet retrieval date of Jan. 24, 2018.
Wesemann et al., "Silaborates with an Unprecedented Cluster Geometry", Organometallics 1999, vol. 18, pp. 4654-4659.
Ohishi et al. "Synthesis and formation mechanism of hydrogenated boron clusters B12Hn with controlled hydrogen content", The Journal of Chemical Physics, vol. 133, 2010, pp. 074305-1 to 074305-7.
Grundkoette-Stock, Berhhard; Bezugly, Viktor; Kunstmann, Jens; Cuniberti, Gianaurelio; Frauenheim, Thomas; Niehaus, Thomas A.; "SCC-DFTB parametrization for Boron and Boranes", JCTC, Feb. 1, 2012, pp. 1153-1163, American Chemical Society.
Wang, Liaoyuan; "Electronic Structure of Elemental Boron", Thesis, 2010, pp. 1-62, U of MO, Kansas City, MO.
Longuet-Higgins, H.C., Roberts, M. De V.; "The Electric Structure of an Icosahedron of Boron Atoms", Article, Feb. 16, 1995, pp. 110-119, The Royal Society, www.jstor.org.
Emin, David; "Unusual Properties of Icosahedral Boron-Rich Solids", Journal of Solid State Chemistry 179, Feb. 8, 2006, pp. 2791-2798, Elsevier.
Werheit, Helmut; Filipov, Volodymyr; Kuhlmann, Udo; Schwarz, Ulrich; Armbruester, Marc; Leithe-Jasper, Andreas; Tanaka, Takaho; Higashi, Iwami; Lundstroem, Torsten; Gurin, Vladimir N.; and Korsukova, Maria M.; "Raman Effect in Icosahedral Boron-Rich Solids", Sci. Technol. Adv. Mater., 2010, pp. 1-28, (http://iopscience.iop.org/1468-6996/11/2/023001).
Sadrzadeh, Arta; Yakobson, Boris I.; "The Boron Fullerenes"; Handbook of Nanophysics: Clusters and Fullerenes; 2009, pp. 47-1-47-9, Rice University, US.
Jones Otten, Carolyn; Lourie, Oleg R.; Yu, Min-Fend; Cowley, John M.; Dyer, Mark J.; Ruoff, Rodney S.; Buhro, William E.; "Crystalline Boron Nanowires", J. Am. Chem. Soc., 2002, pp. 4564-4565 and 1-10, JACS Communications, WWW.
Kirihara, Kazuhiro; Sasaki, Takeshi; Koshizaki, Naoto; Kimura, Kaoru; "Seebeck Coefficient and Power Factor of Single-Crystalline Boron Nanobelts", Applied Physics Express, 2011, pp. xxxxxx-1-xxxxxx-3, The Japan Society of Applied Physics.
Weber, W.; Thorpe, M.F.; "Vibrations in Icosahedral Boron Molecules and in Elemental Boron Solids", J. Phys. Chem. Solids, 1975, pp. 967-974, Great Britain.
Werheit, Helmut; "Present Knowledge of Electronic Properties and Charge Transport of Icosahedral Boron-Rich Solids" 16th International Symposium on Boron, Borides and Related Materials, Journal of Physics: Conference Series 176, 2009, pp. 1-11, IOP Publishing Ltd.
Howard, Iris A.; Beckel, Charles L.; "Analysis of Boron Carbides' Electronic Structure", NASA subcontract, Aug. 18, 1986, pp. 1-29, New Mexico, US.
Beckel, Charles L., Vaughan, James P.; "Vibrations of Regular Boron Icosahedra", AIP Conference Proceedings 140, 1986, pp. 305-311, AIP Publishing, New Mexico, US.
Parkhomenko et al., Deposition of Au Thin Films and Nanoparticles by MOCVD, Chem. Vap. Deposition, 2012; 18(10-12):336-342 (doi: 10.1002/cvde.201207004) p. 336, col. 1, para 1-2; p. 337, col. 1, para 1; p. 337, col. 1, para 3-col. 2, para 1; ; p. 337, Fig. 1 p. 338, col. 1, para 1; p. 338, Table 2.
Barron, Chemical Vapor Deposition of Silica Thin Films, OpenStax-CXX module; m24897, Jan. 22, 2010 (Jan. 22, 2010) (http://cte-cnx-dev.cnx.org/contents/jhbhyKow@4/Chemical-Vapor-Deposition-of-S) p. 9, para 1.
Aselage, The Coexistence of Silicon Borides with Boron-Saturated Silicon: Metastability of SiB3, Journal of Materials Research, 1998; 13(7): 1786-1794 (doi: 10.1557/JMR.1998.0252) p. 1786, col. 2, para 4-p. 1787, col. 1, para 1.
Kuchumov et al., Monitoring the Microstructure of Nanosized Palladium Layers Obtained via Thermal and VUV Stimulated MOCVD, Surface and Coatings Technology, 2013; 230:266-272 (doi: 10.1016/j.surfcoat.2013.06.049) p. 267, col. 1, para 4.

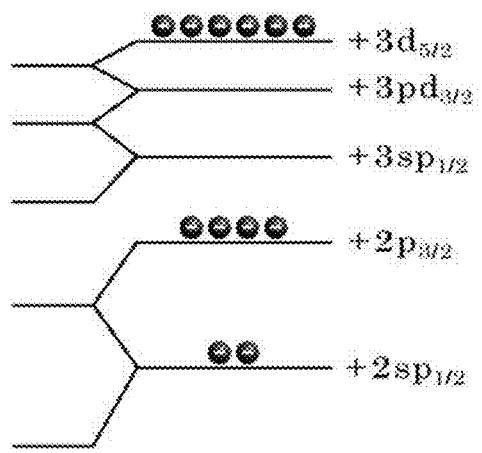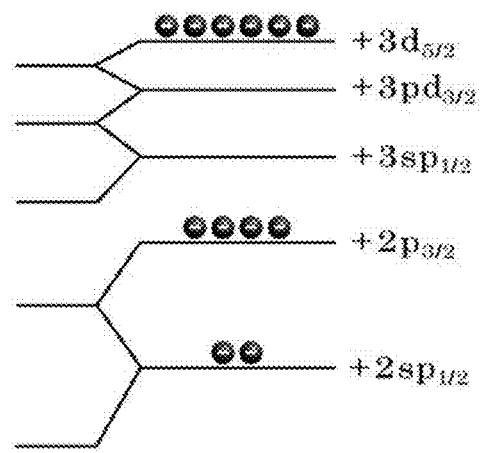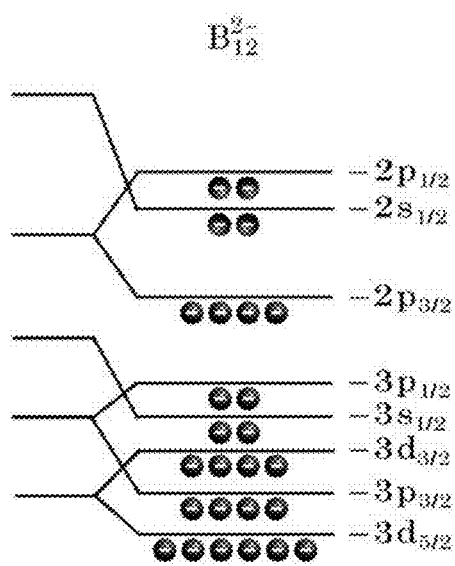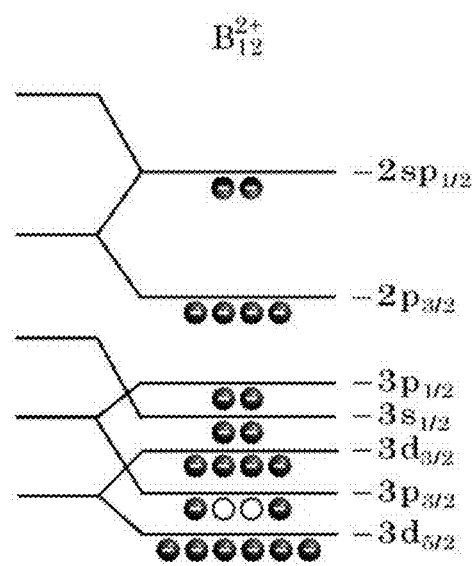
FIG. 62A        FIG. 62B

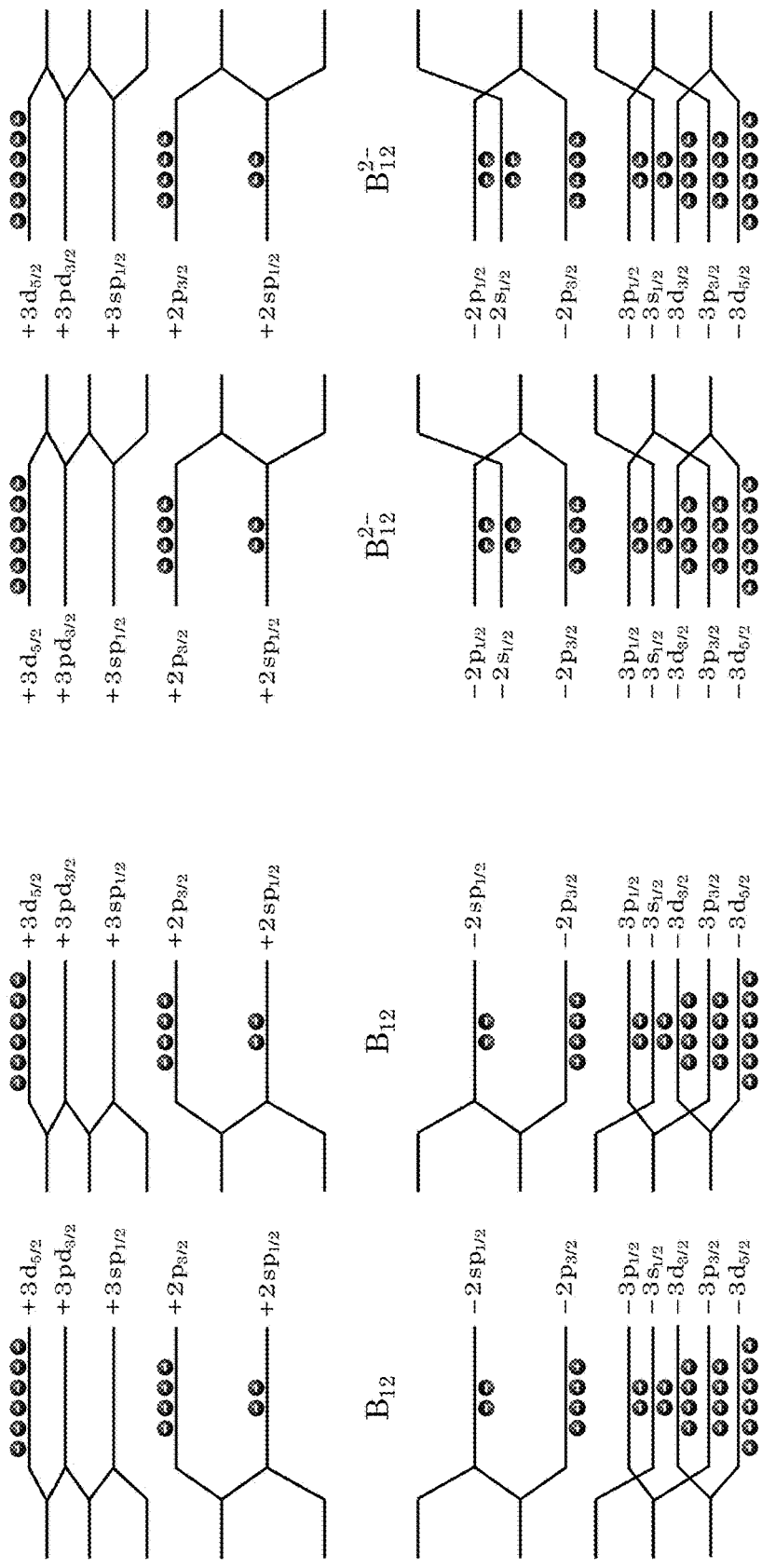
FIG. 75A  $(B_{12}H_4)_3Si_5$
FIG. 75B  $(B_{12}H_4)_3Si_5$
FIG. 75C  $(B_{12}^{2-}H_4)_2Si_4O_2^{2+}$
FIG. 75D  $(B_{12}^{2-}H_4)_2Si_4O_2^{2+}$

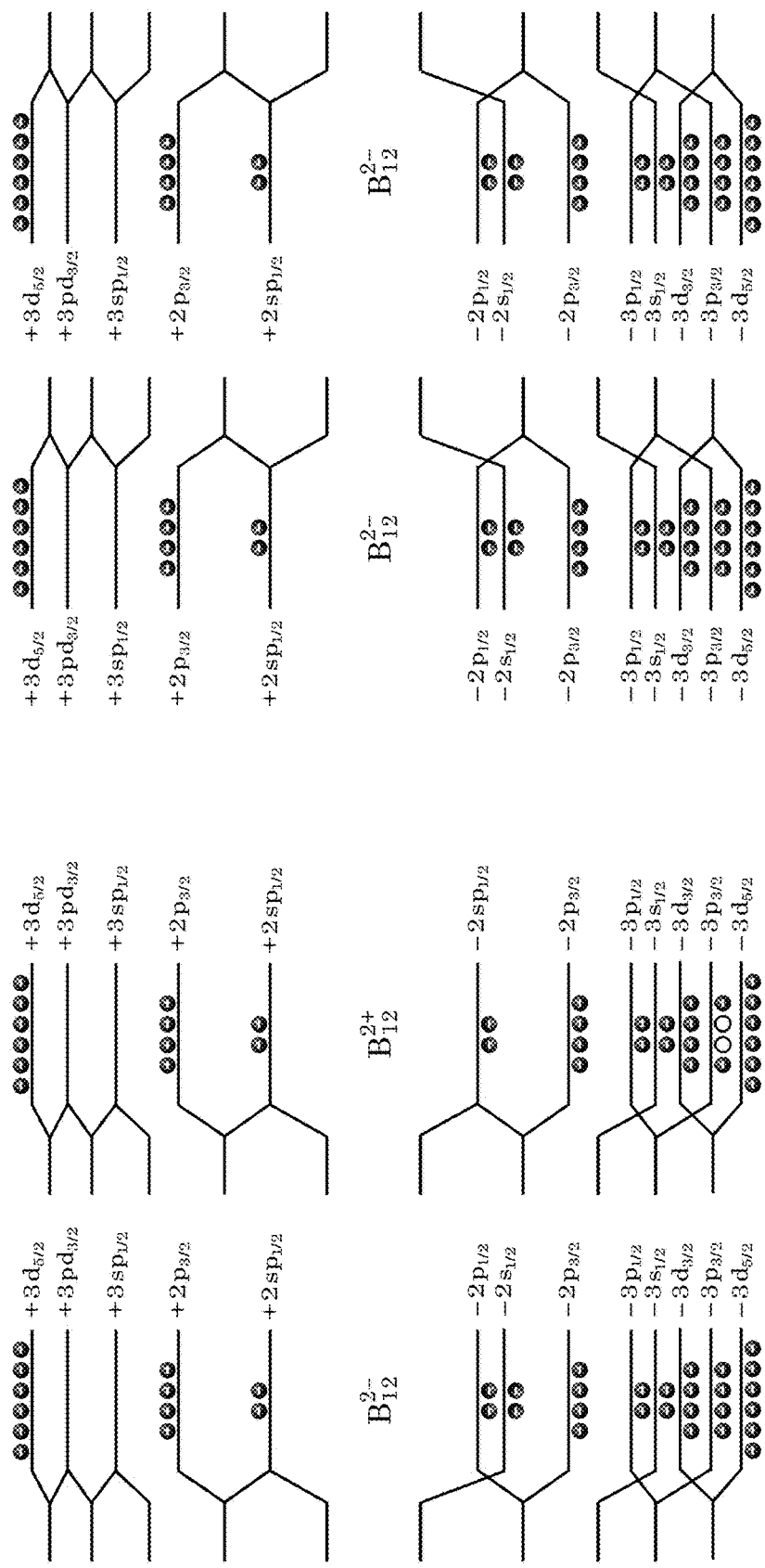
FIG. 76A  $(B_{12}H_4)_2(B_{12}^{2-}H_4)_1Si_5$
FIG. 76B  $(B_{12}H_4)_2(B_{12}^{2+}H_4)_1Si_5$
FIG. 76C  $(B_{12}^{2-}H_4)_2Si_4O_2^{2+}$
FIG. 76D  $(B_{12}^{2-}H_4)_2Si_4O_2^{2+}$

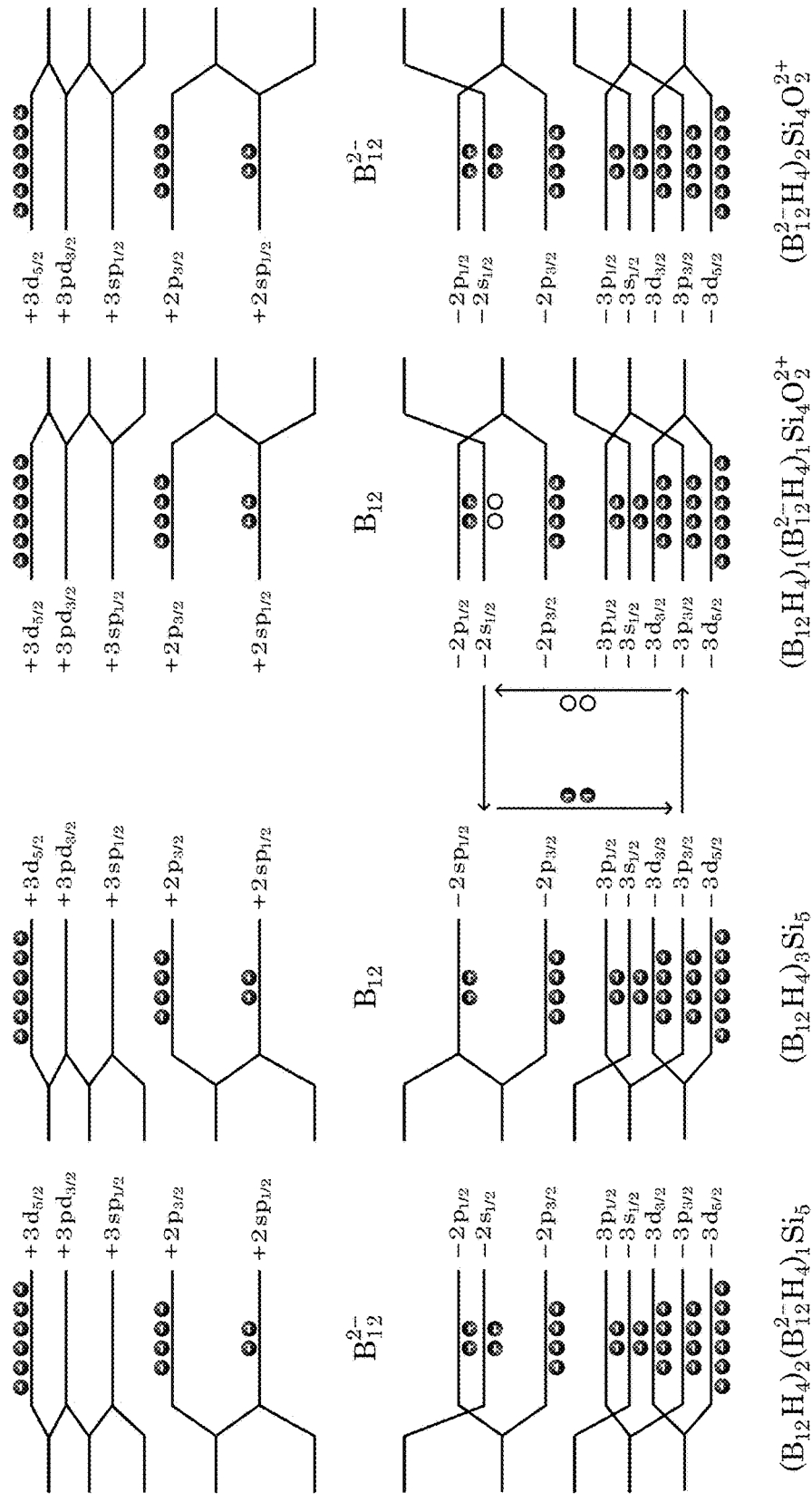
FIG. 78A  $(B_{12}H_4)_2(B_{12}^{2-}H_4)_1Si_5$
FIG. 78B  $(B_{12}H_4)_3Si_5$
FIG. 78C  $(B_{12}H_4)_1(B_{12}^{2-}H_4)_1Si_4O_2^{2+}$
FIG. 78D  $(B_{12}^{2-}H_4)_2Si_4O_2^{2+}$

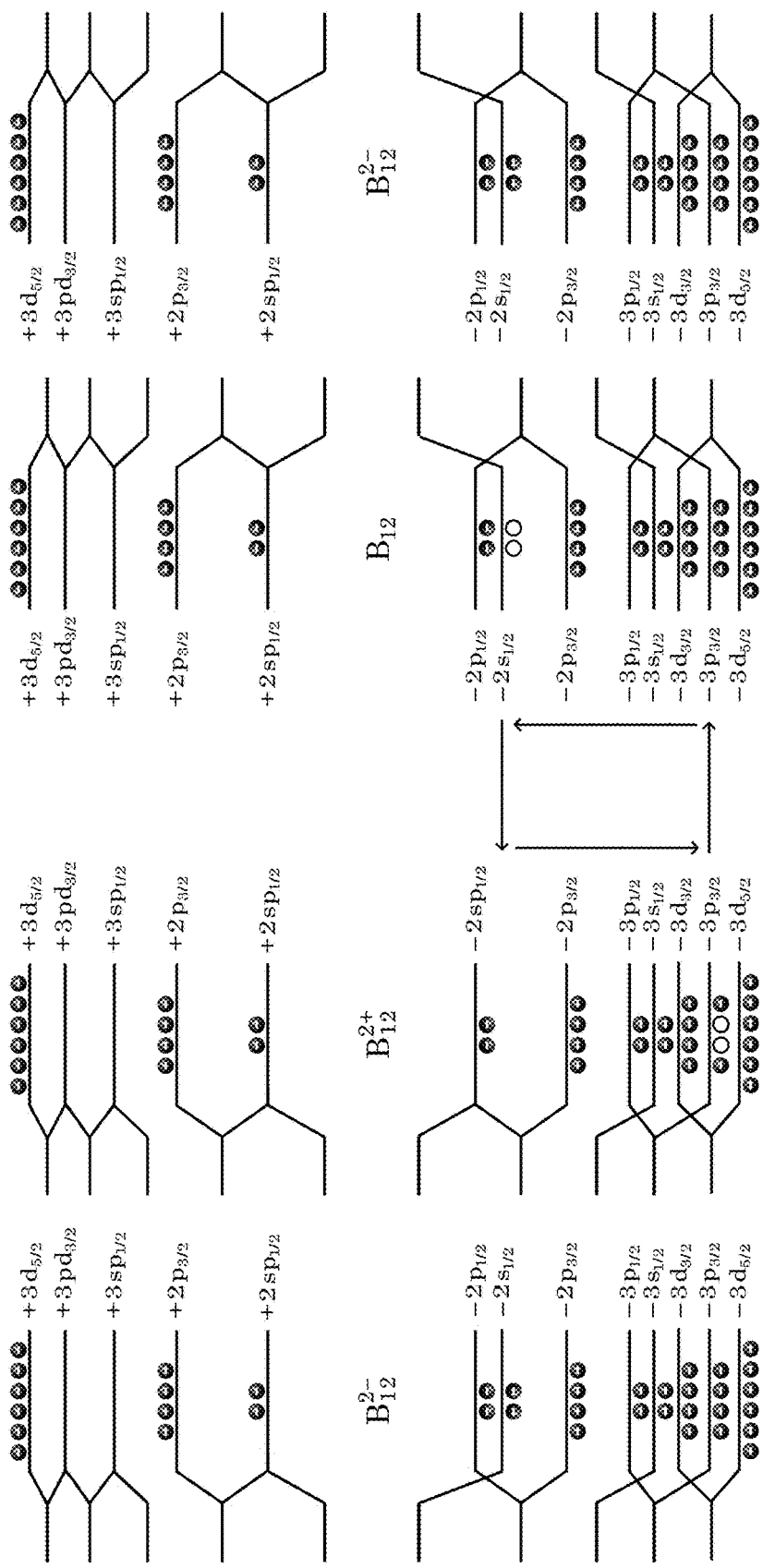

COMPOSITION AND METHOD FOR MAKING PICOCRYSTALLINE ARTIFICIAL BORANE ATOMS

CLAIM OF PRIORITY

This application claims priority to U.S. Provisional Application No. 62/167,418, entitled "Self-Assembled Supramolecular Oxysilaborane and Method for Making Same," filed on May 28, 2015; and U.S. patent application Ser. No. 15/167,672, entitled "Composition and Method for Making Picocrystalline Artificial Atoms", filed on May 27, 2016, the disclosures of which are hereby incorporated by reference.

FIELD OF THE INVENTION

This invention relates to an icosahedral boron-rich composition of matter and, more particularly, to a self-assembled picocrystalline oxysilaborane composition of matter. It further pertains to a method of making such composition.

BACKGROUND OF THE INVENTION

As discussed by Becker et al., in a paper "Boron, The New Graphene?" in *Vacuum Technology & Coating*, April 2015, pp. 38-44, boron supports a unique and mysterious chemistry that has greatly perplexed scientists for many years in the pursuit of useful commercial applications that continue to defy a full chemical understanding. As further discussed in this article, there is an increasing belief by many scientists that new boron compounds could possibly exist in allotropes or polymorphs similar to, and superior to, the recently discovered carbon allotropes comprising fullerenes, carbon nanotubes, and graphene.

Boron is a light electron-deficient element with a small interatomic space between natural boron atoms supporting one shared molecular bonding orbital and two shared molecular antibonding orbitals amongst three boron atoms. As the result of this property, boron atoms tend to form three-center chemical bonds such that two valence electrons bond three boron atoms, with the peak electron density being in the center of the triangle comprised by three boron atoms. This type of chemical bond is very different from a two-center chemical bond in which the peak electron density exists along the rectilinear axis joining two valence electrons. Although boron is a Group-III element, it does not chemically act like other Group-III elements. Boron acts like a nonmetal and forms an extended series of hydrides.

Due to three-center bonds, boron tends to form polyhedral molecules comprising triangular faces. The highest-order symmetrical regular polyhedron formed by triangular faces is an icosahedron with twenty equilateral triangular faces that are interconnected by thirty edges so as to result in twelve vertices. Each vertex of a boron icosahedron is occupied by a boron atom with three valence electrons, such that conventional two-center chemical bonds cannot exist along the 30 icosahedral edges. In a boron icosahedron, the coordination number exceeds the number of boron valence electrons so as to result an electron deficiency. Similar to buckminsterfullerene $C_{60}$, boron icosahedra can potentially form a cage-like molecule, but, boron icosahedra, because they are formed by only triangular faces, can display a higher symmetry than the truncated icosahedral buckminsterfullerene molecule formed by 20 hexagonal faces and 12 pentagonal faces.

In a key landmark paper, "The Electronic Structure of an Icosahedron of Boron," *Proceedings of the Royal Society,* A230, 1955, p. 110, Longuet-Higgins and Roberts developed the molecular bonding conditions of a closed-shell boron icosahedron exhibiting an icosahedral symmetry $I_h$ with a boron nucleus at each vertex. Longuet-Higgins and Roberts obtained the 48 molecular orbitals of a boron icosahedron by the linear combination of 48 nonorthogonal atomic orbitals that are related to 48 symmetry orbitals in terms of the irreducible representations of the regular icosahedral group $I_h$ comprising the nondegenerate ($A_g$) irreducible representation along with threefold ($T_{1u}$, $T_{1g}$, $T_{2u}$, $T_{2g}$), fourfold ($G_u$, $G_g$), and fivefold ($H_u$, $H_g$) degenerate irreducible representations of a regular icosahedron.

As originally established by Jahn and Teller in "Stability of Polyatomic Molecules in Degenerate Electronic States. I. Orbital Degeneracy," *Proceedings of the Royal Society A*, Vol. 161, 1937, pp. 220-235: Nonlinear nuclear configurations are not suitable for a stable orbitally-degenerate electronic state. It is quite significant that the orbital degeneracy considered by Jahn and Teller explicitly excluded a degeneracy due to spin. The bonding and antibonding orbitals of icosahedral boron manifestly involve nonlinear orbitally-degenerate electronic states. The Jahn-Teller effect results in a symmetry-breaking which lifts electronic orbital degeneracies by normal displacements of the 12 nuclei, known as Jahn-Teller-active modes, that distort polyatomic ions and molecules. The vibrational Jahn-Teller-active modes can be described in terms of the same irreducible representations as the electronic state, such that the vibrational state can be specified in terms of the irreducible representations of a regular icosahedron.

In the known boron-rich solids, the icosahedral symmetry is broken and the boron icosahedra are distorted by the Jahn-Teller effect. Most boron-rich solids in the prior art act as inverted molecular solids in which intericosahedral bonds are stronger than the intraicosahedral bonds. Icosahedral boron-rich solids are often referred to as inverted molecules. What is needed in the art is a genus of icosahedral boron-rich solids in which icosahedral symmetry is preserved. Such materials potentially offer electronic properties that are at least as important as those found in graphene, with the further capability of being compatible with monocrystalline silicon using standard manufacturing techniques. An excellent survey of boron-rich solids is given by Emin in "Unusual properties of icosahedral boron-rich solids," *Journal of Solid-State Chemistry*, Vol. 179, 2006, pp. 2791-2798.

There potentially exists a novel form of boron capable of overcoming limitations of the recently discovered allotropes of carbon comprising the fullerenes, carbon nanotubes, and graphene. Although the study of graphene has advanced the general understanding of quantum electrodynamics in condensed matter physics, inherent limitations in its structure and, indeed, the structure of the allotropes of carbon, hinder practical applications. Chief among such limitations is an inability to combine these materials with monocrystalline silicon, on which the electronics industry has been built. Boron, which sits adjacent to carbon on the periodic chart, provides an alternative bridge between quantum electrodynamics and condensed matter physics, with an added benefit that, by carefully controlling its form, it can be integrated with silicon in a highly novel picocrystalline polymorph.

SUMMARY OF THE INVENTION

A novel class of boron-rich compositions that self-assemble from boron, silicon, hydrogen and, optionally, oxygen is disclosed. Self-assembly will occur with or without oxygen and the oxygen content can be varied as required. An impurity that alters electrical properties, hereinafter referred to as a "significant impurity" such as gold, for example, can optionally be included in minor amounts. The compositions can be formed by vapor deposition on a substrate. Monocrystalline silicon can be employed as the substrate. This novel class of self-assembled boron compounds exhibit unique electrical properties.

As used herein "self-assembly", "self-assemble, or "self-assembled" is defined as the spontaneous and irreversible organization of molecular units into ordered structures by non-covalent interactions. One important property of the self-assembled boron compounds of the present invention is that under the specified reaction conditions the reactants spontaneously form into molecular nanostructures that build themselves. Further, the self-assembly of these novel boron compounds is not dependent on a specific substrate or deposition surface.

Thus, this invention pertains to a method for forming self-assembled hydrogen-containing compositions from boron, silicon and, optionally, oxygen. The preferred method of self-assembly is by vapor deposition at relatively low temperatures of reactant gases. The stability of the compositions can be enhanced by ensuring nearly anhydrous conditions during the process. Depending upon the desired characteristics of the compositions, trace amounts of a coinage metal such as gold can be included in the reactant gas mixture.

In accordance with the present invention, the compositions have the formula: $(B_{12}H_4)_xSi_yO_z$, where the boron content is greater than about 50% by relative atomic concentration. These novel solid compositions of matter are hereinafter referred to as "oxysilaborane". Some species of the compositions do not contain oxygen (z=0) and such species may sometimes be referred to as "silaborane." The broadest compositional range of the novel materials disclosed here is represented by "$(B_{12})_xSi_yO_zH_w$", with w, x, y, and z being numbers within the respective ranges of: $0 \leq w \leq 5$, $2 \leq x \leq 4$, $2 \leq y \leq 5$ and $0 \leq z \leq 3$. The preferred stoichiometric range for the compositions is $(B_{12}H_w)_zSi_yO_z$ with $3 \leq w \leq 5$, $2 \leq x \leq 3$, $2 \leq y \leq 5$ and $0 \leq z \leq 3$. Boron is preferably present in from about 63% to about 89% by relative atomic concentration. Particularly preferred compositions are where w=4, x=3, y=5, z=0 and w=4, x=2, y=4, z=2. These compositions can also include trace amounts of significant impurities that do not affect the atomic ratios set forth above. A preferred significant impurity would be a coinage metal such as gold. The oxygen content of the compositions can be varied so as to form regions of higher or lower oxygen content in the oxysilaborane by, for example, controlling the rate of delivery of oxygen containing gases to the reaction site. In like fashion, should it be desirable to employ gold or another significant impurity in trace amounts to alter electrical properties, a metal containing compound can be introduced to the reaction site for deposition along with the self-assembled oxysilaborane. Such trace additions of a significant impurity do not affect the basic stoichiometry of the compositions.

These materials are also unique in that they contain picocrystalline quantum dots that form artificial atoms. The picocrystalline quantum dots (in the form of boron icosahedra with a nearly-symmetrical nuclear configuration) can replace corner silicon atoms in a structure that demonstrates both short-range and long-range order as determined by x-ray diffraction of actual samples. The picocrystalline oxysilaboranes tend to form a borane solid with a continuous network similar to that of monocrystalline silicon, albeit a continuous random network in which certain silicon atoms are orderly replaced by picocrystalline artificial atoms comprising boron icosahedra with a nearly-symmetrical nuclear configuration. Thus, by carefully controlling the reactants and reaction conditions as described below, this new class of materials self assembles boron-based artificial atoms so as to attain a short-range order of nearly-spherical quantum dots and further self assembles those structures (with their quantized energy levels) into materials with a long-range bond-orientational order. This long-range bond-orientational order is physically compatible with monocrystalline silicon, thereby allowing an engineered introduction of the boron picocrystalline quantum dots (artificial atoms) into semiconductor structures by using standard techniques. By varying the oxygen content and the presence or absence of a significant impurity such as gold, unique electrical devices can be constructed that improve upon and are compatible with current semiconductor technology.

BRIEF DESCRIPTION OF THE DRAWING

Preferred embodiments of the invention are illustrated in the accompanying drawings in which:

FIGS. 62 A-B depict energy diagrams believed to reflect the occupied energy levels by valence electrons in negatively-ionized and positively-ionized picocrystalline artificial borane atoms $B_{12}^{2-}H_4$ and $B_{12}^{2+}H_4$ 101, due to disproportionation in picocrystalline silaborane $(B_{12}H_4)_3Si_5$;

FIGS. 75A-D depict energy diagrams illustrating the proposed occupied electronic energy levels of the artificial nuclei of the first- and second-nearest neighbor picocrystalline artificial borane atoms 101 of a pair of conjoined picocrystalline silaborane $(B_{12}H_4)_3Si_5$ and picocrystalline oxysilaborane $(B_{12}^{2-}H_4)_4Si_4O_2^{2+}$ regions 501 and 502;

FIGS. 76A-D depict energy diagrams illustrating proposed occupied electronic energy levels of the artificial nuclei $B_{12}^{2-}$ and $B_{12}^{2+}$ of certain neighboring picocrystalline artificial borane atoms $B_{12}^{2-}H_4$ and $B_{12}^{2+}H_4$ 101 within a picocrystalline silaborane $(B_{12}H_4)_3Si_5$ region 501;

FIGS. 78A-D further depicts a proposed spontaneous mobile charge diffusion mechanism;

FIGS. 79A-D still further depicts a proposed spontaneous mobile charge diffusion mechanism;

DESCRIPTION OF THE PREFERRED EMBODIMENTS

A new type of solid composition of matter derived from the heating of boron and silicon hydrides in the presence of hydrogen and, optionally, an oxidizing chemical agent is disclosed. The compositional range of preferred materials, hereinafter referred to as "picocrystalline oxysilaboranes" and represented by the formula "$(B_{12}H_4)_xSi_yO_z$" comprises $(B_{12}H_4)_4Si_4$ at one extreme and $(B_{12}^{2-}H_4)_2Si_4O_2^{2+}$ at the opposite extreme, with x, y, and z being numbers in the preferred respective ranges of: $2 \leq x \leq 4$, $3 \leq y \leq 5$ and $0 \leq z \leq 2$. Picocrystalline oxysilaborane $(B_{12}H_4)_xSi_yO_z$ is itself contained in a broader compositional range of novel materials, also discussed here for the first time and hereinafter referred to as "oxysilaboranes" and represented by "$(B_{12})_xSi_yO_zH_w$", with w, x, y, and z being numbers in the respective ranges: $0 \leq w \leq 5$, $2 \leq x \leq 4$, $2 \leq y \leq 5$ and $0 \leq z \leq 3$. When no oxygen is present (z=0), the materials are referred to as simply "silaboranes" as they are formed from hydrogen, boron and silicon.

The picocrystalline oxysilaboranes of this invention are nearly transparent solids believed to be constituted by a continuous random network of polymorphic unit cells that satisfy a modification of rules established by Zachariasen, "The Atomic Arrangement in Glass," *Journal of the American Chemical Society*, Vol. 54, 1932, pp. 3841-3851. Zachariasen focused upon oxide glasses and, more specifically, on amorphous $SiO_2$ and amorphous $B_2O_3$. Zachariasen established that amorphous $SiO_2$ is formed by a continuous random network of $SiO_4$ tetrahedra. Similarly, the picocrystalline oxysilaboranes are believed to be constituted by a continuous random network of polyhedra with a nearly-symmetrical boron icosahedron at each of the polyhedral corners.

Figure 1:
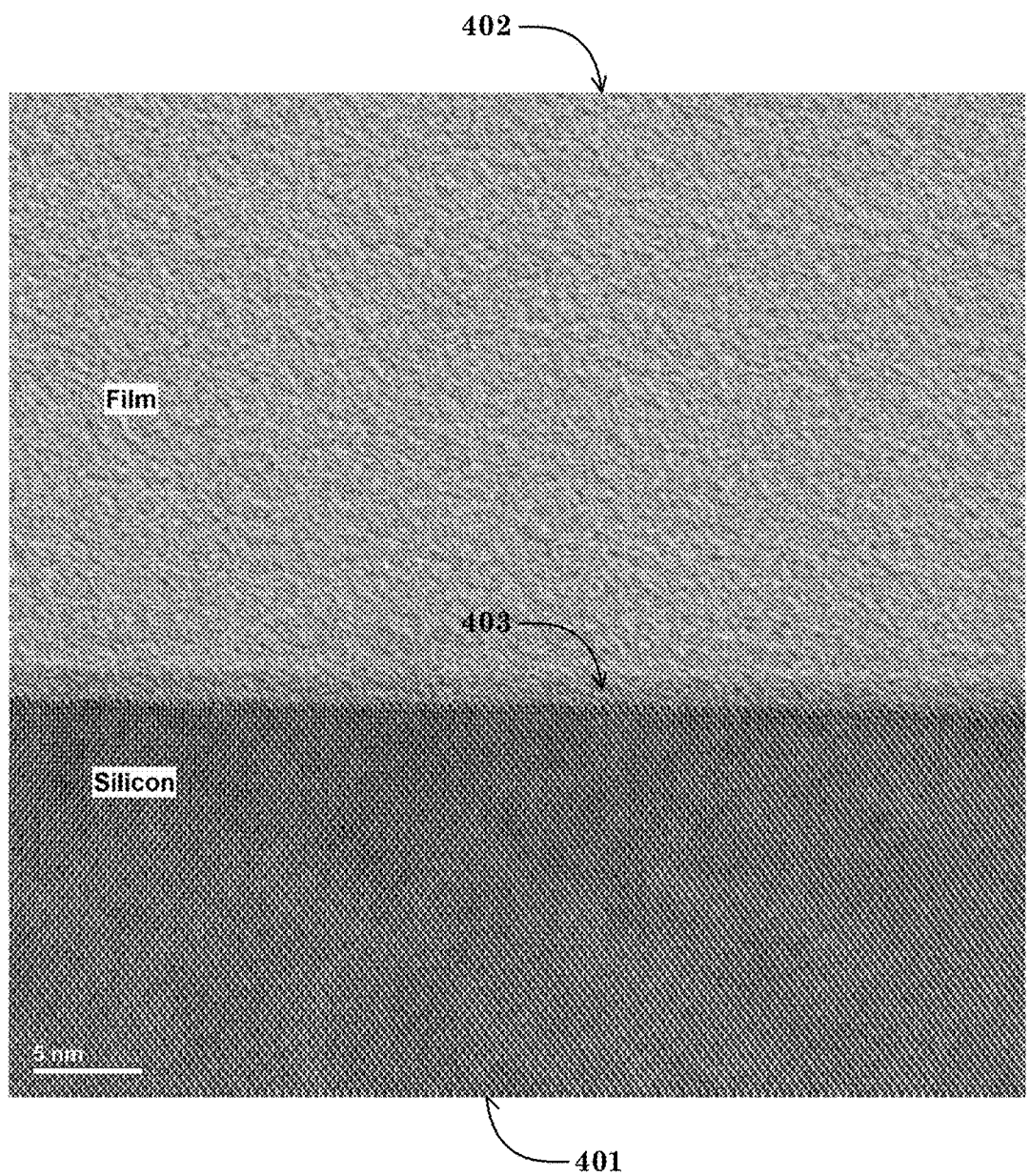
FIG. 1 is a micrograph obtained by high-resolution transmission microscopy (HRTEM) of a picocrystalline borane solid deposited on a monocrystalline substrate.
Figure 2:
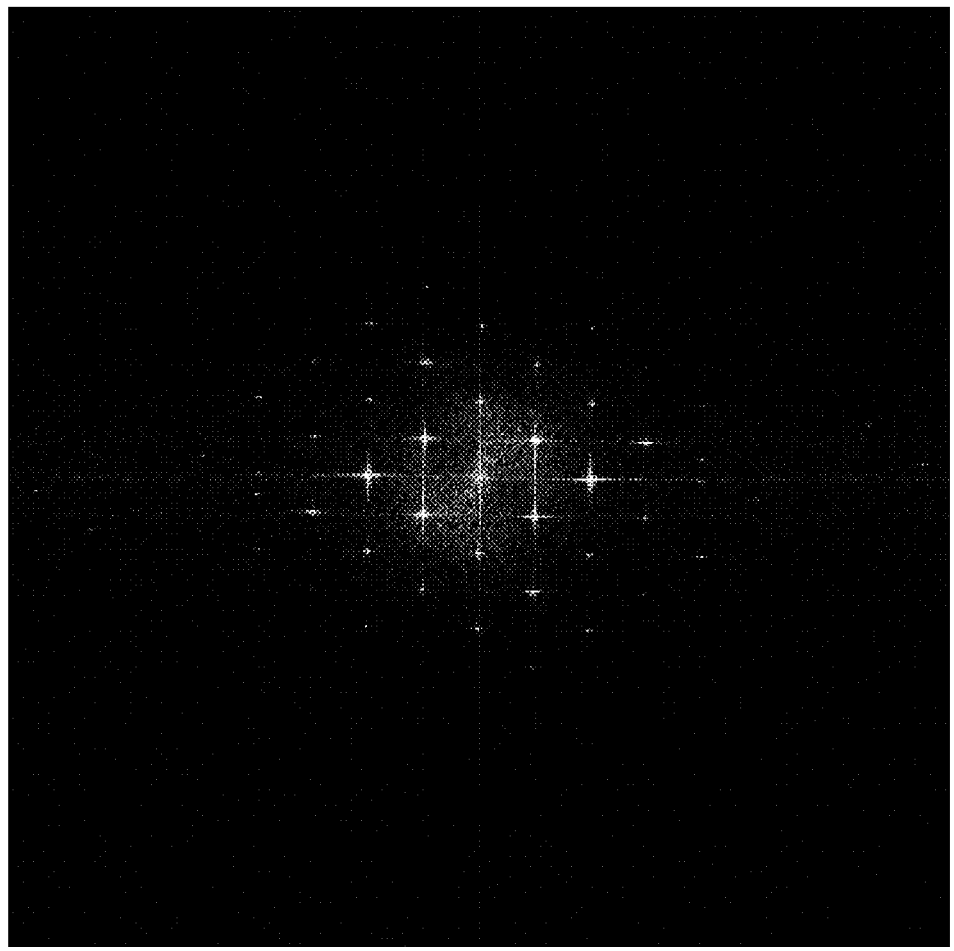
FIG. 2 is an HRTEM fast Fourier transform (FFT) image of the monocrystalline silicon substrate.
Figure 3:
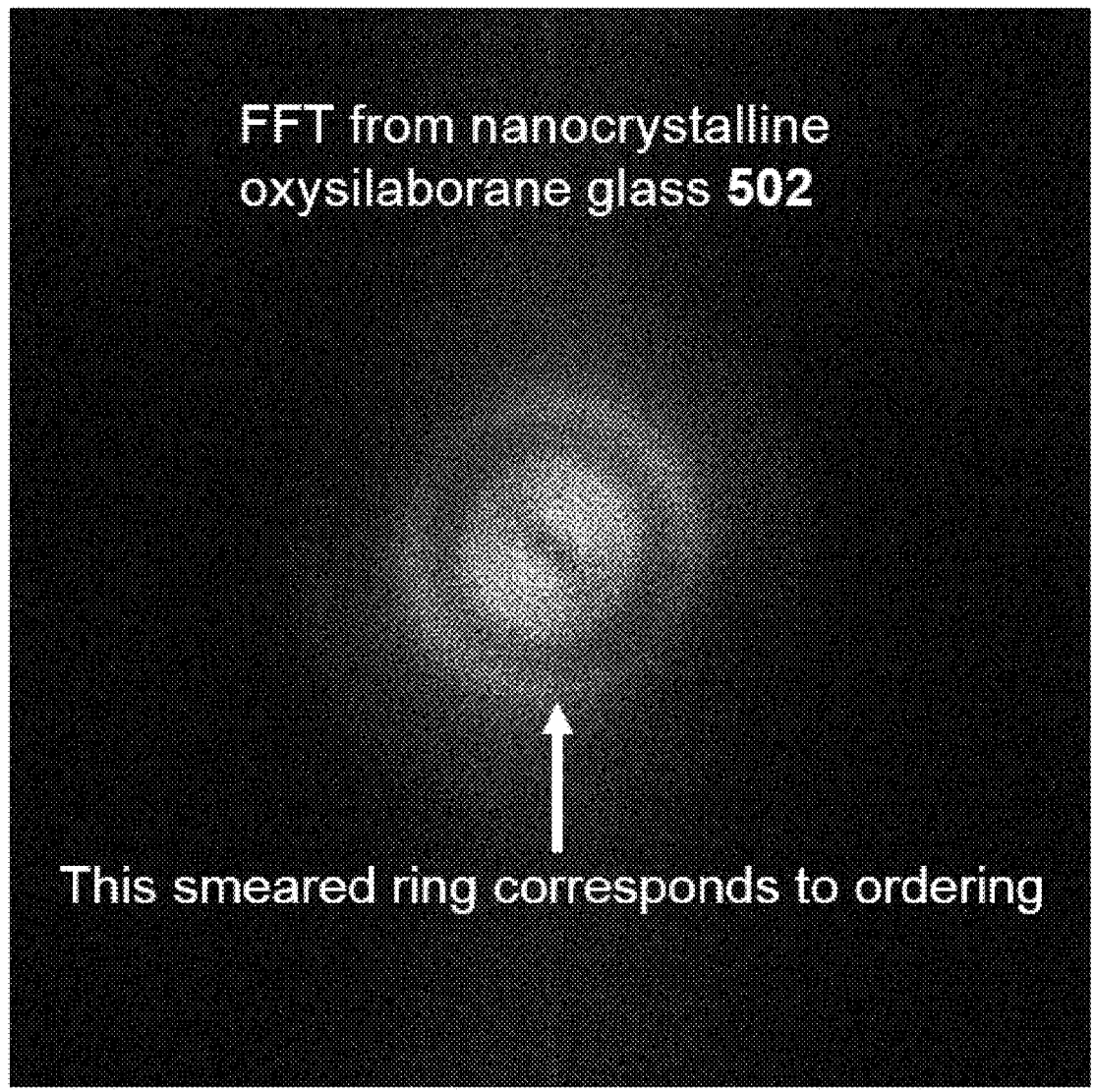
FIG. 3 is an FFT image of the picocrystalline borane solid.

In order to illustrate the fact that the novel oxysilaborane compositions are neither amorphous nor monocrystalline, but instead exhibit a novel combination of short-range and long-range order, reference is made to data collected from actual samples of the materials. FIG. 1 shows a micrograph that was obtained by high-resolution transmission electron microscopy (HRTEM) of a picocrystalline borane solid 402 deposited on a monocrystalline (001) silicon substrate 401. The interfacial layer 403 is due to the particular conditions of its deposition. An HRTEM fast Fourier transform (FFT) image of the monocrystalline silicon substrate 401 is shown in FIG. 2. A similar FFT image of the picocrystalline borane solid 402 is shown in FIG. 3. Whereas the FFT image of the silicon substrate 401 in FIG. 2 is characteristic of a monocrystalline (001) silicon lattice with a long-range periodic translational order, the FFT image of the picocrystalline solid 402 in FIG. 3 exhibits a short-range order that is not characteristic of a monocrystalline lattice or an amorphous solid. The various types of order will now be further defined and further explained.

Figure 4:
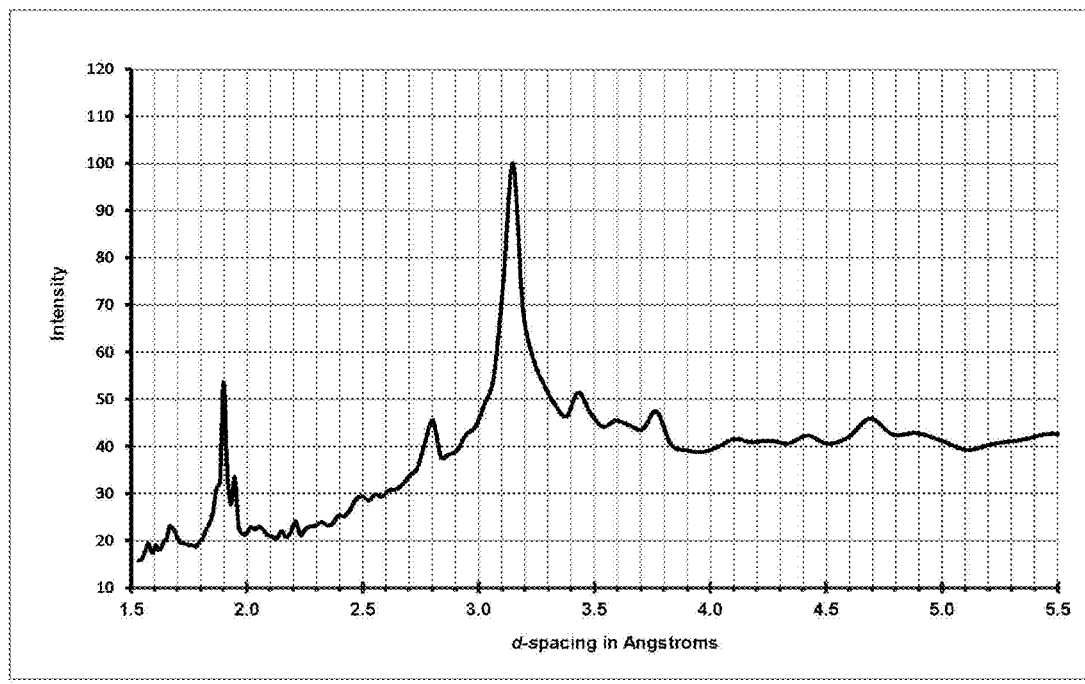
FIG. 4 is a graph in terms of interplanar lattice d-spacings of the HRTEM diffraction intensity of the monocrystalline silicon substrate.

To better illustrate the short-range order of the picocrystalline borane solid 402, the HRTEM diffraction intensity of the monocrystalline silicon substrate 401 is graphed in FIG. 4 in terms of the interplanar lattice d-spacings between parallel Bragg planes of atoms that support a constructive electron wave interference. The highest-intensity peak in FIG. 4 is associated with the interplanar d-spacing of 3.135 Å between parallel {111} planes of atoms in the monocrystalline silicon substrate 401. The other high-intensity peak in FIG. 4 is associated with an interplanar d-spacing of 1.920 Å between parallel {220} planes of atoms in the monocrystalline silicon substrate 401. No singular high-intensity peak occurs in the FFT diffraction pattern of the picocrystalline borane solid 402 shown in FIG. 5, which was obtained by HRTEM microscopy.

Figure 5:
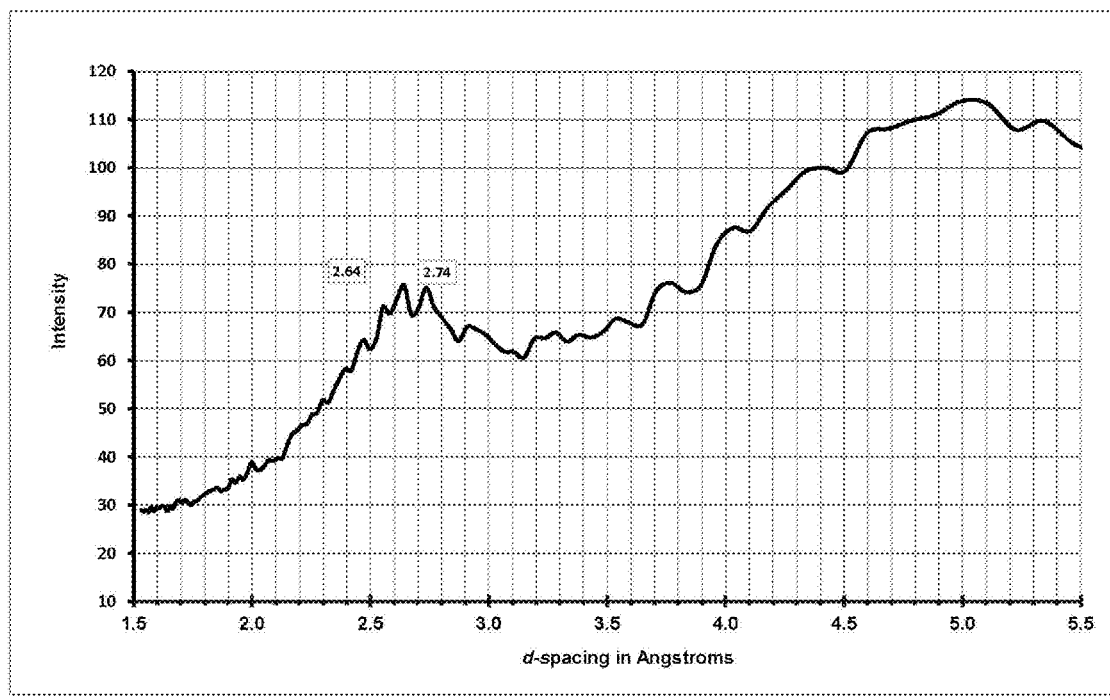
FIG. 5 is a graph in terms of interplanar lattice d-spacings of the HRTEM diffraction intensity of the picocrystalline borane solid.
Figure 6:
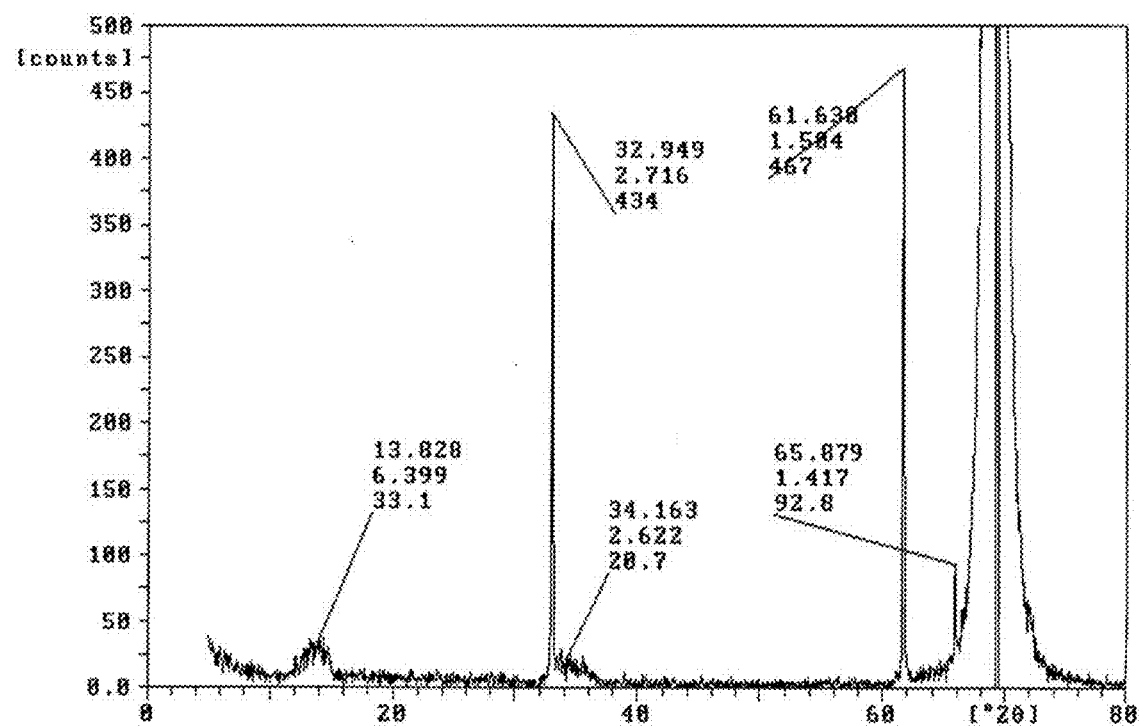
FIG. 6 is a conventional ω-2θ x-ray diffraction (XRD) pattern of a self-assembled picocrystalline borane solid.

The broadened circular ring in the FFT image of the picocrystalline borane solid 402 in FIG. 3 can be related to broadened interplanar lattice spacings between d=2.64 Å and d=2.74 Å in FIG. 5. In order to more fully understand the physical significance of the smeared ring, it is highly purposeful to consider a conventional ω-2θ x-ray diffraction (XRD) pattern of a thin picocrystalline borane solid, as shown in FIG. 6. In a conventional ω-2θ XRD diffraction pattern, the angle of incidence ω of the x-ray beam and the angle 2θ of the diffracted x-ray beam are held relatively constant and collectively varied together over the x-ray diffraction angle 2θ. By so doing, a set of regularly-spaced lattice planes results in a sharp diffraction peak. The thin picocrystalline borane solid scanned in FIG. 6 was also deposited over a monocrystalline (001) silicon substrate. The high-intensity peaks shown in FIG. 6 are associated with x-ray diffraction from regularly-spaced silicon lattice planes in the monocrystalline (001) silicon substrate.

Figure 7:
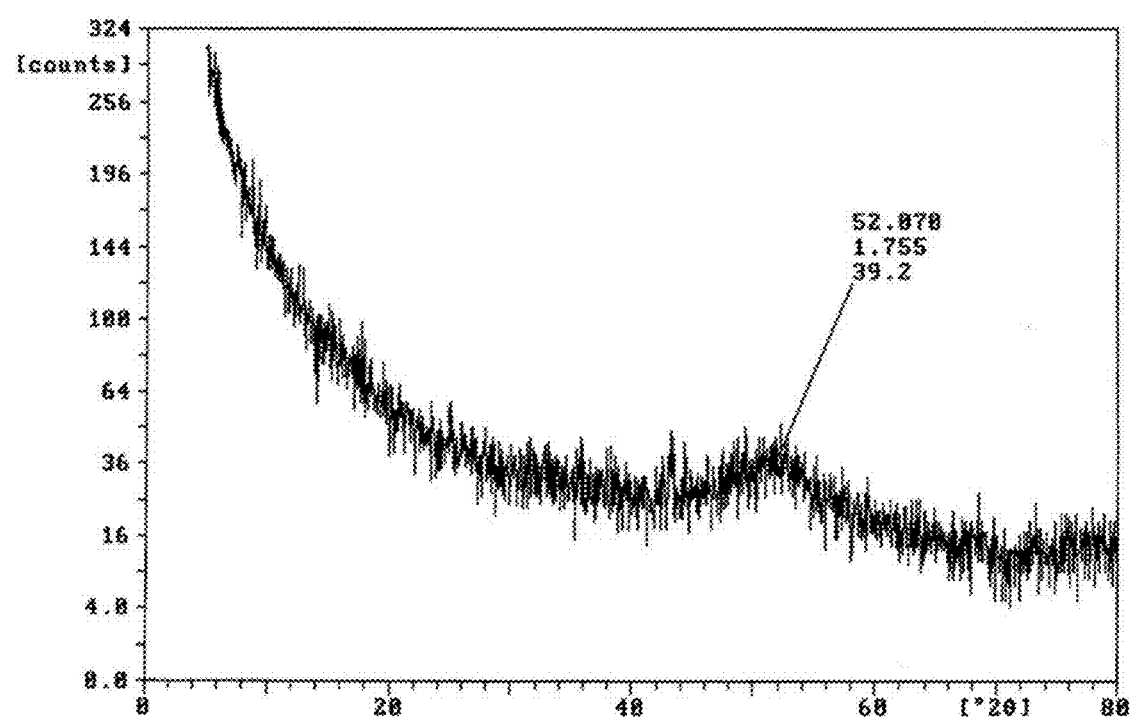
FIG. 7 is a grazing-incidence x-ray diffraction (GIXRD) scan of the same self-assembled picocrystalline borane solid in FIG. 6.

There are two broadened diffraction peaks located near 2θ=13.83° and 2θ=34.16° in FIG. 6. Both of the two low-intensity broadened diffraction peaks are associated with the thin picocrystalline borane solid. In order to separate the diffraction peaks associated with the thin film from those associated with the silicon substrate, a grazing-incidence x-ray diffraction (GIXRD) spectroscopy was employed. This type of spectroscopy is also referred to as glancing-angle x-ray diffraction. Both of these two terms will be utilized interchangeably. A GIXRD scan of the same picocrystalline borane solid scanned in FIG. 6 is shown in FIG. 7. For a sufficiently low incidence angle ω, GIXRD diffraction peaks are due to regularly-spaced lattice planes of atoms existing in the thin picocrystalline borane solid—not in the monocrystalline silicon substrate.

Figure 8:
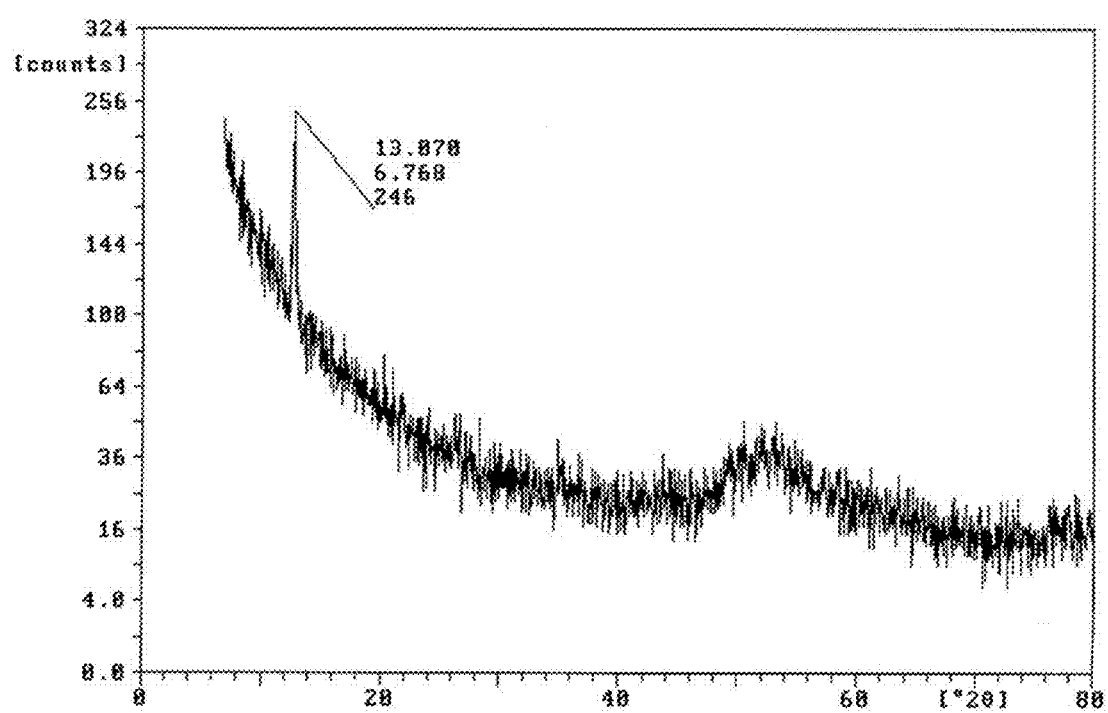
FIG. 8 is a second GIXRD scan of the same self-assembled picocrystalline borane solid scanned in FIG. 6.

The picocrystalline borane solid appears to be an amorphous film in FIG. 7 except, perhaps, for a broadened short-range order near the diffraction angle of 2θ=52.07°. In the GIXRD scan of the picocrystalline borane solid shown in FIG. 8, the fixed angle of incidence of the x-ray beam was ω=6.53° and the x-ray detector was varied over a wide range of diffraction angles from 2θ=7.0° to 2θ=80°. A sharp low-intensity x-ray peak occurs at 2θ=13.07 in FIG. 8. This x-ray diffraction peak corresponds to an interplanar lattice d-spacing of d=6.78 Å, which is contained in the broad range of low-intensity x-ray peaks near 2θ=13.83° in FIG. 6. This x-ray diffraction peak relates to the Bragg condition of the fixed x-ray angle of incidence ω=6.53°. If the fixed x-ray angle of incidence co is changed, a different Bragg peak is obtained in correspondence to the new x-ray angle of incidence co in another GIXRD scan. This range of low-intensity GIXRD peaks, related to the x-ray angle of incidence co, proves a picocrystalline borane solid is not amorphous.

However, the analysis further establishes that a picocrystalline borane solid is not polycrystalline. A polycrystalline film is comprised of a large number of crystalline grains that are randomly ordered, such that all sets of regular interplanar lattice spacings are brought into a Bragg condition in a GIXRD scan by virtue of the random ordering of the polycrystalline grains. The lack of any sharp peak in FIG. 7 indicates the absence of randomly ordered crystalline grains. The possible explanation of the structure of a picocrystalline borane solid is now posited by reconciling experimental diffraction data with the belief that the boron icosahedra retain a nearly-symmetrical nuclear configuration, which is not observed in any known boron-rich solid in the prior art.

Preferred embodiments of this present invention involve a type of order not known in the prior art. Long-range periodic translational order is defined herein as a regular repetition of a certain invariant arrangement of atoms, known as a unit cell, over space so as to thereby form a translationally-invariant tiling in a regular array of atoms well beyond first- and second-nearest neighbor atoms. Monocrystalline and polycrystalline materials possess a long-range periodic translational order throughout space. The periodic repetition of atomic positions is maintained throughout the entire space of a monocrystalline material. In a polycrystalline material, a periodic repetition of atomic positions is maintained over the limited, finite space in grains, which can themselves be arbitrarily oriented over the entire space of a polycrystalline material. As used herein, a nanocrystalline material is a special polycrystalline material wherein the grain sizes range between 300 nm and 300 pm.

Short-range periodic translational order is defined herein as a repetition of atomic positions over a space substantially confined to only first- and second-nearest neighbor atoms. The radii of isolated neutral atoms range between 30 and 300 pm. As the result, and as used herein, a picocrystalline material is a material exhibiting a short-range periodic translational order limited to repeating atomic positions in finite groups of first- and second-nearest neighbor natural atoms. An amorphous material, as used herein, is a material void of regularly repeating arrangements of atoms, so as to be incapable of supporting a constructive interference of x-rays.

It might seem that these definitions of various types of crystalline materials fully describe the allowable order of repeating atomic positions in space. But, these definitions remain limited in the sense that they are based strictly upon repeating positions of individual atoms over space. They cannot be applied to materials that include tightly packed clusters of atoms arranged in space such that the clusters may themselves be bonded to single atoms that are not so clustered. These definitions must be extended in order to comprehend a quantum dot, which is defined, for purposes herein, as a cluster of atoms in which a discrete quantization of energy levels occurs. The size of a typical quantum dot in the prior art is on the order of 10 nm. The above noted definitions of the various types of solid crystalline materials are also independent of any energy quantization. This leads to the requirement for a new definition that comprehends both the spatial arrangement of atoms and also the presence of a discrete quantization of energy levels. Therefore, as used herein, a "picocrystalline artificial atom" is a cluster, of a size less than 300 pm, of natural atoms that are mutually bonded together so as to support a short-range periodic translational order and an internal discrete quantization of energy levels. As further described below, special types of picocrystalline artificial atoms can also be bonded to other natural atoms in order to form an extended lattice of natural atoms and picocrystalline artificial atoms. As used herein, a natural atom is any isotope of a stable chemical element contained in the periodic chart.

A particular type of picocrystalline artificial atom utilized in embodiments of this invention is a boron icosahedron with a nearly-symmetrical nuclear configuration which escapes Jahn-Teller distortion. The boron icosahedra in most all known boron-rich solids exhibit a broken icosahedral symmetry due to Jahn-Teller distortion, such that the first and second-nearest neighbor boron atoms do not exist in repeating spatial positions that are capable of supporting a short-range periodic translational order. Most boron icosahedra in the prior art are bonded by the molecular orbitals obtained by Longuet-HIGGINS and Roberts in the paper entitled "The Electronic Structure of an Icosahedron of Boron," *Proceedings of the Royal Society A*, Vol. 230, 1955, p. 110.

Figure 9:
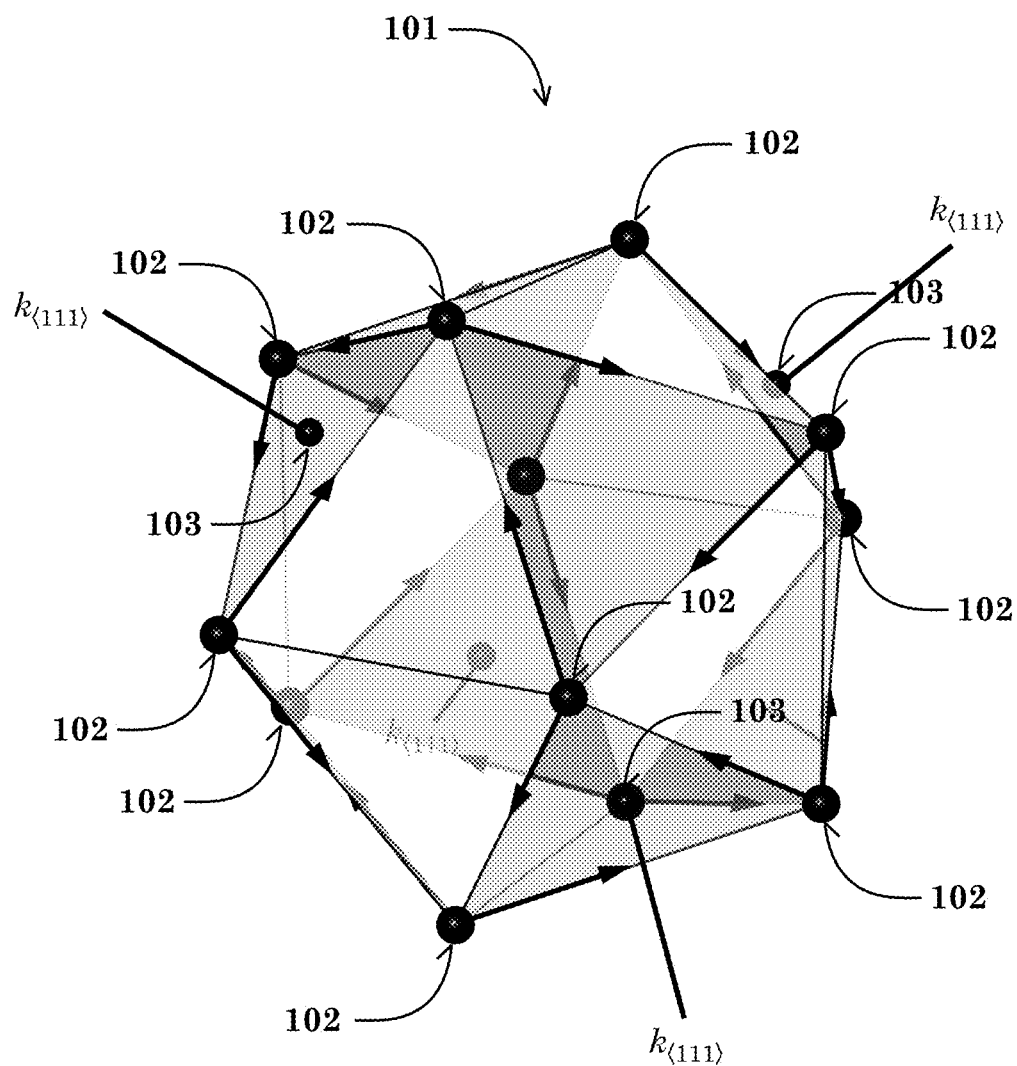
FIG. 9 is an illustration of a regular boron icosahedron with a symmetrical nuclear configuration shown with four hydrogens bonded by a Debye force.

In their molecular orbital analysis, Longuet-Higgins and Roberts never resolved the atomic orbitals of the three-center boron bond in terms of the icosahedral symmetry operations. In connection with the invention described here, a molecular orbital analysis that describes the three-center boron bonds by a generalization of the methodology of Longuet-Higgins and Roberts was performed. That generalized molecular orbital analysis describes a boron icosahedron comprising 12 boron nuclei 102, with a nearly-symmetrical nuclear configuration, that can be formed by 24 delocalized atomic orbitals so as to result in a nearly-symmetrical spheroid with all displacement ideally restricted to only periodic vibrations along the four $k\langle 111\rangle$ wave vectors shown in FIG. 9. An electric quadrupole moment along the km) wave vectors induces an electric dipole moment in the hydrogen atoms, such that the four hydrogen nuclei 103 bond by a Debye force, as shown in FIG. 9. The Debye force orients each valence electron of the hydrogen nuclei 103 along a $k\langle 111\rangle$ wave vector. The boron icosahedron 101 described above, and shown in FIG. 9, is more particularly referred to as a "picocrystalline artificial borane atom 101".

Figure 10:
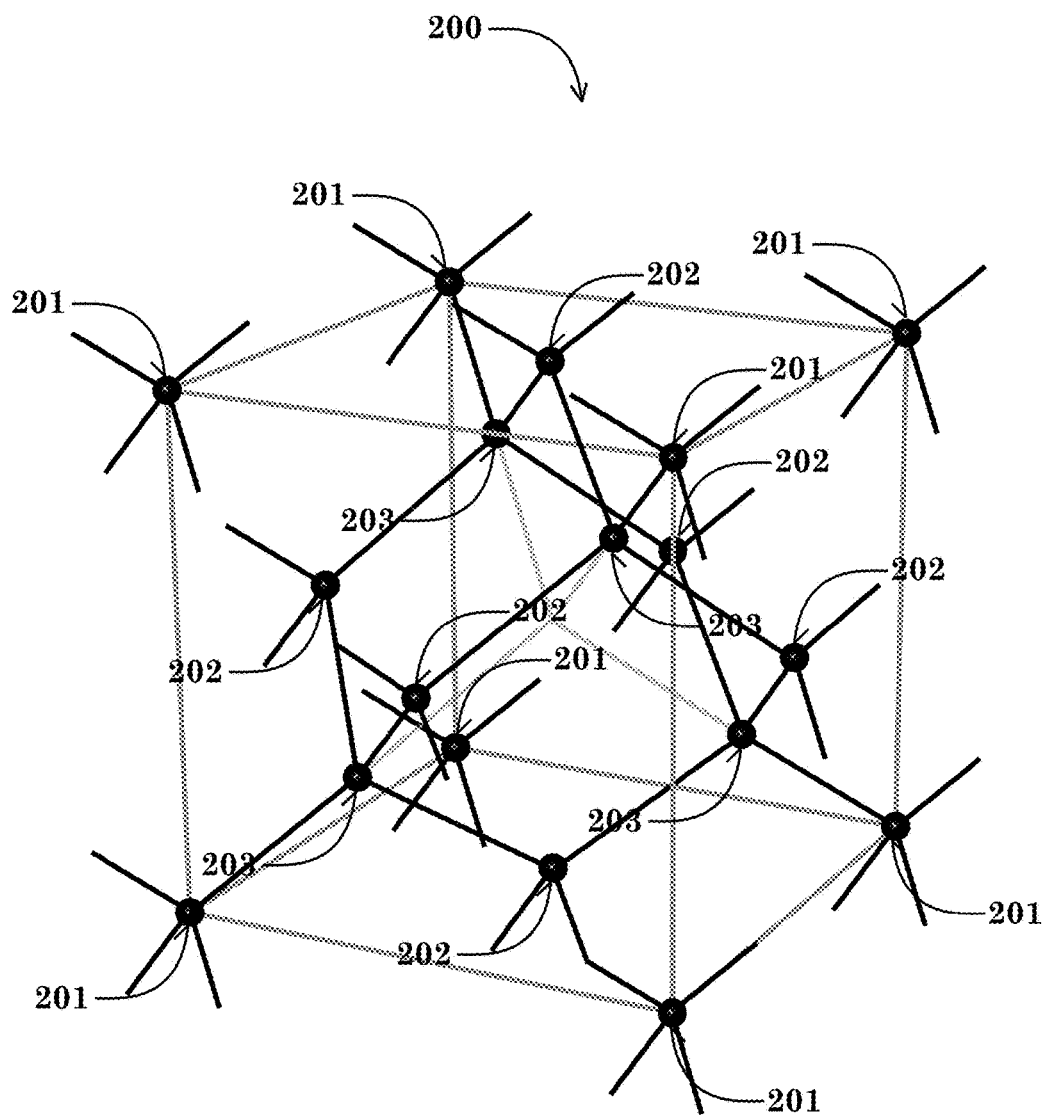
FIG. 10 is an illustration of a monocrystalline silicon unit cell.

The self-assembly of the picocrystalline oxysilaboranes involves the self-selective replacement of silicon atoms in a monocrystalline silicon lattice by boron icosahedra with a nearly-symmetrical nuclear configuration in the form of picocrystalline artificial borane atoms 101. To further illustrate the order present in picocrystalline oxysilaboranes, the characteristic order of the unit cell of monocrystalline silicon, prior to such self-selective replacement of silicon atoms, will be explained. The monocrystalline silicon unit cell 200 in FIG. 10 is comprised of 8 silicon vertex atoms 201, 6 silicon face-center atoms 202, as well as 4 silicon basis atoms 203. The basis atoms 203 reside along a $\langle 111\rangle$ cubic body diagonal in a tetrahedral arrangement. The monocrystalline silicon unit cell 200 is periodically translated over space so as to form a monocrystalline silicon lattice in which the silicon vertex atoms 201 and the silicon face-center atoms 202 are covalently bonded to, and only to, silicon basis atoms 203 along a $\langle 111\rangle$ crystalline orientation. The resultant monocrystalline silicon lattice has a long-range periodic translational order in terms of cubic unit cells of ~543 pm along each edge, without any $\langle 100\rangle$ chemical bonds.

Per the normal crystallographic convention, a crystal orientation along, or parallel to, any cubic edge is generally represented by $\langle 100\rangle$. Any particular $\langle 100\rangle$ orientation, e.g. the [010] orientation along the positive y-axis, will be specifically denoted. A cubic face, or a plane parallel to any cubic face, is generally represented by $\{100\}$. A particular $\{100\}$ plane, e.g. the xz-plane normal to the [010] direction, is represented by (010). A particular $\langle 100\rangle$ orientation, e.g. the [010] orientation, is always normal to the corresponding $\{100\}$ plane, viz. the (010) plane in this case. By further convention, any orientation along, or parallel to, a cubic body diagonal is represented by $\langle 111\rangle$. There are two classes of icosahedral faces: 8 icosahedral faces are constituted by $\{111\}$ planes normal to a $\langle 111\rangle$ cubic body diagonal and 12 icosahedral faces are constituted by planes intersecting in pairs along a $\langle 100\rangle$ orientation. The generalized molecular orbital analysis predicts that the atomic orbitals of three-center boron bonds exist along edges of the $\{111\}$ planes.

The above-described picocrystalline artificial borane atoms 101 can now be utilized to address an existing limitation in semiconductor fabrication. The invariance of the dimensions of the monocrystalline silicon unit cell 200 is maintained in the presence of extensive valence electron eigenstate changes by a spatial displacement of the silicon basis atoms 203 along a $\langle 111\rangle$ crystal orientation. It is quite significant that the silicon vertex atoms 201 and silicon face-center atoms 202 are ideally motionless while the silicon basis atoms 203 can be displaced along a $\langle 111\rangle$ cubic body diagonal. A change in eigenstate of a valence electron eigenfunction involves a change in spatial extension of the electron eigenfunction. The diamond lattice of monocrystalline silicon supports extensive changes in valence electron eigenstates, without mechanical work, due to an invariant lattice constant of the constituent unit cells. The basis atoms 203 support a long-range $\langle 111\rangle$ bond-orientational order that complements the long-range periodic translational order.

The practical means to exploit the ability of a solid monocrystalline silicon lattice to support extensive changes in eigenstate in the absence of any mechanical work is fundamentally limited by its very structure. First, monocrystalline silicon can only be epitaxially deposited over monocrystalline silicon substrates. Secondly, the termination of a monocrystalline silicon lattice, in order to electrically contact it, results in Tamm-Shockley states which pin the electrochemical potential within the forbidden energy region between the bottom of the conduction band and top of the valence band. This pinning of the electrochemical potential results in a rectifying contact independent of the metal work function of electrodes. See Bardeen, by way of example, "Surface States at a Metal Semi-Conductor Contact," *Phys. Rev.* 10, No. 11, 1947, p. 471. Thus, it is desirable for the Tamm-Shockley interface state density to be substantially reduced.

By well-established processing techniques, a substantial reduction in the Tamm-Shockley interface state density can be achieved by terminating crystalline silicon regions with an amorphous silicon dioxide film such that the surface electrochemical potential can be modulated, in device operation, throughout the forbidden energy region. A field-effect transistor exploits the ability to modulate the electrical conductivity of a monocrystalline silicon surface by capacitively-coupled electrodes via an intervening silicon dioxide thin-film. However, the silicon dioxide must be removed from semiconductor contact regions due to the high resistivity of silicon dioxide ~$10^{16}$ Ω-cm. In order to reduce the Tamm-Shockley interface states in the semiconductor contact zones, the semiconductor surface is degenerately doped, such that the electrochemical potential can be selectively pinned in either the conduction energy band or the valence energy band.

A metal or a silicide can be alloyed to the degenerate semiconductor surface, such that mobile charges can tunnel through the potential barrier into the isotype homojunction. Under low-level injection, the isotype homojunction behaves as an ohmic contact to any high-resistivity semiconductor region. However, this widely-used type of ohmic contact prevents the employment of a monocrystalline semiconductor in an electrochemical rectifier wherein the electrochemical potential can vary between the external electrodes. So, as only one example of the many useful properties of novel materials described herein, this deficiency is remedied by the incorporation of picocrystalline artificial borane atoms 101, shown in FIG. 9, into the monocrystalline silicon unit cell 200, shown in FIG. 10, so as to form a picocrystalline unit cell with a bond-orientational order that is compatible with the long-range bond-orientational order of monocrystalline silicon.

Figure 11:
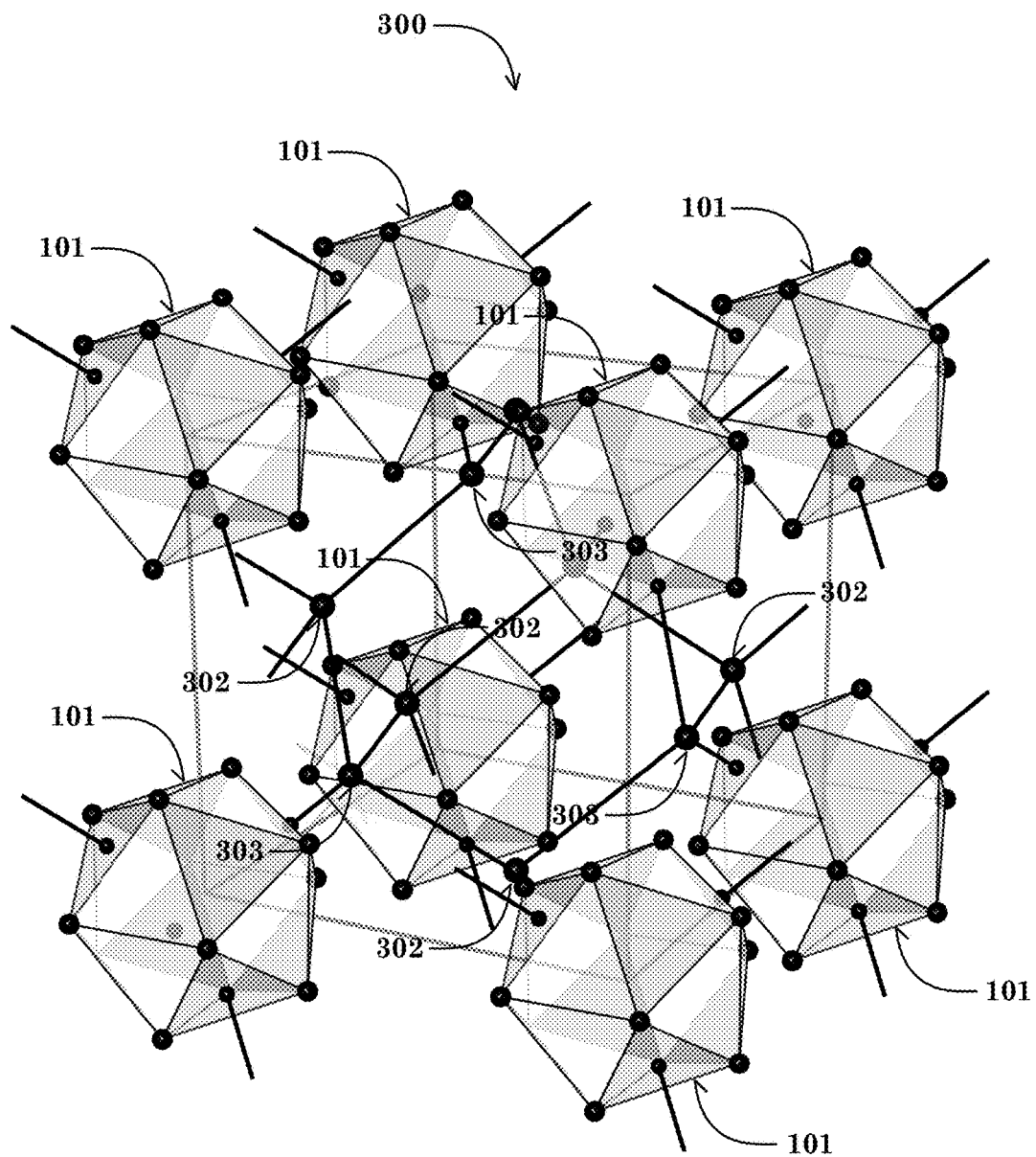
FIG. 11 is an illustration of a diamond-like picocrystalline unit cell.

A diamond-like picocrystalline silaborane unit cell 300 is constructed by replacing each silicon vertex atom 201 within the monocrystalline silicon unit cell 200 with a picocrystalline artificial borane atom 101, as shown in FIG. 11. The 8 picocrystalline artificial borane atoms 101 at the vertices of the silaborane unit cell 300 in FIG. 11 are shared by 8 picocrystalline silaborane unit cells 300 in an extended solid lattice (not shown). A periodic translation of the picocrystalline silaborane unit cell 300 over space would, thereby, result in a picocrystalline silaborane $(B_{12}H_4)Si_7$ lattice, which effectively acts as a self-assembled diamond-like picocrystalline lattice structurally similar to monocrystalline silicon. Picocrystalline artificial borane atoms 101 in FIG. 11 replace the 8 silicon vertex atoms 201 in FIG. 10 in the picocrystalline silaborane $(B_{12}H_4)Si_7$ lattice, such that the boron nuclei 102 (FIG. 9) remain in a nearly-symmetrical nuclear configuration while the hydrogen nuclei 103 (FIG. 9) vibrate along the $k\langle 111 \rangle$ wave vectors of the four $\langle 111 \rangle$ threefold axes.

Whereas an oxide glass is constituted by a continuous random network of oxygen tetrahedra or oxygen triangles, the picocrystalline oxysilaboranes constitute a solid formed by a continuous random network of borane hexahedra, which, by definition, form a hexahedron with a picocrystalline artificial borane atom 101 at each hexahedral corner. Whereas the monocrystalline silicon unit cell 200 in FIG. 10 is a regular hexahedron (cube), the oxysilaborane unit cell 300 in FIG. 11, while depicted for description purposes as a cube, is actually an irregular hexahedron.

Whereas Zachariasen represented the atomic arrangement of any oxide glass by means of a continuous random network of polymorphic oxygen tetrahedra or polymorphic oxygen triangles, the atomic arrangement of a borane solid will now be established in terms of a continuous random network of irregular polymorphic borane hexahedra 300. The eight corners of the borane hexahedron 300 shown in FIG. 11 are comprised of corner picocrystalline artificial borane atoms 101. Each corner picocrystalline artificial borane atom 101 is, ideally, bonded to four tetravalent natural atoms 303 that are surrounded by eight corner picocrystalline artificial borane atoms 101. The preferred tetravalent natural atoms 303 are natural silicon atoms.

Each tetravalent natural atom 303 bonds to one or more face-center atom 302 in the borane hexahedron 300 shown in FIG. 11. The face-center atom 302 can be any of, but not limited to: a tetravalent natural atom such as silicon; a hexavalent natural atom such as oxygen; or a tetravalent picocrystalline artificial borane atom 101. With the help of the irregular borane hexahedron 300 shown in FIG. 11, the atomic arrangement of a borane solid can be understood by changes in Zachariasen's rules for an oxide glass. First, four tetravalent natural atoms 303 are surrounded by 8 corner picocrystalline artificial borane atoms 101 in a solid borane lattice. Secondly, the irregular borane hexahedra 300 share corner picocrystalline artificial borane atoms 101 within a continuous random network. The centroid of each corner picocrystalline artificial borane atom 101 is, ideally, motion-invariant. Thirdly, each corner picocrystalline artificial borane atom 101 covalently bonds to four tetravalent natural atoms 303 along a $\langle 111 \rangle$ crystalline orientation.

Unlike an oxide glass, the picocrystalline oxysilaboranes form a borane solid by a continuous random network of borane hexahedra 300 in which the hexahedral edges and faces are shared, in addition to the eight corners. Whereas the borane hexahedron 300 is represented as a cube in FIG. 11, for descriptive purposes, the borane hexahedra 300 comprising the continuous random network of the picocrystalline oxysilaboranes are, in actuality, irregular hexahedra that cannot be associated with a invariant cubic lattice constant.

For a regular boron icosahedron with an ideal edge of 1.77 Å, the interplanar lattice spacing of the ten sets of parallel triangular faces in each picocrystalline artificial borane atom 101 is d=2.69 Å. This intraicosahedral plane spacing corresponds to a diffraction angle of 2θ=33.27° for 1.54 Å x-rays (which is x-ray wavelength used in all the XRD scans in the figures herein). This diffraction angle is contained within the broadened, low-intensity diffraction peak near 2θ=34.16° in the ω-2θ XRD scan shown in FIG. 6—which, in turn, is related to the smeared circular electron diffraction ring in FIG. 3. It is now purposeful to provide a possible explanation for the broadening of the x-ray and electron diffraction peaks and rings in the picocrystalline oxysilaboranes.

There is a geometric distortion due to the mixture of boron isotopes $_5^{10}B$ and $_5^{11}B$ in boron icosahedra comprising the picocrystalline oxysilaboranes, which causes a broadening of the Bragg peaks associated with the intraicosahedral constructive x-ray diffraction patterns due to the ten sets of nearly-parallel plane faces of the constituent boron icosahedra. However, it is believed that this distortion is similarly preserved in most of the boron icosahedra, such that Bragg peaks are associated with intericosahedral constructive x-ray diffraction patterns between parallel planes of the picocrystalline artificial borane atoms 101 at the corners of the irregular borane hexahedra 300 forming a continuous random polyhedral network. The distance between the body centers of the corner picocrystalline artificial borane atoms 101 varies randomly, such that sharp Bragg peaks exist between corresponding parallel icosahedral faces of different picocrystalline artificial borane atoms 101 for each x-ray angle of incidence over a broad diffraction angle range near 2θ=13.83°.

A nanocrystalline solid, as used herein, is taken to be a polycrystalline solid with small grains, with grain sizes being less than 300 nm. As the grain size is reduced, then the periodic translational order is of a shorter range and the x-ray diffraction peaks are broadened. Whereas a typical nanocrystalline material is void of any long-range order, the picocrystalline oxysilaboranes of this invention possess a short-range periodic translational order along with a long-range bond-orientational order that is believed to be due to the self-alignment of the picocrystalline artificial borane atoms 101. By a definition herein, a picocrystalline borane solid is a solid, comprised of at least boron and hydrogen, that possesses a long-range bond-orientational order due to sharp x-ray diffraction peaks when subjected to grazing-incidence x-ray diffraction (GIXRD).

In order to understand the long-range bond-orientational order which characterizes the picocrystalline oxysilaboranes, it is purposeful to focus on the picocrystalline artificial borane atoms 101. The ten pairs of nearly-parallel faces of a picocrystalline artificial borane atom 101 are ideally separated by d=269 pm, which supports a broad intraicosahedral x-ray diffraction peak at 2θ=33.27. As discussed, the intraicosahedral x-ray diffraction peaks in a picocrystalline artificial borane atom 101 are broadened by a mixture of the boron isotopes $_5^{10}B$ and $_5^{11}B$. It is purposeful to more precisely define as to what is meant by "broad" and "sharp" x-ray diffraction peaks.

Any sharp x-ray diffraction peak is characterized by a peak width at half intensity that is at least five times smaller than the peak height. Conversely, a broad x-ray diffraction peak is characterized by a peak width, at half intensity, which is greater than half the peak height. The very broad x-ray diffraction peak near 2θ=52.07° in FIG. 7 is characteristic of very small grains. The x-ray diffraction peak near 2θ=34.16° in the ω-2θ XRD scan in FIG. 6 is a broad diffraction peak due to constructive intraicosahedral x-ray diffraction between opposite icosahedral faces of picocrystalline artificial borane atoms 101. The preferred embodiments of this invention comprise picocrystalline artificial borane atoms 101 that intrinsically support a broad x-ray diffraction peak near 2θ=33.27°, which, as noted above, corresponds to nearly-parallel icosahedral faces separated by approximately d=269 pm. The three-dimensional lattice of the picocrystalline oxysilaboranes is constituted by the translation of an irregular borane hexahedra 300 formed from picocrystalline artificial borane atoms 101, natural silicon atoms, and possibly natural oxygen atoms.

The fivefold symmetry of a regular icosahedron is incompatible with the fourfold symmetry of a regular hexahedron (cube), such that it is impossible to periodically translate any regular hexahedral unit cell, with picocrystalline artificial borane atoms 101 at the vertices, over space in a translationally invariant manner. Symmetry breaking must occur in the irregular borane hexahedra 300 shown in FIG. 11. In most known boron-rich solids in the prior art, the fivefold icosahedral symmetry is broken by a Jahn-Teller distortion—such that the intericosahedral bonds tend to be stronger than the intraicosahedral bonds. It is for this reason that the boron-rich solids in the prior art are often referred to as inverted molecules. The elimination of fivefold icosahedral symmetry, by an icosahedral symmetry breaking, reduces the spherical aromaticity associated with bond delocalization in boron icosahedra.

It is believed that the fivefold rotational symmetry of the picocrystalline artificial borane atoms 101 (FIG. 9) is maintained, such that the fourfold symmetry of the irregular borane hexahedra 300 is therefore broken. Each irregular borane hexahedron 300 (FIG. 11) is formed by picocrystalline artificial borane atoms 101 at the hexahedral corners. Although a fivefold rotational symmetry cannot be observed by x-ray or electron diffraction, unique electronic and vibrational properties due to the fivefold rotational symmetry of the picocrystalline artificial borane atoms 101 can be observed. Picocrystalline artificial borane atoms 101 comprise a regular arrangement of first- and second-nearest neighbor boron atoms that supports a short-range translational order.

The above-described structure can be more fully understood by considering in more detail the believed structure of one extreme, $(B_{12}H_4)_4Si_4$, of the picocrystalline oxysilaboranes. In $(B_{12}H_4)_4Si_4$, each irregular borane hexahedron 300 forming a solid lattice is ideally constituted by: 8 corner picocrystalline artificial borane atoms 101, 6 face-center picocrystalline artificial borane atoms 101, and 4 natural silicon atoms 303. Due to the sharing of 8 hexahedral corners and the sharing of 2 hexahedral faces, a translation of the irregular borane hexahedra 300 over space ideally results in $(B_{12}H_4)_4Si_4$. In this manner, $(B_{12}H_4)_4Si_4$ forms a picocrystalline polymorph, very similar to monocrystalline silicon, that is comprised of tetravalent natural silicon atoms 303 and tetravalent picocrystalline artificial borane atoms 101.

As shown in FIG. 9, each picocrystalline artificial borane atom 101 constitutes: (1) an artificial nucleus formed by a boron icosahedron comprising 12 natural boron nuclei 102 with a nearly-symmetrical nuclear configuration and (2) 4 artificial valence electrons constituted by 4 natural hydrogen atoms with the hydrogen nuclei 103 bonded to the boron icosahedron such that the 4 hydrogen valence electrons are ideally oriented along a $k\langle_{111}\rangle$ wave vector. In this manner, a picocrystalline artificial borane atom 101 is highly novel since it comprises a boron icosahedron in which all of the 36 of the boron valence electrons occupy intraicosahedral molecular orbitals, such that all intericosahedral chemical bonds are ideally by means of hydrogen valence electrons.

A caged boron icosahedron, with a nearly-symmetrical nuclear configuration and void of any exo-icosahedral bonds due to radial boron orbitals, is not known to exist in the prior art. In a real sense, the artificial nucleus of a picocrystalline artificial borane atom 101 constitutes a caged icosahedral molecule with a higher degree of symmetry than that of the caged truncated icosahedral molecule of buckminsterfullerene. The molecular truncation of buckminsterfullerene eliminates the symmetry operations associated with the fivefold rotation about the 12 icosahedral vertices. The restoration of the fivefold icosahedral rotation in a picocrystalline artificial borane atom 101 results in a greater bond delocalization and, thus also, a greater aromaticity than that of buckminsterfullerene. This is believed to be due to spin-orbit coupling.

As discussed hereinabove, the artificial nucleus of a picocrystalline artificial borane atom 101 constitutes a boron icosahedron with a nearly-symmetrical nuclear configuration which escapes Jahn-Teller distortion. It is believed that polyatomic electronic orbital degeneracies of the boron icosahedron of a picocrystalline artificial borane atom 101 are lifted by spin-orbit coupling, which was not contemplated by Jahn and Teller in their paper "Stability of Polyatomic Molecules in Degenerate Electronic States. I. Orbital Degeneracy," *Proceedings of the Royal Society A*, Vol. 161, 1937, pp. 220-235. The lifting of the polyatomic electronic orbital degeneracies by spin-orbit coupling causes a discrete energy quantization in the artificial nucleus of a picocrystalline artificial borane atom 101 that is subject, in whole or in part, to Dirac's relativistic wave equation.

A discrete energy quantization, subject to Dirac's relativistic wave equation, tends to support a charge-conjugation symmetry between electrons and holes characteristic of graphene and other such low-dimensional materials. It is believed that such a charge-conjugation symmetry is supported in picocrystalline $(B_{12}H_4)_4Si_4$ if the electron-hole pair generation rate is increased by a trace incorporation of a coinage metal, such as natural gold. In the absence of trace impurities, the charge-conjugation symmetry in the artificial nucleus of picocrystalline $(B_{12}H_4)_4Si_4$ is broken such that it behaves as an electron-deficient $B_{12}H_4$ molecule.

It is believed that $B_{12}H_4$ molecules tend to attain a greater stability by means of a disproportionation in which the molecules are simultaneously ionized into pairs of $B_{12}{}^{2-}H_4$ dianions and $B_{12}{}^{2+}H_4$ dications. In one sense, the disproportionation in picocrystalline $(B_{12}H_4)_4Si_4$ is similar to the disproportionation of boron carbide $B_{13}C_2$ into anion and cation pairs. In yet another sense, there exists a fundamental difference between the disproportionation of picocrystalline $(B_{12}H_4)_4Si_4$ and that of carbide $B_{13}C_2$. As is well known in the literature, the icosahedral symmetry in boron carbide is broken by Jahn-Teller distortions. Picocrystalline $(B_{12}H_4)_4Si_4$ escapes said icosahedral symmetry breaking due to a lifting of the polyatomic electronic orbital degeneracies by spin-orbit coupling. This endows picocrystalline $(B_{12}H_4)_4Si_4$ unique chemical properties.

At issue are spectroscopic principles of chemistry. Spectroscopic principles can be described by reference to the book by Harris and Bertolucci, *Symmetry and Spectroscopy*, Oxford Univ. Press, 1978. On pages 1-2, Harris and Bertolucci emphasize an important concept: "Light of infrared frequencies can generally promote molecules from one vibrational energy level into another. Hence, we call infrared spectroscopy vibrational spectroscopy. Visible and ultraviolet light are much more energetic and can promote the redistribution of electrons in a molecule such that the electronic potential energy of the molecule is changed. Hence, we call visible and ultraviolet spectroscopy electronic spectroscopy." This does not account for spin-orbit coupling.

In the presence of a spin-orbit coupling the rotational, vibrational, and electronic degrees of freedom can be intertwined in rovibronic energy levels which support a redistribution of electrons in response to microwave radiation. This phenomenon impacts disproportionation in picocrystalline $(B_{12}H_4)_4Si_4$ due to the belief that the $B_{12}{}^{2-}H_4$ dianions and $B_{12}{}^{2+}H_4$ dications exist in different energy levels separated by an energy difference on the order of 45 micro-electron-volts. In boron carbide $B_{13}C_2$, disproportionation results in anions and cations at the same energy level due to the absence of a spin-orbit coupling. It is for this reason that the preferred compositions of this invention do not contain significant amounts of carbon. Although picocrystalline $(B_{12}H_4)_4Si_4$ ideally supports the maximum disproportionation in picocrystalline oxysilaborane $(B_{12}H_4)_xSi_yO_z$ over the preferred compositional range ($2 \leq x \leq 4$, $3 \leq y \leq 5$ and $0 \leq z \leq 2$), the actual composition with the maximum observed disproportionation appears, based on actual data, to be picocrystalline silaborane $(B_{12}H_4)_3Si_5$.

At the other extreme of the picocrystalline genus $(B_{12}H_4)_xSi_yO_z$ is a picocrystalline species $(B_{12}{}^{2-}H_4)_4Si_4O_2{}^{2+}$ in which there is ideally no disproportionation. In this particular species, natural oxygen atoms are ionized so as to ideally stabilize the artificial nucleus of a picocrystalline artificial borane atom 101 without resort to disproportionation. The chemical nature of the species $(B_{12}H_4)_3Si_5$ and $(B_{12}{}^{2-}H_4)_4Si_4O_2{}^{2+}$ of the genus $(B_{12}H_4)_xSi_yO_z$, over a preferred compositional range ($2 \leq x \leq 4$, $3 \leq y \leq 5$ and $0 \leq z \leq 2$), can be described in terms of the concept of electronegativity introduced by Linus Pauling in *The Nature of the Chemical Bond*, Cornell University Press, Third Edition, 1960, pp. 64-108. Pauling established electronegativity as the measure of the ionicity of any covalent chemical bond. Pauling's concept of electronegativity assumed two-center covalent bonds, which can be carried over to the picocrystalline oxysilaboranes of this invention.

In picocrystalline oxysilaboranes of this invention, picocrystalline artificial borane atoms 101 are covalently bonded to natural atoms or to other picocrystalline artificial borane atoms 101. At one genus extreme, picocrystalline silaborane $(B_{12}H_4)_3Si_5$ exhibits a tendency to capture a pair of electrons and, thus, is said to possess a high electronegativity. At the other genus extreme, picocrystalline oxysilaborane $(B_{12}{}^{2-}H_4)_4Si_4O_2{}^{2+}$ is said to possess a low electronegativity due to an electronic closed-shell configuration. One utility of picocrystalline oxysilaborane $(B_{12}H_4)_xSi_yO_z$ is the ability to vary the electronegativity of various species over the preferred compositional range ($2 \leq x \leq 4$, $3 \leq y \leq 5$ and $0 \leq z \leq 2$) by chemically varying the electronegativity of picocrystalline artificial borane atoms 101. At one compositional extreme, the relatively high electronegativity of picocrystalline silaborane $(B_{12}H_4)_3Si_5$ promotes a disproportionation in the absence of an external source of electrons while, at the other compositional extreme, the relatively low electronegativity of picocrystalline oxysilaborane $(B_{12}{}^{2-}H_4)_4Si_4O_2{}^{2+}$ impedes any disproportionation.

The ability to chemically modulate the electronegativity of picocrystalline artificial borane atoms 101 over a compositional range supports a novel and useful thermochemistry that is not known in the prior art. The chemical modulation of the electronegativity in artificial atoms is made possible by a discrete energy quantization in picocrystalline artificial borane atoms 101 due to spin-orbit coupling. It is by means of spin-orbit coupling that an electron redistribution occurs between microwave energy levels. The intraicosahedral three-center bonds of the artificial nuclei of the picocrystalline artificial borane atoms 101 are much stronger than the intericosahedral two-center covalent bonds of picocrystalline artificial borane atoms 101 to natural atoms or to other picocrystalline artificial borane atoms 101. This is made possible by spin-orbit coupling.

The peak electron density of the three-center bonds of the picocrystalline artificial borane atoms 101 ideally resides in the center of the 8 icosahedral faces normal to the km) wave vectors shown in FIG. 9. The existence of two stable boron isotopes $_5{}^{10}B$ and $_5{}^{11}B$ shifts the peak electron density of the three-center bonds away from the geometric center of the icosahedral faces of artificial nuclei of the picocrystalline artificial borane atoms 101. This shift of the three-center bond away from the geometric center of an icosahedral face increases the entropy of the artificial nucleus of an picocrystalline artificial borane atom 101. In the preferred compositional range of picocrystalline oxysilaborane $(B_{12}H_4)_xSi_yO_z$, entropy is maximized in accordance with the second law of thermodynamics by an isotopic enrichment of boron $_5{}^{10}B$ relative to the natural occurrence.

The naturally-occurring ratio of boron $_5{}^{11}B$ to boron $_5{}^{10}B$ is approximately 4.03. The isotopic enrichment boron $_5{}^{10}B$ relative to boron $_5{}^{11}B$ further shifts the three-center bonds away from the geometric center of the icosahedral faces of the artificial nucleus of a picocrystalline artificial borane atom 101 and, therefore, increases the entropy of the picocrystalline artificial borane atom 101. Such an increase in entropy results in a decrease in Gibbs free energy. The increase in entropy associated with an isotopic enrichment results in a greater decrease in Gibbs free energy than the corresponding decrease in enthalpy, such that an entropic redistribution of electrons is believed to occur between microwave energy levels when spin-orbit coupling maintains nearly-symmetrical boron icosahedra in the picocrystalline oxysilaboranes $(B_{12}H_4)_xSi_yO_z$ of this invention.

By replacing natural atoms with picocrystalline artificial borane atoms 101, atomic engineering can be established in the picocrystalline oxysilaboranes $(B_{12}H_4)_xSi_yO_z$ over a preferred compositional range ($2 \leq x \leq 4$, $3 \leq y \leq 5$ and $0 \leq z \leq 2$). Atomic engineering can be supported by a chemical modification of picocrystalline artificial borane atoms 101 that act as variable atomic elements in novel boron-rich molecules supporting a picotechnology not known in the prior art. Preferred types of picocrystalline oxysilaboranes will be described by actual examples. By means of these examples, the novelty and utility of the picocrystalline oxysilaboranes $(B_{12}H_4)_xSi_yO_z$ over a preferred compositional range ($2 \leq x \leq 4$, $3 \leq y \leq 5$ and $0 \leq z \leq 2$) can be better understood.

A method for making the oxysilaborane films of the present invention is a chemical vapor deposition causing the precipitation of a solid film by passing gas vapors containing boron, hydrogen, silicon, and oxygen over a heated substrate in a sealed chamber maintained at a pressure below that of the atmosphere. The preferred vapors are nitrous oxide $N_2O$ and the lower-order hydrides of boron and silicon, with diborane $B_2H_6$ and monosilane $SiH_4$ being the most preferred. Both hydrides can be diluted in a hydrogen carrier gas. By passing hydrogen-diluted diborane and monosilane, and optionally nitrous oxide, over a sample heated above ~200° C. at a pressure of ~1-30 torr, a solid oxysilaborane film self-assembles over the substrate under preferred conditions.

The heating can be realized with equipment generally known to those skilled in the art of semiconductor processing. A molybdenum susceptor, by way of an example, can provide a solid substrate carrier that can be resistively or inductively heated. The substrate can be heated without any susceptor in a resistively-heated quartz tube. In these methods, there can exist heated surfaces (other than the intended deposition substrate) on which an oxysilaborane film is deposited. The substrate can be heated without a susceptor in a cold-wall reactor by radiative heat by halogen lamps in a low-pressure rapid thermal chemical vapor deposition that minimizes reactor outgassing from heated surfaces coated by prior depositions.

Whenever the deposition temperature exceeds ~350° C. hydrogenation effects are substantially eliminated. Conversely, by reducing the deposition temperature below ~350° C. a thin picocrystalline solid can become significantly hydrogenated, such that hydrogen can be actively incorporated in chemical bonds. The relative atomic concentration of hydrogen in a picocrystalline oxysilaborane solid deposited below ~350° C. is usually within the range of 10-25% depending on the degree of oxygen incorporation. When hydrogen is not actively incorporated in the chemical bonds of an oxysilaborane solid, it is more particularly referred to as an oxysilaboride solid. An oxysilaborane solid substantially void of oxygen is specifically referred to as a silaborane solid.

Oxygen can be incorporated into a picocrystalline oxysilaborane solid by either individual oxygen atoms or as part of water molecules. A picocrystalline oxysilaborane solid that contains water molecules is said to be hydrous while a picocrystalline oxysilaborane solid formed by individual hydrogen and oxygen atoms, with a relatively negligible amount of water, is said to be anhydrous. It has been observed that hydrous picocrystalline oxysilaborane solids undergo a change in color and stoichiometry over time due, apparently, to the change in the trapped water. Unless explicitly stated otherwise, picocrystalline oxysilaborane solids in embodiments described hereinbelow are understood to be anhydrous. In order to minimize hydration, a deposition reactor is fitted with a load-lock chamber isolating the reaction chamber from a direct exposure to ambient moisture. However, adsorbed moisture is difficult to fully eliminate during sample loading.

In addition to color changes, hydration can alter the boron-to-silicon ratio. In one preferred embodiment of oxysilaborane, the boron-to-silicon ratio is ideally six. An incorporation of atomic oxygen without hydration in oxysilaborane reduces the boron-to-silicon ratio while the incorporation of water molecules into hydrous oxysilaborane tends to increase the boron-to-silicon ratio. Both such effects can exist concurrently. A preferred introduction of oxygen into anhydrous oxysilaborane is by means of nitrous oxide. The relative atomic concentration of boron atoms in oxysilaborane amongst boron, silicon, and oxygen atoms is ideally ~83%. In the absence of any hydration effects, the relative atomic concentration of boron amongst boron, silicon, and oxygen atoms does not significantly exceed ~89%. The susceptibility to hydration depends, in part, on the relative oxygen atomic concentration and the method by which oxygen is introduced.

Self-assembled picocrystalline oxysilaborane has characteristics that are useful in electronic integrated circuits using covalent semiconductors, such as monocrystalline silicon. The electronic properties of an oxysilaborane solid can be altered in a controlled manner by processing conditions during the vapor-phase deposition. Picocrystalline oxysilaborane exhibits a long-range bond-orientational order. X-ray photoelectron spectroscopy (XPS) established the binding energy of the boron 1s electron in picocrystalline oxysilaborane as ~188 eV, which is characteristic of chemical bonds in an icosahedral boron molecule. The oxygen 1s electron binding energy, ~532 eV, is quite similar to that of the oxygen 1s electron binding energy in a metallic oxide, which is different from that of the oxygen 1s electron in a glass.

The silicon 2p electron binding energy in the oxysilaborane solids of this invention exhibits a sharp energy peak of 99.6 eV over the full compositional range. This is important for several reasons. First of all, the absence of two energy peaks in oxysilaborane implies that the Si—Si and Si—H bonds possess an identical binding energy. Secondly, the measured binding energy of a silicon 2p electron in oxysilaborane is essentially that of monocrystalline silicon constituted by tetrahedral chemical bonds in the diamond lattice. The silicon 2p electron binding energy in silicon dioxide is 103.2 eV. When oxysilaborane is deposited on amorphous silicon dioxide, there exists a distinct difference in the silicon 2p electron binding energy in the two compositions. The silicon 2p electron binding energy in oxysilaborane is similar to that of monocrystalline silicon, despite being deposited on an amorphous oxide, due to a self-assembly of picocrystalline oxysilaboranes.

By appropriately controlling the chemical vapor deposition processing conditions, picocrystalline oxysilaborane $(B_{12}H_4)_xSi_yO_z$ self-assembles over the preferred compositional range ($2 \leq x \leq 4$, $3 \leq y \leq 5$ and $0 \leq z \leq 2$) that is bounded by picocrystalline silaborane $(B_{12}H_4)_3Si_5$ at one compositional extreme and by picocrystalline oxysilaborane $(B_{12}{}^{2-}H_4)_4Si_4O_2{}^{2+}$ at the opposite such compositional extreme. In order to more fully understand the preferred processing conditions, the processing of non-preferred species in the broader range ($0 \leq w \leq 5$, $2 \leq x \leq 4$, $2 \leq y \leq 5$, $0 \leq z \leq 3$) of oxysilaborane $(B_{12})_xSi_yO_zH_w$ will be taught by a number of examples.

Now, various embodiments of oxysilaborane compositions according to the present invention are described by examples, but the scope of the invention is not limited thereto. As will be understood by those skilled in the art, this invention may be embodied in other forms without a departure from the spirit or essential characteristics thereof. The disclosure and descriptions herein below are intended to be illustrative, but not limiting, of the scope of the invention.

Example 1

Phosphorous was diffused into the 100 mm diameter monocrystalline (001) p-type silicon substrate 404 (FIG. 12) with a resistivity of 15 $\Omega$-cm so as to result in an 8.7 ohm per square resistance, as measured by a four-point probe. The oxide was removed from the sample wafer by a hydrofluoric acid deglaze. The sample was the introduced into a rapid thermal chemical vapor deposition (RTCVD) chamber of the type described by Gyurcsik et al. in "A Model for Rapid Thermal Processing," *IEEE Transactions on Semiconductor Manufacturing*, Vol. 4, No. 1, 1991, p. 9. After loading the sample wafer onto a quartz ring, the RTCVD chamber was then closed and mechanically pumped down to a pressure of 10 mtorr. A 3% mixture, by volume, of diborane in hydrogen $B_2H_6(3\%)/H_2(97\%)$ at a flow rate of 364 sccm and a 7% mixture, by volume, of silane in hydrogen $SiH_4(7\%)/H_2(93\%)$ at a flow rate of 390 sccm were introduced into the chamber.

Figure 12:
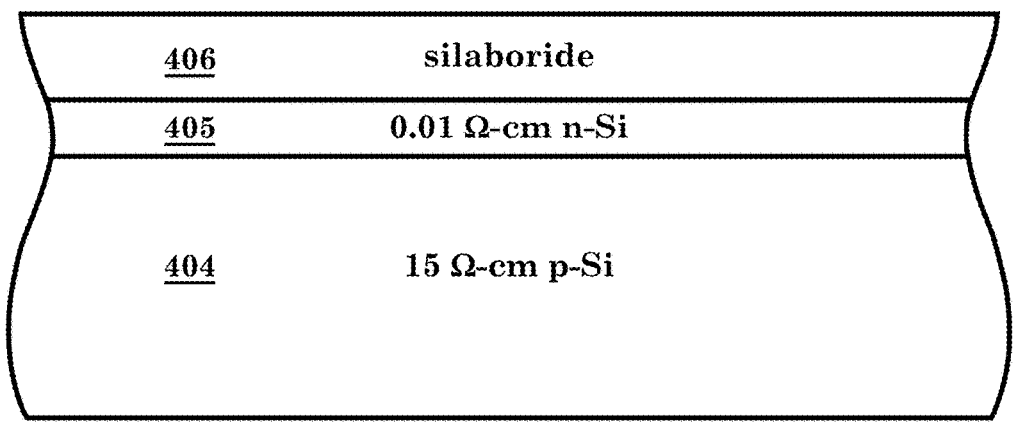
FIG. 12 is an illustration of a silaboride film deposited over a donor-doped region.

The reactant gas flow rate was stabilized at a pressure of 3.29 torr, whereupon the tungsten-halogen lamps were turned on for 30 seconds and regulated so as to maintain the sample wafer at 605° C. As shown in FIG. 12, a thin silaboride solid 406 was deposited over the donor-doped region 405. The composition of the silaboride solid 406 was investigated by means of x-ray photoelectron spectroscopy (XPS). The binding energy of the boron 1s electron was measured as being 187.7 eV, which is consistent with icosahedral boron. The binding energy of the silicon 2p electron was determined to be 99.46 eV, which is characteristic of monocrystalline (001) silicon. An XPS depth profile of the silaboride solid 406 measured the relative atomic concentrations of boron and silicon within the silaboride solid 406 as being 86% and 14% respectively. Rutherford backscattering spectroscopy (RBS) determined the relative atomic concentrations of boron and silicon in the thin silaboride solid 406 as being 83.5% and 16.5% respectively.

The relative hydrogen concentration in the thin silaboride solid 406 was measured by means of hydrogen forward scattering (HFS), in which hydrogen atoms are elastically scattered by incident high-energy helium atoms. Hydrogen forward scattering (HFS) is not as quantitative as the Rutherford backscattering spectroscopy (RBS), due to the oblique angle of incident helium atoms that causes a variation in the charge integration in various samples. Although the hydrogen counts per unit solid angle are constant, the solid angle itself can change between different samples. No hydrogen was detected. A solid comprised of boron and silicon in the absence of hydrogen is referred to as a silaboride composition.

Figure 13:
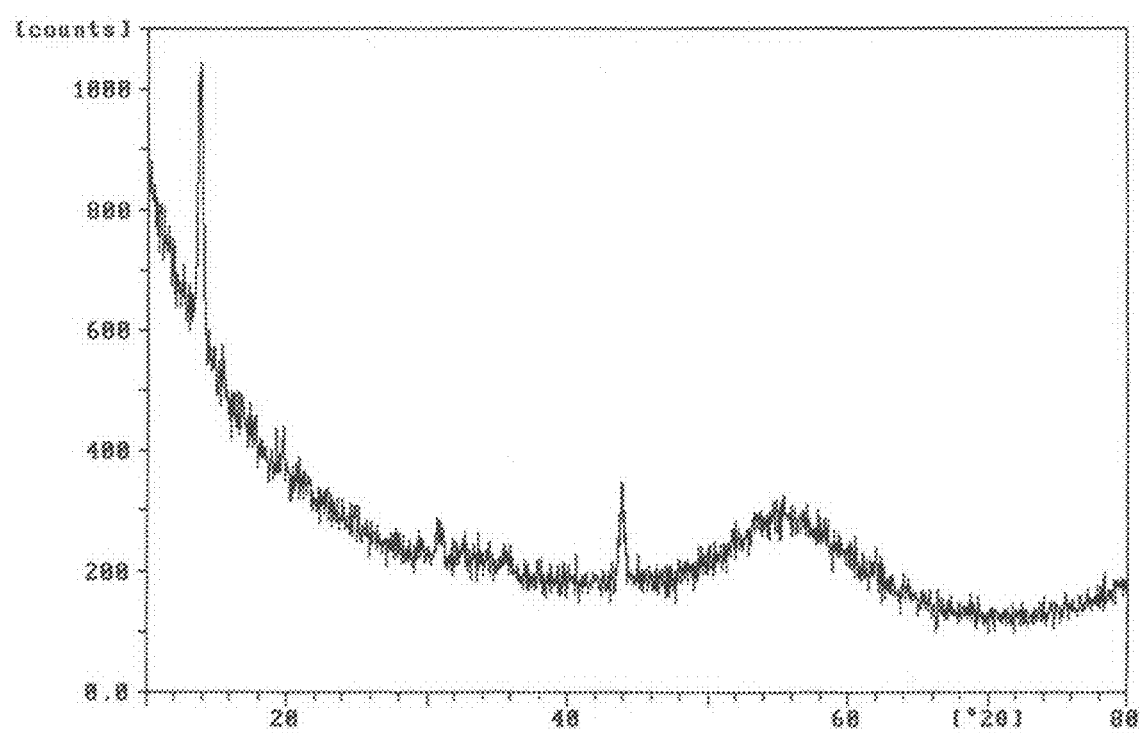
FIG. 13 is a graph of a GIXRD scan of the picocrystalline silaboride solid of Example 1.

A secondary ion mass spectroscopy (SIMS) analysis determined the $_5{}^{11}B/_5{}^{10}B$ ratio of the silaboride solid 406 as the naturally-occurring ratio 4.03. The absence of any hydrogen or isotopic enrichment in the silaboride solid 406 of this example is due to the deposition temperature. A hydrogenation of silaborane can be realized when the deposition temperature is below ~350° C. or when oxygen is introduced, as will be discussed in examples herein below. The silaboride solid 406 of this example was established by x-ray diffraction to be a picocrystalline boron solid. A GIXRD scan of the picocrystalline silaboride solid 406 of this example is shown in FIG. 13. The diffraction peak at $2\theta=14.50$ corresponds to the Bragg condition associated with the x-ray angle of incidence $\omega=7.25°$ of the GIXRD scan.

Example 2

Figure 14:
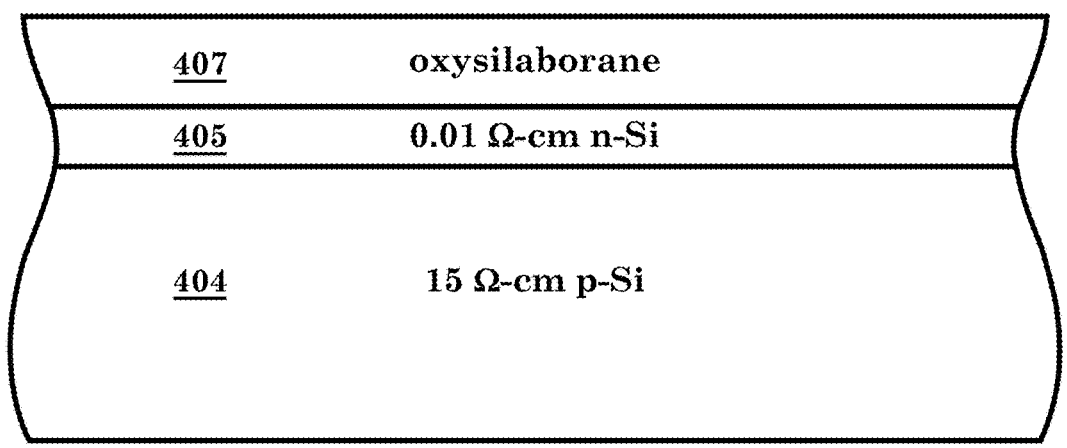
FIG. 14 is an illustration of an oxysilaborane film deposited over a donor-doped silicon region in accordance with Example 2.

The procedure described in Example 1 was carried out with the two exceptions that undiluted nitrous oxide $N_2O$ was introduced at 704 sccm and the flow rates of the hydride gases were doubled. A 3% mixture by volume of diborane in hydrogen $B_2H_6(3\%)/H_2(97\%)$ at a flow rate of 728 sccm, a 7% mixture by volume of monosilane in hydrogen $SiH_4(7\%)/H_2(93\%)$ at a flow rate of 780 sccm, and undiluted nitrous oxide $N_2O$ at a flow rate of 704 sccm were introduced. The vapor flow rate was stabilized at 9.54 torr, whereupon the tungsten-halogen lamps were turned on for 30 seconds, and regulated, in order to maintain the sample substrate 404 at 605° C. As shown in FIG. 14, the oxysilaborane solid 407 was deposited on the donor-doped silicon region 405. The composition of the thin oxysilaborane solid 407 was evaluated by x-ray diffraction spectroscopy.

Figure 15:
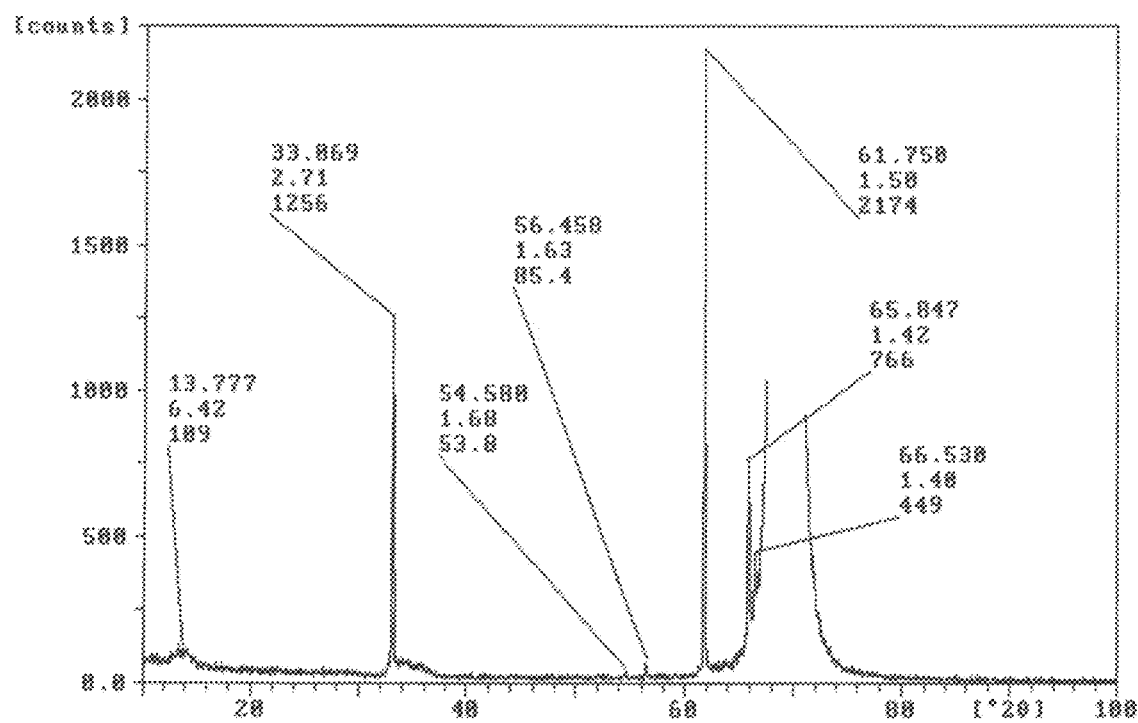
FIG. 15 is a graph of a conventional ω-2θ XRD scan of the thin oxysilaborane solid of Example 2.
Figure 16:
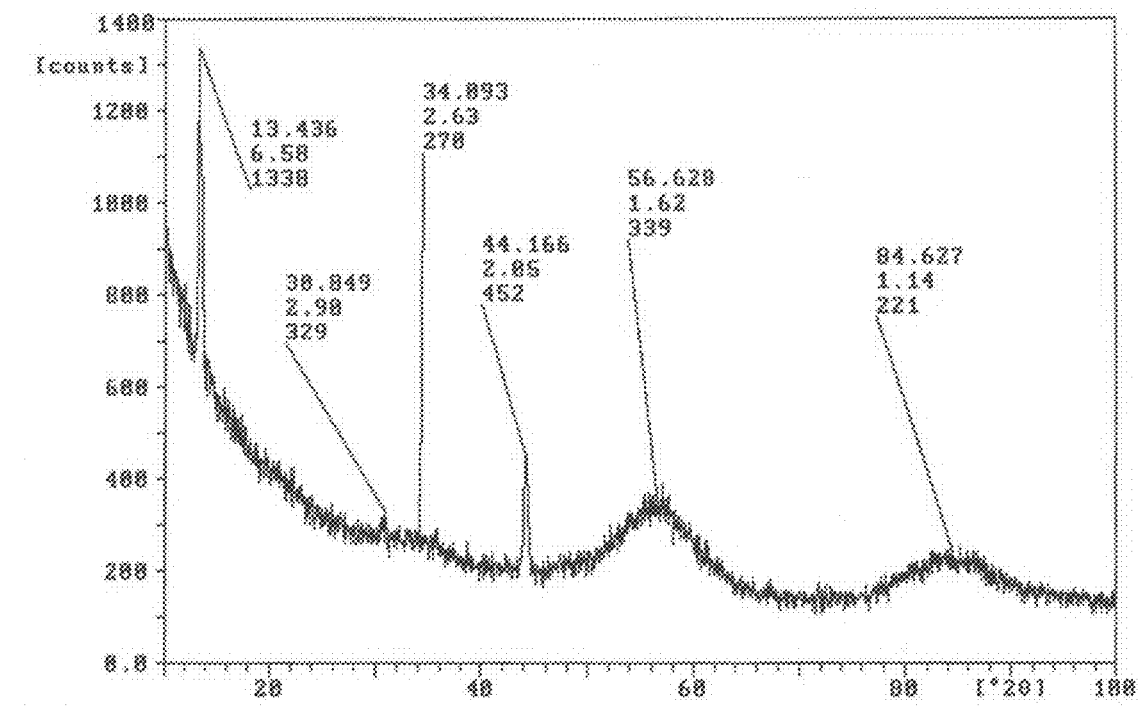
FIG. 16 is a graph of a GIXRD scan of the thin oxysilaborane solid of Example 2.

A conventional $\omega$-$2\theta$ XRD scan of the thin oxysilaborane solid 407 is shown in FIG. 15. The broadened diffraction peaks near $2\theta=13.78°$ and $2\theta=33.07°$ are characteristic of a picocrystalline boron solid. This is further corroborated by the GIXRD scan in FIG. 16, in which a diffraction peak at $2\theta=13.43°$ corresponds to the Bragg condition associated with the x-ray angle of incidence $\omega=6.70°$. The composition of the oxysilaborane solid 407 was established by XPS spectroscopy. The binding energy of the boron 1s electron was 187.7 eV and the binding energy of the silicon 2p electron was 99.46 eV, which are the same as Example 1. The binding energy of the oxygen is electron was 524 eV. As measured by XPS, the relative bulk atomic concentrations of boron, silicon, and oxygen were 81%, 12%, and 7%.

By Rutherford backscattering spectroscopy (RBS) and hydrogen forward scattering (HFS) the relative bulk atomic concentrations of boron, hydrogen, silicon, and oxygen within the oxysilaborane solid 407 of this example were respectively determined as: 72%, 5.6%, 13.4%, and 9.0%. The picocrystalline boron solid 407 of the present example is not a borane solid but, rather, is much better characterized as an oxygen-rich composition $(B_{12})_2Si_{3.5}O_{2.5}H$ in which the hydrogen atoms are, most probably, bonded to the oxygen atoms. Secondary ion mass spectroscopy (SIMS) established the isotopic ratio $_5{}^{11}B/_5{}^{10}B$ as being the naturally-occurring ratio of the boron isotopes, to within the experimental error. It is currently believed that the existence of a naturally-occurring isotopic ratio in $_5{}^{11}B/_5{}^{10}B$ is indicative of the absence of intertwined rovibronic energy levels that are capable of promoting the redistribution of electrons between microwave energy levels.

Example 3

The pyrolysis of boron and silicon hydrides was carried out by a low-pressure chemical vapor deposition (LPCVD) within a horizontal resistively-heated reactor comprising a five-inch diameter quartz deposition tube, which was constrained on a table. The resistive heating element was mounted upon a motorized track, such that 75 mm silicon substrates could be loaded onto a quartz holder in the front of the tube at room temperature. Water vapor adsorbed onto the quartz walls during sample loading provided a source of water vapor for the subsequent chemical reaction. A 75 mm diameter monocrystalline (001) n-type silicon substrate 408 of a resistivity of 20 Ω-cm was loaded onto a quartz holder in the quartz tube, which was sealed and mechanically pumped down to a base pressure of 30 mtorr.

Figure 17:
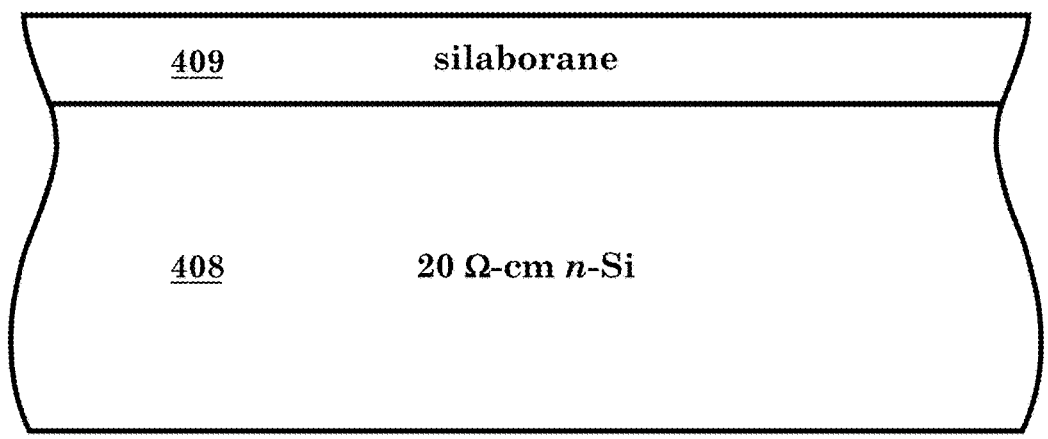
FIG. 17 is an illustration of a silaborane film deposited on a n-type silicon substrate in accordance with Example 3.

As shown in FIG. 17, a boron-rich solid 409 was deposited on the (001) substrate 408 by introducing a 3% mixture, by volume, of diborane in hydrogen $B_2H_6(3\%)/H_2(97\%)$ at the flow rate of 180 sccm and a 10% mixture, by volume, of silane in hydrogen $SiH_4(10\%)/H_2(90\%)$ at a flow rate of 120 sccm. The gas flow rates stabilized at a deposition pressure of 360 mtorr. The motorized heating element was transferred over the sample. The deposition temperature stabilized at 230° C. after a ~20 minute temperature ramp due to the thermal mass of the quartz tube and the quartz sample holder. The pyrolysis was sustained for 8 minutes at 230° C., whereupon the heating element was retracted and the reactive gases were secured. The relative atomic concentrations of boron and silicon in the silaborane solid 409 were measured by different types of spectroscopy.

Figure 18:
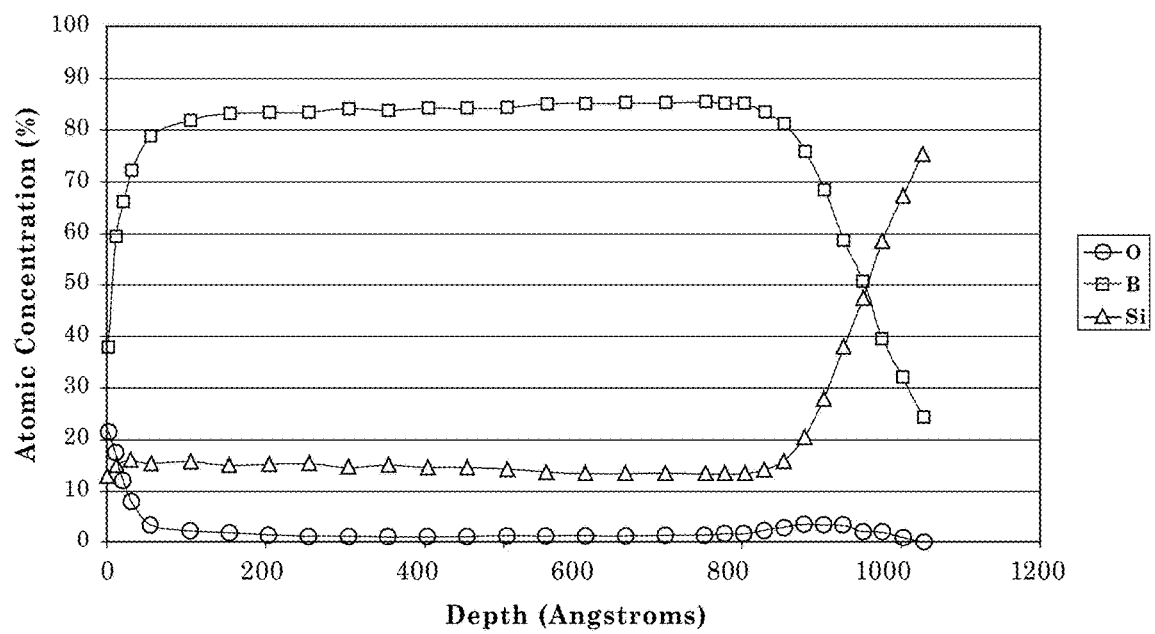
FIG. 18 is an x-ray photoelectron spectroscopy (XPS) depth profile of the silaborane film as deposited in Example 3.

An x-ray photoelectron spectroscopy (XPS) depth profile of the silaborane solid 409 was performed. The oxygen in the silaborane solid 409 is due to an outgassing of water vapor from the quartz walls. The XPS depth profile in FIG. 18 shows the relative atomic concentration of boron, silicon and oxygen in the silaborane solid 409 as being respectively: 85%, 14%, and 1%. The binding energy of the boron 1s electron was 187 eV, which is characteristic of the bonds in icosahedral boron molecules. The XPS binding energy of the silicon 2p electron was 99.6 eV, which is characteristic of the silicon 2p electron in (001) monocrystalline silicon. The XPS binding energy of the oxygen 1s electron was measured as 532 eV. A depth analysis of the silaborane film 409 by Rutherford backscattering spectroscopy (RBS) measured the relative atomic concentrations of boron and silicon as being 82.6% and 17.4% respectively.

Figure 19:
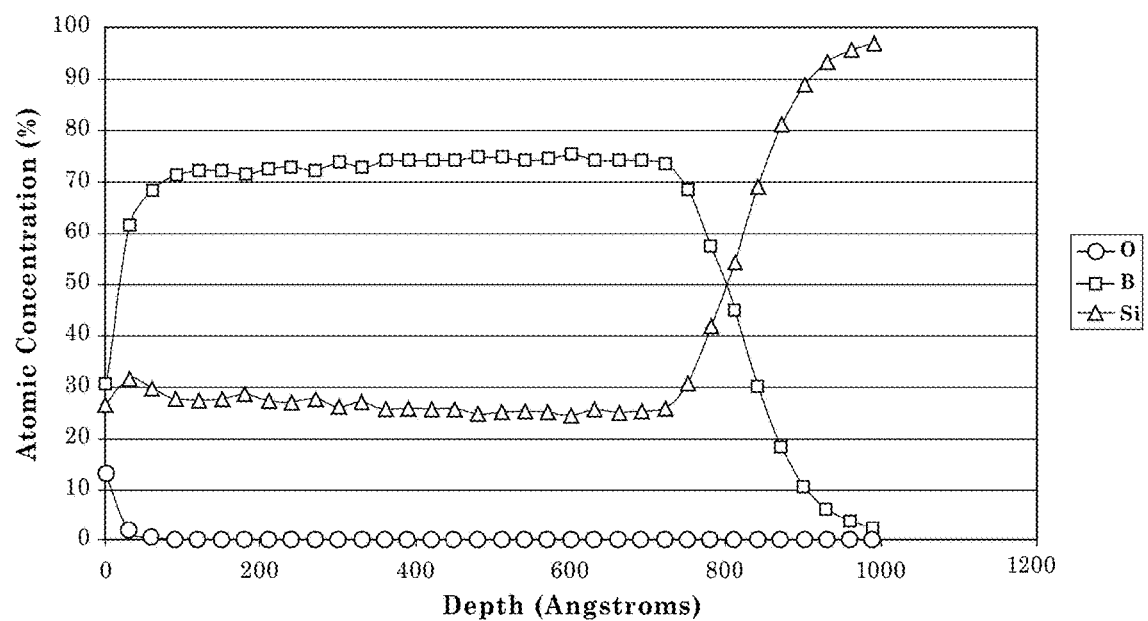
FIG. 19 is an Auger electron spectroscopy (AES) depth profile of the silaborane film as deposited in Example 3.

The Auger electron spectroscopy (AES) depth profile in FIG. 19 shows the relative atomic concentrations of boron, silicon, and oxygen in the solid 409 as being respectively: 73.9%, 26.1% and 0.1%. The thickness of the solid 409 was established by XPS, AES, and RBS as 998 Å, 826 Å, and 380 Å. The relative bulk atomic concentrations of boron, hydrogen and silicon were all established by RBS/HFS depth profiles of the silaborane solid 409 of this example as: 66.5%, 19.5%, and 14.0%. A secondary ion mass spectroscopy (SIMS) depth profile was carried out in order to establish the existence of any isotopic enrichment. An isotopic enrichment of boron $_5^{10}B$ was proven by the SIMS depth profile. Whereas the naturally-occurring $_5^{11}B/_5^{10}B$ ratio is 4.03, the SIMS analysis measured the $_5^{11}B/_5^{10}B$ ratio in the silaborane solid 409 as being 3.81.

The film in Example 3 is referred to as a silaborane solid 409 since the small relative atomic concentration of oxygen is believed to be in the form of water. As a result, this film is better referred to as a hydrous silaborane solid 409. The conventional ω-2θ XRD diffraction pattern in FIG. 6 and the GIXRD diffraction pattern in FIG. 8 were both obtained from the hydrous silaborane solid 409 in Example 3. As the result, the hydrous silaborane solid 409 is a picocrystalline boron solid. Although the conventional ω-2θ XRD diffraction pattern in FIG. 6 of the hydrous silaborane solid 409 of FIG. 14 is substantially the same as the diffraction pattern in FIG. 15 of oxysilaborane solid 407 in FIG. 14, the two picocrystalline boron solids are fundamentally distinguished by the isotopic enrichment of boron $_5^{10}B$ relative to boron $_5^{11}B$. This distinction impacts embodiments of this invention. Specifically, the picocrystalline boron solid 407 of FIG. 14 deposited at a higher temperature had the natural ratio of $_5^{11}B/_5^{10}B$, whereas hydrous silaborane 409 in FIG. 17 deposited at a lower temperature was isotopically enriched with more $_5^{10}B$ than is naturally present.

Example 4

Figure 20:
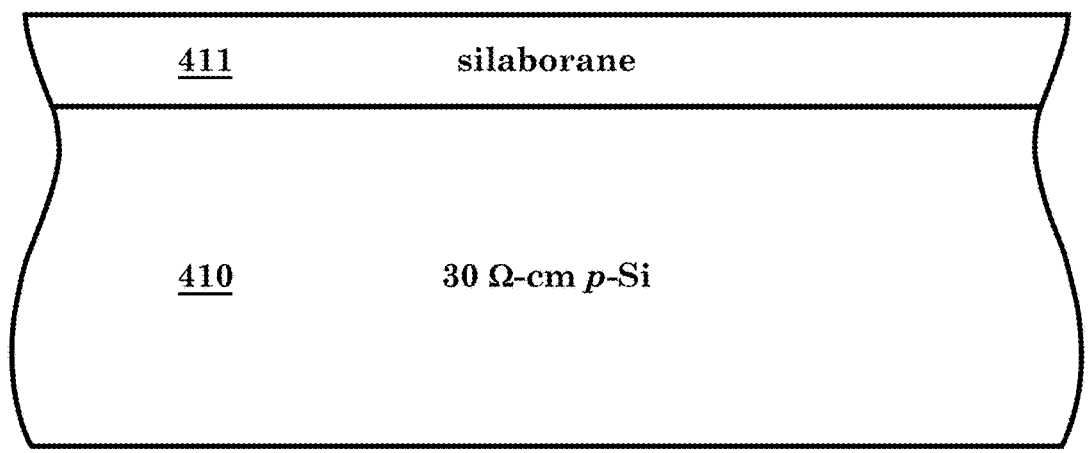
FIG. 20 is an illustration of a silaborane film deposited on a p-type silicon substrate in accordance with Example 4.

Referring now to FIG. 20, a 100 mm diameter monocrystalline (001) p-type silicon substrate 410 with a resistivity of 30 Ω-cm was introduced onto a resistively-heated molybdenum susceptor in an EMCORE D-125 MOCVD reactor by a load-lock system that isolated the sample deposition chamber from the ambient. The chamber was pumped below 50 mtorr, whereupon a 3% mixture, by volume, of diborane in hydrogen $B_2H_6(3\%)/H_2(97\%)$ at the flow rate of 360 sccm and a 7% mixture, by volume, of monosilane in hydrogen $SiH_4(7\%)/H_2(93\%)$ at the flow rate of 1300 sccm were introduced into the chamber, after which the reactant gases were permitted to mix. Upon the stabilization of the gas flow rate, the chamber pressure was regulated at 9 torr and the molybdenum susceptor was rotated at 1100 rpm.

Figure 21:
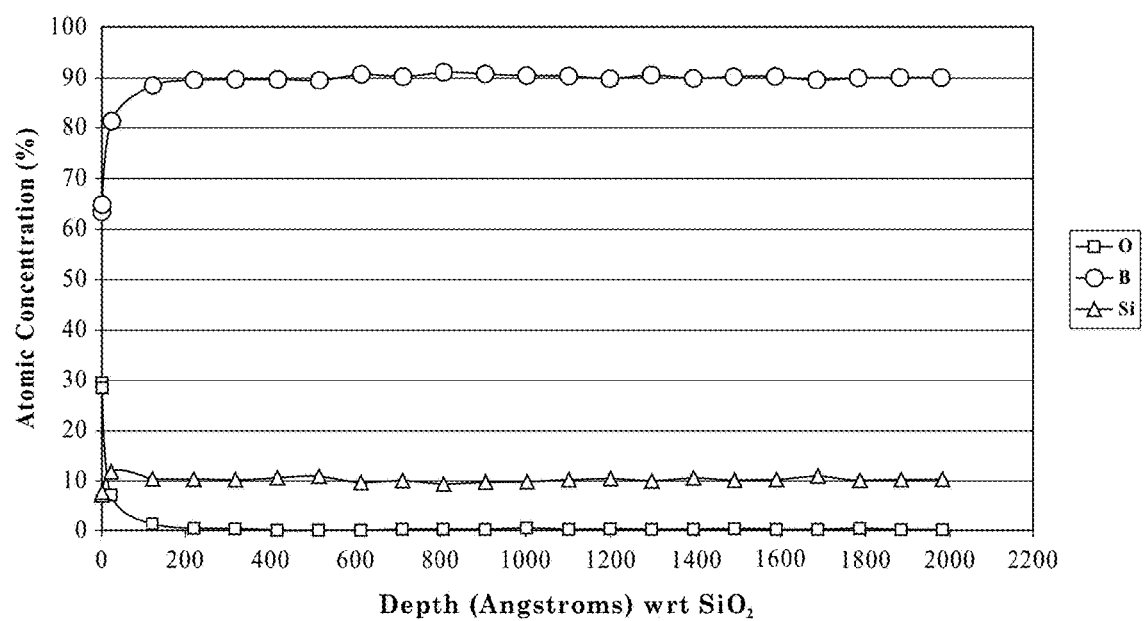
FIG. 21 is an x-ray photoelectron spectroscopy (XPS) depth profile of the silaborane film as deposited in Example 4.

The substrate temperature was increased to 280° C. by a resistively-heated rotating susceptor. Upon stabilization at the deposition temperature of 280° C., the chemical reaction was allowed to proceed for 5 minutes, whereupon susceptor heating was arrested and the sample was allowed to cool to below 80° C. before removing it from the deposition chamber. A thin solid 411 with a polymeric semitransparent color was deposited upon the substrate 410, as shown in FIG. 20. The solid 411 thickness was measured by variable-angle spectroscopic ellipsometry to be 166 nm. The silaborane solid 411 was smooth with no signs of a grain structure. The silaborane solid 411 did not exhibit visible hydration effects. The XPS depth profile in FIG. 21 established the relative atomic concentrations of boron and silicon in the bulk solid 411 as being 89% and 10%.

Figure 22:
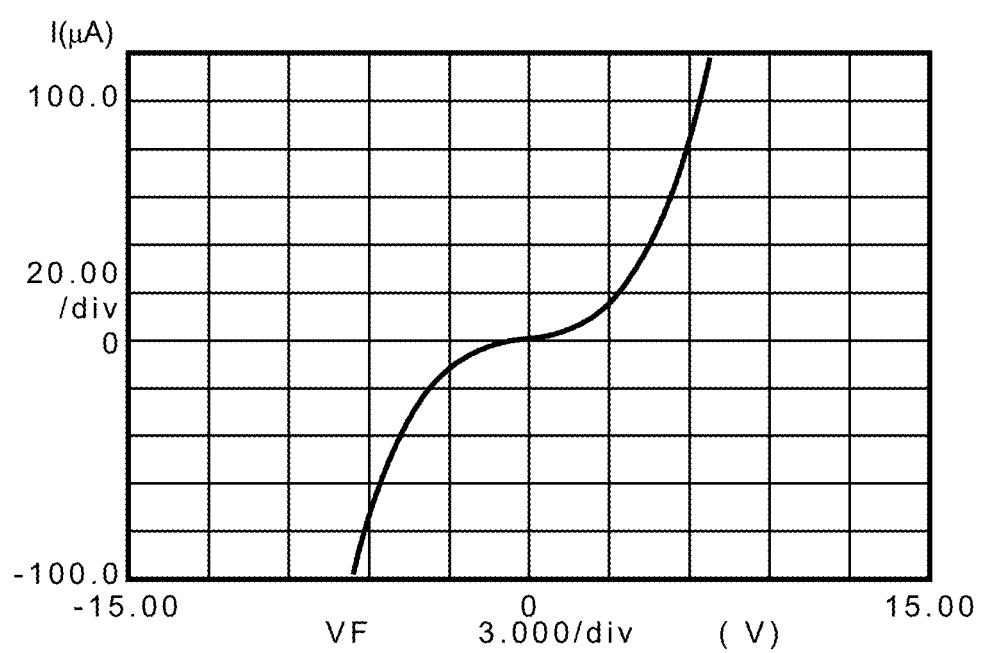
FIG. 22 is a linear graph of the current-voltage characteristics of the silaborane film deposited in accordance with Example 4, as measured by an HP-4145 parameter analyzer with the sweep signals obtained by a mercury probe.
Figure 23:
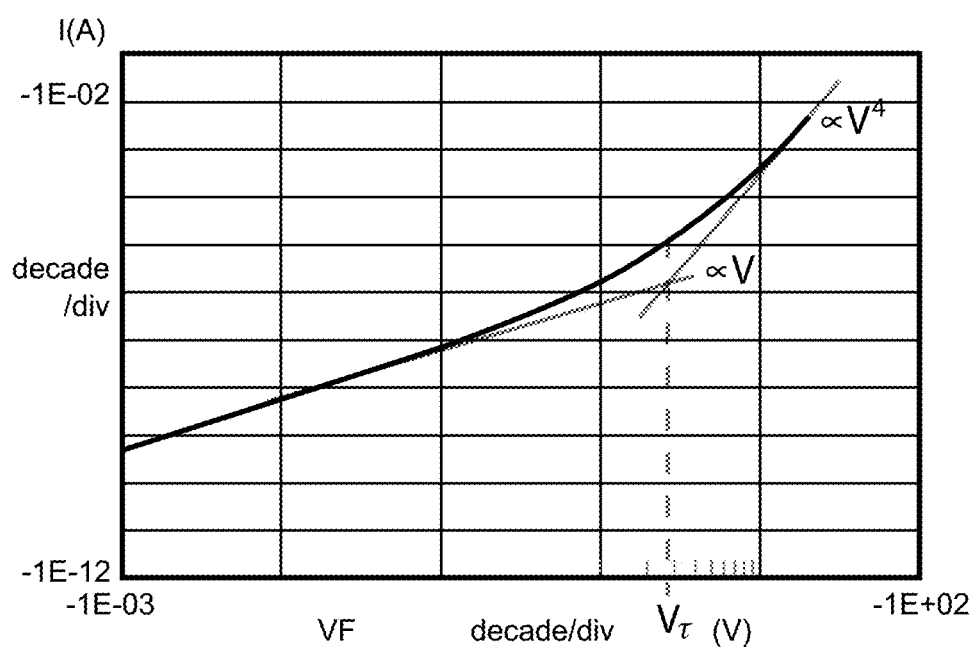
FIG. 23 is a log-log graph of the current-voltage characteristics of the silaborane film deposited as in accordance with Example 4, as measured by an HP-4145 parameter analyzer with the sweep signals obtained by a mercury probe.

RBS and HFS analysis established the relative atomic concentrations of boron, hydrogen, and silicon as being: 66%, 22%, and 11%. The silaborane solid 411 of this example is very similar to the silaborane solid 409 in Example 3, except that the silaborane solid 411 of this example did not exhibit noticeable hydration effects. Electrical characteristics of the silaborane solid 411 were measured by an HP-4145 parameter analyzer, with the sweep signals by a mercury probe. Linear and log-log graphs of the current-voltage characteristics of the silaborane solid 411 are shown in FIGS. 22-23. The nonlinear current-voltage characteristics of the silaborane solid 411 are due to a space-charge-limited conduction current which deviates from Ohm's law beyond an onset of relaxation in accordance with FIG. 23.

Space-charge-limited current conduction in a solid was first proposed by Mott and Gurney, *Electronic Processes in*

*Ionic Crystals*, Oxford University Press, second edition, 1948, pp. 168-173. In analogy to Child's law of vacuum-tube devices, Mott and Gurney developed that a space-charge-limited current density between electrodes, intervened by a dielectric, quadratically varies with an impressed electromotive force. The Mott-Gurney law is satisfied when a unipolar excess mobile charge exists due to a nonvanishing divergence of the electric field per Gauss' law. The conduction current in the picocrystalline oxysilaboranes is space-charge-limited.

Example 5

Figure 24:
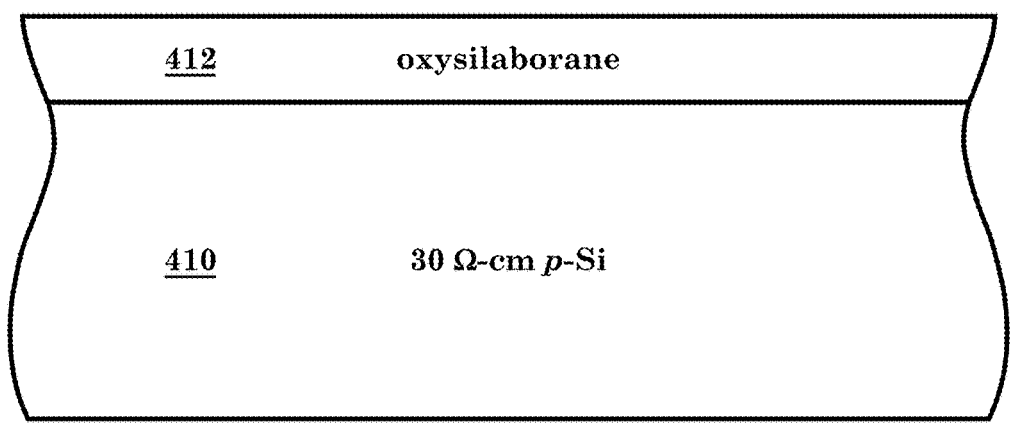
FIG. 24 is an illustration of an oxysilaborane film deposited on a p-type silicon substrate in accordance with Example 5.
Figure 25:
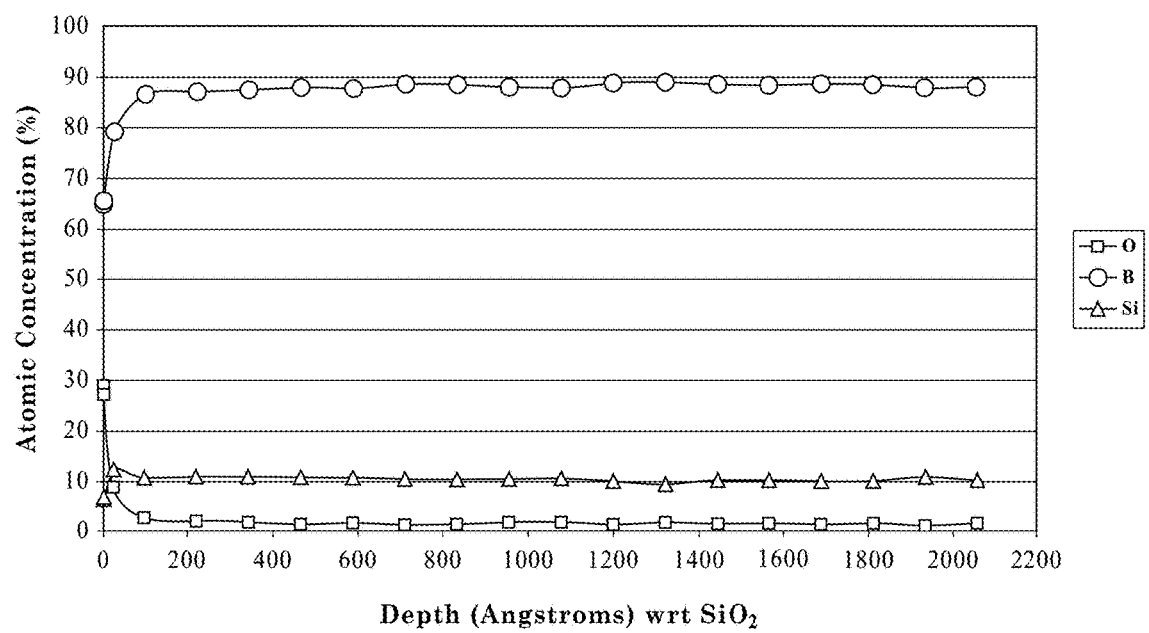
FIG. 25 is an x-ray photoelectron spectroscopy (XPS) depth profile of the oxysilaborane film as deposited in Example 5.

The procedure described in Example 4 was carried out with the sole exception that nitrous oxide was introduced at a flow rate of 40 sccm. As shown in FIG. 24, a thin oxysilaborane solid 412 with a polymeric semitransparent color was deposited over the (001) monocrystalline p-type silicon substrate 410. The solid 412 thickness was measured by variable-angle spectroscopic ellipsometry as being 159 nm. The XPS depth profile in FIG. 25 established the relative atomic concentrations of boron, silicon, and oxygen in the bulk oxysilaborane solid 412 as respectively being: 88.0%, 10.4%, and 1.6%. The incorporation of oxygen altered the oxysilaborane solid 412 of this example relative to the silaborane solid 411 of Example 4.

Figure 26:
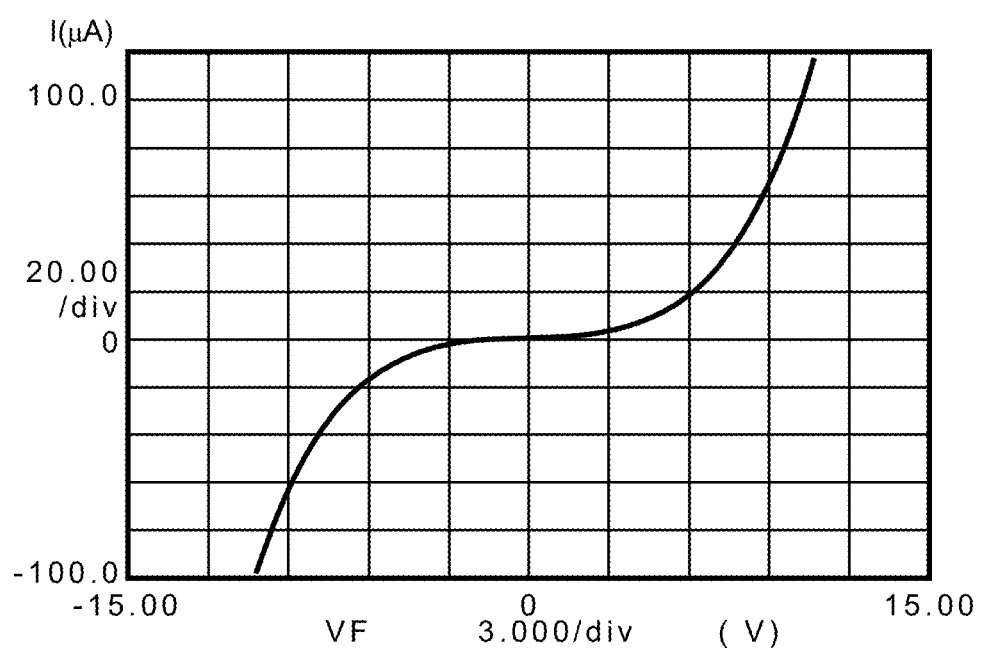
FIG. 26 is a linear graph of the current-voltage characteristics of the oxysilaborane film deposited as in Example 5, as measured by an HP-4145 parameter analyzer with the sweep signals obtained by a mercury probe.
Figure 27:
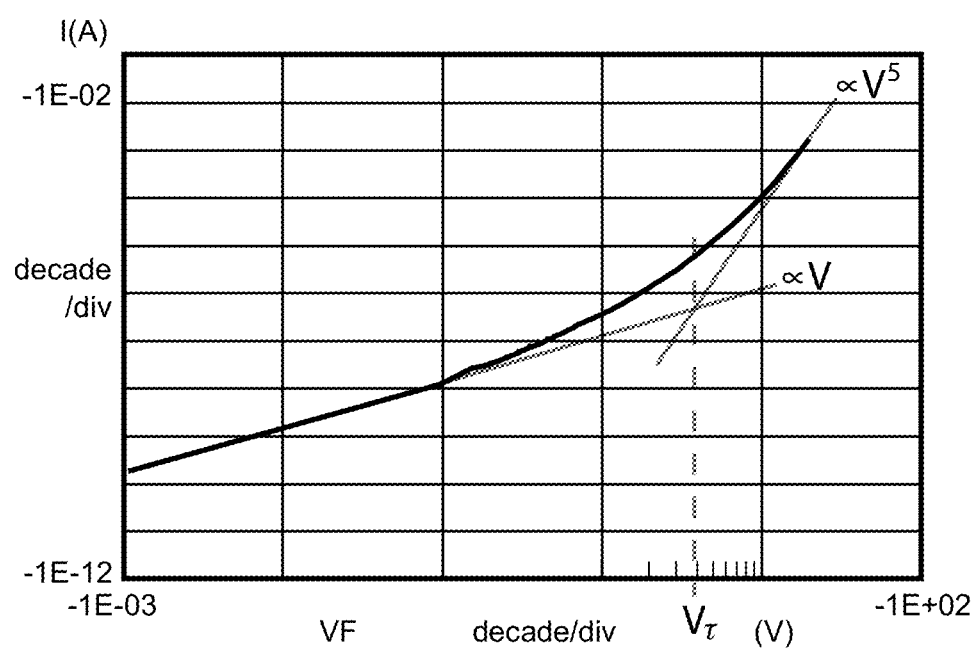
FIG. 27 is a log-log graph of the current-voltage characteristics of the oxysilaborane film deposited as in Example 5, as measured by an HP-4145 parameter analyzer with the sweep signals obtained by a mercury probe.

The electrical impedance of the oxysilaborane solid 412 of the present example was measured by an HP-4145 parameter analyzer, with the sweep signals provided by a mercury probe. Linear and log-log graphs of the impedance characteristics of the oxysilaborane solid 412 of this example are respectively shown in FIGS. 26-27. The impedance of the oxysilaborane solid 412 of the present example increased relative to the silaborane solid 411 in Example 4. The space-charge-limited current in the oxysilaborane solid 412 of this present example saturated at a quintic current-voltage characteristic, as shown FIG. 27. The space-charge current is limited by charge drift.

Example 6

Figure 28:
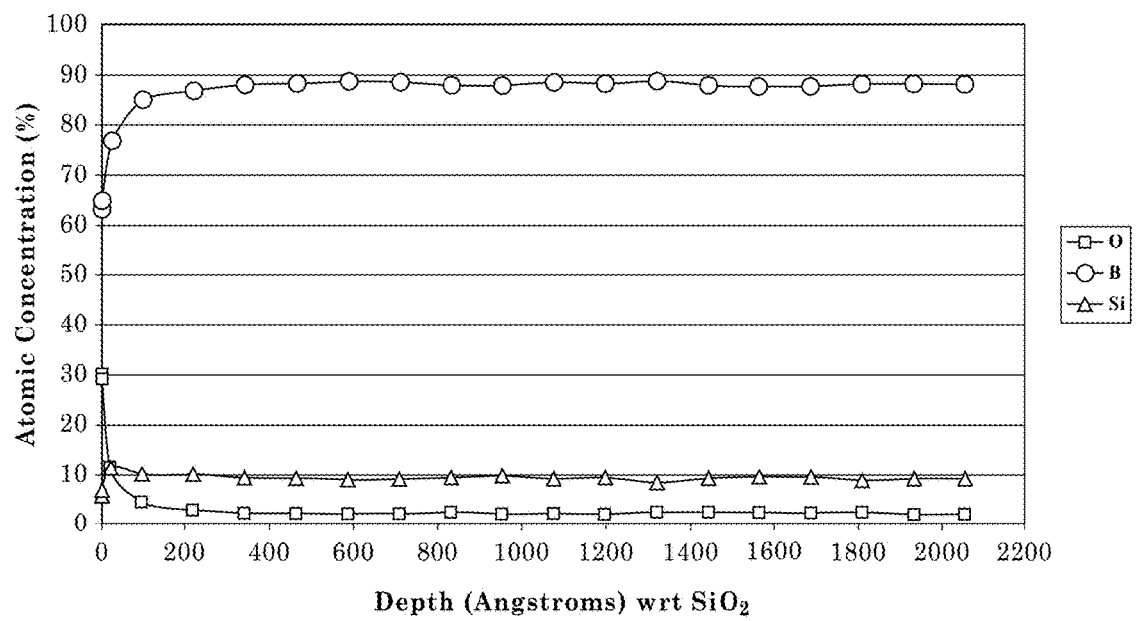
FIG. 28 is an x-ray photoelectron spectroscopy (XPS) depth profile of the oxysilaborane film as deposited in Example 6.

The procedure described in Example 5 was carried out with a single exception that the flow rate of the nitrous oxide was increased from 40 sccm to 80 sccm. The thickness of the oxysilaborane solid 412 was measured by variable-angle spectroscopic ellipsometry as being 147 nm. The XPS depth profile in FIG. 28 established the relative atomic concentrations of boron, silicon, and oxygen in the bulk oxysilaborane solid 412 as respectively: 88.1%, 9.5%, and 2.5%. The relative atomic concentration of boron in the oxysilaborane solid 412 of this example is the same as the oxysilaborane solid 412 within Example 5. The atomic concentration of silicon in the oxysilaborane solid 412 of this example decreased relative to that of the oxysilaborane solid 412 in Example 5. The atomic concentration of oxygen in the oxysilaborane solid 412 of this example was increased relative to that of the picocrystalline oxysilaborane solid 412 in Example 5.

Figure 29:
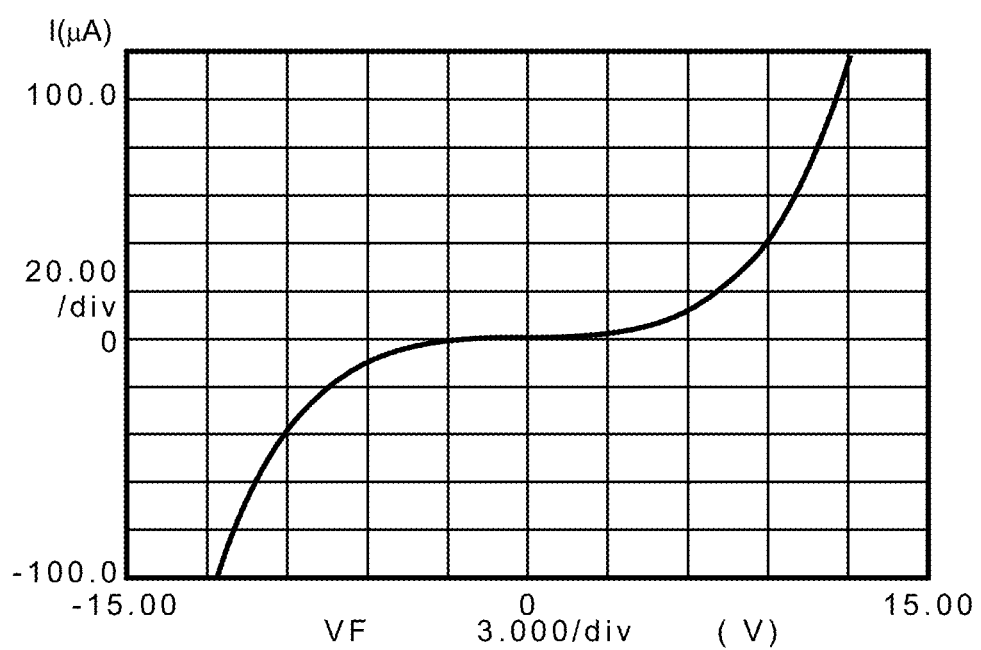
FIG. 29 is a linear graph of the current-voltage characteristics of the oxysilaborane film deposited as in Example 6, as measured by an HP-4145 parameter analyzer with the sweep signals obtained by a mercury probe.
Figure 30:
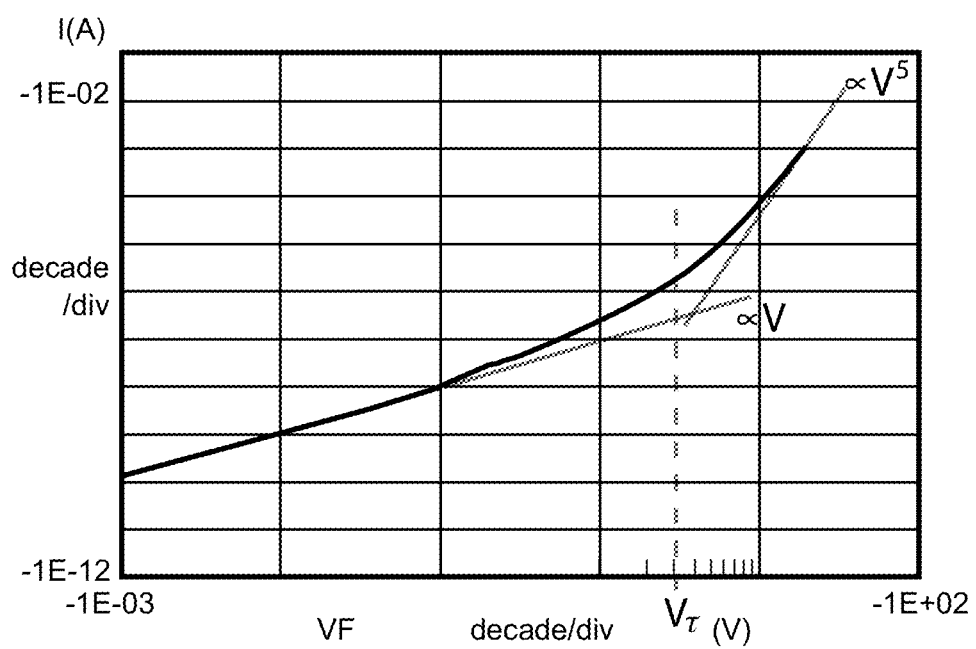
FIG. 30 is a log-log graph of the current-voltage characteristics of the oxysilaborane film deposited as in Example 6, as measured by an HP-4145 parameter analyzer with the sweep signals obtained by a mercury probe.

An RBS and HFS analysis established the bulk relative atomic concentrations of boron, hydrogen, silicon, and oxygen as respectively being: 63%, 23%, 11%, and 3%. The relative atomic concentration of oxygen is close to its RBS detection limit and, thus, is not accurate. The impedance of the oxysilaborane solid 412 of this example was measured by an HP-4145 parameter analyzer, with the sweep signals obtained by a mercury probe. Linear and logarithm graphs of the impedance characteristics of the oxysilaborane solid 412 are respectively shown in FIGS. 29-30. The impedance characteristics of the oxysilaborane solid 412 of this example exhibited a modestly greater impedance than that of the oxysilaborane solid 412 in Example 5.

Example 7

Figure 31:
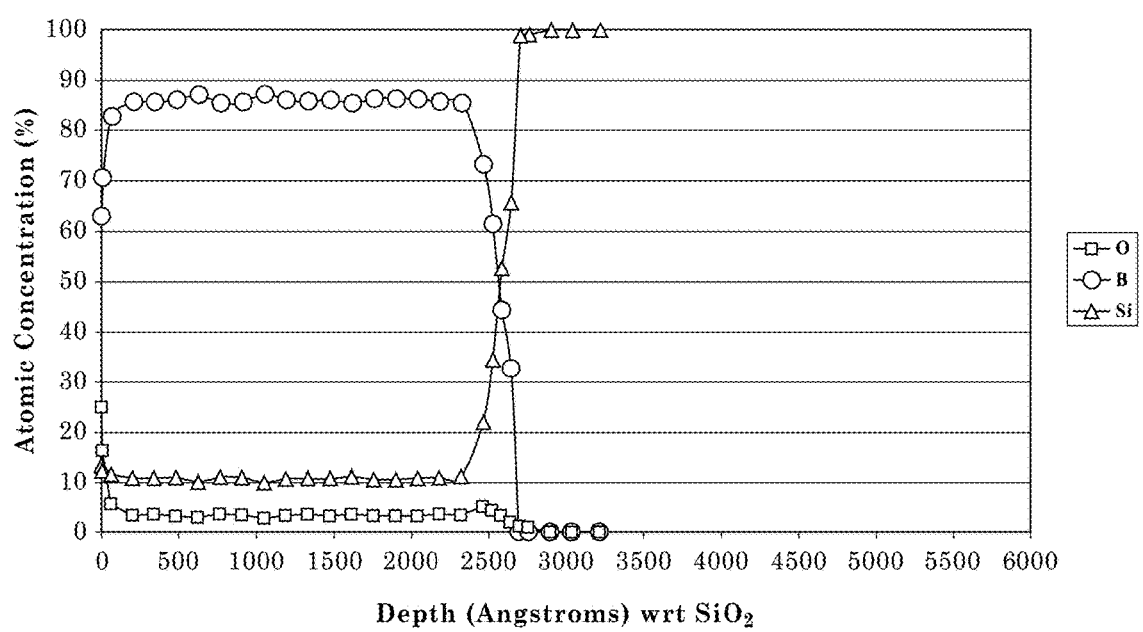
FIG. 31 is an x-ray photoelectron spectroscopy (XPS) depth profile of the oxysilaborane film as deposited in Example 7.
Figure 32:
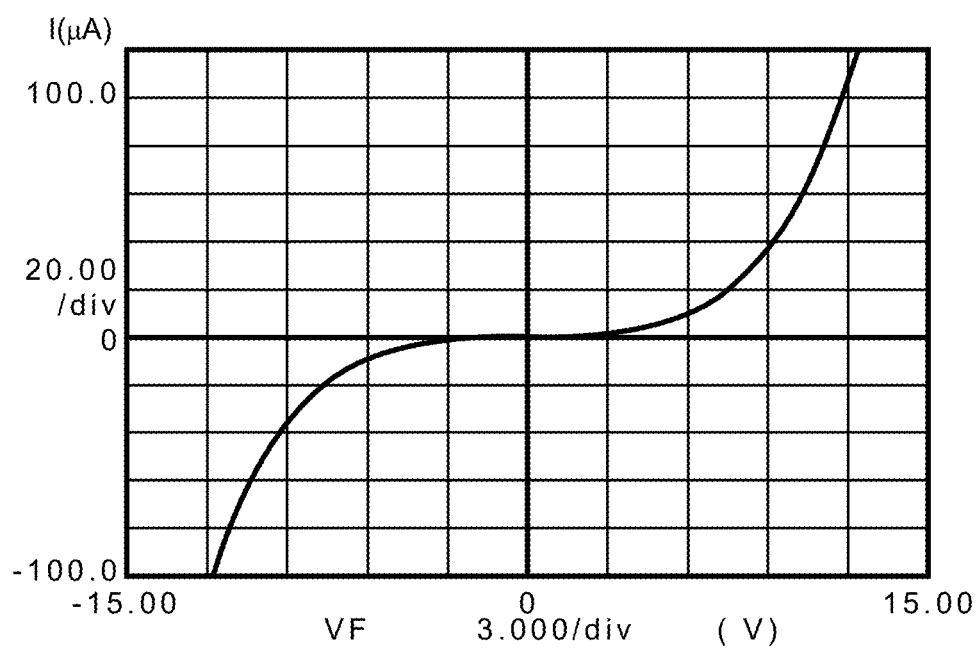
FIG. 32 is a linear graph of the current-voltage characteristics of the oxysilaborane film deposited as in Example 7, as measured by an HP-4145 parameter analyzer with the sweep signals obtained by a mercury probe.
Figure 33:
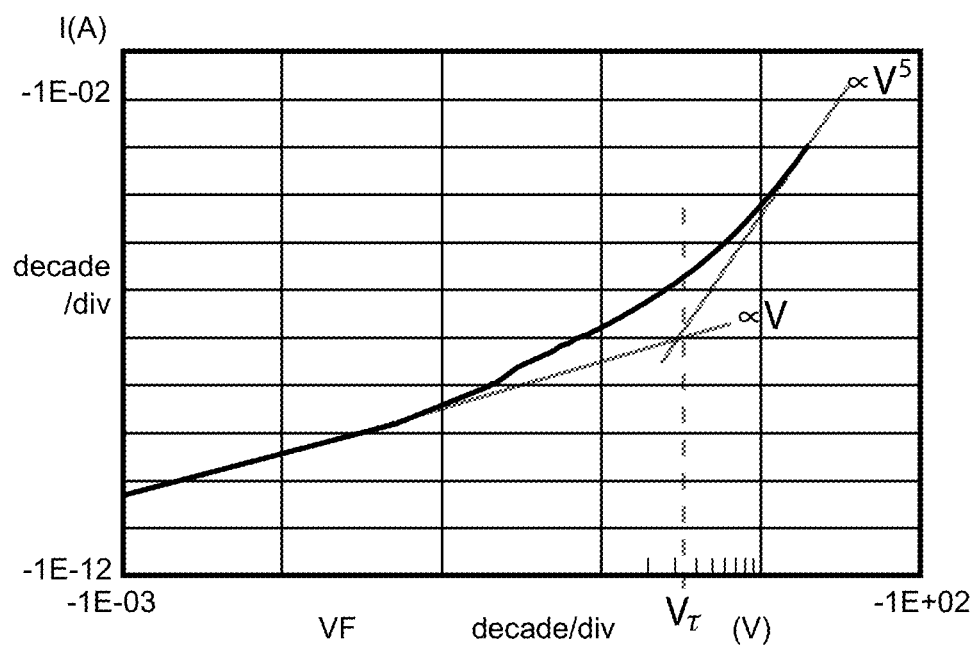
FIG. 33 is a log-log graph of the current-voltage characteristics of the oxysilaborane film deposited as in Example 7, as measured by an HP-4145 parameter analyzer with the sweep signals obtained by a mercury probe.

The procedure described in Example 6 was carried out with the sole exception that the flow rate of the nitrous oxide was increased from 80 sccm to 100 sccm. The thickness of the oxysilaborane solid 412 was established by variable-angle spectroscopic ellipsometry as 140 nm. The XPS depth profile in FIG. 31 established the relative atomic concentrations of boron, silicon, and oxygen in the oxysilaborane solid 412 as being respectively: 85.9%, 10.7%, and 3.4%. The impedance of the oxysilaborane solid 412 of this example was measured by an HP-4145 analyzer, with the two sweep signals obtained by a mercury probe. Linear and log-log graphs of the current-voltage characteristics of the oxysilaborane solid 412 of this example are shown in FIGS. 32-33. The solid 412 of this example exhibited a slightly higher impedance than that of Example 6 due to the relatively larger oxygen concentration.

Example 8

Figure 34:
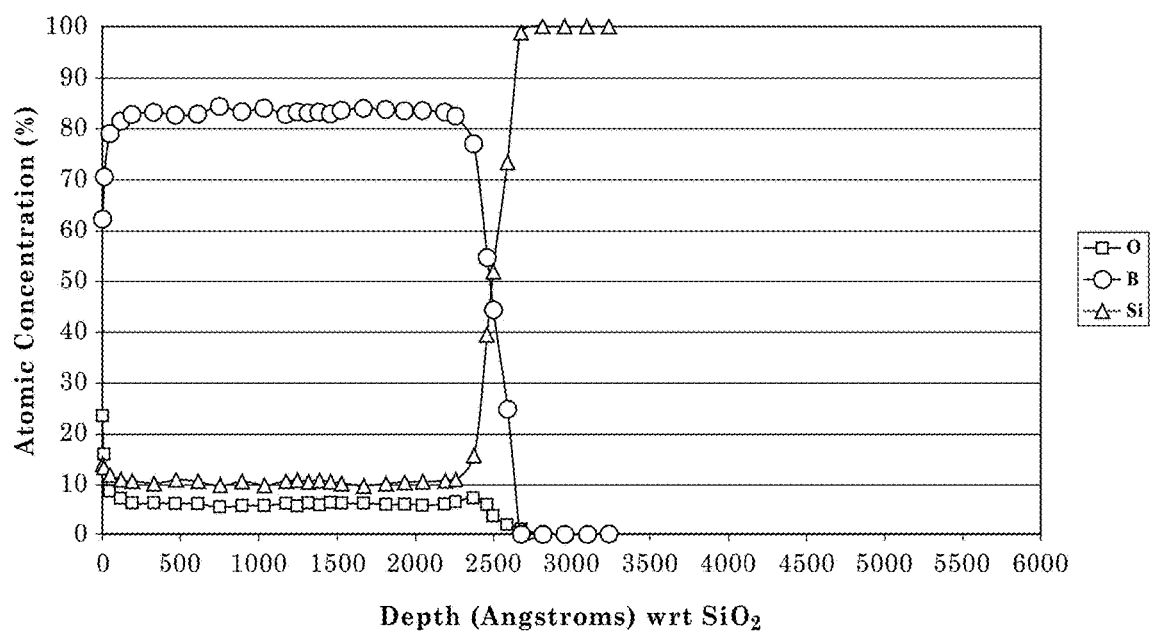
FIG. 34 is an x-ray photoelectron spectroscopy (XPS) depth profile of the oxysilaborane film as deposited in Example 8.
Figure 35:
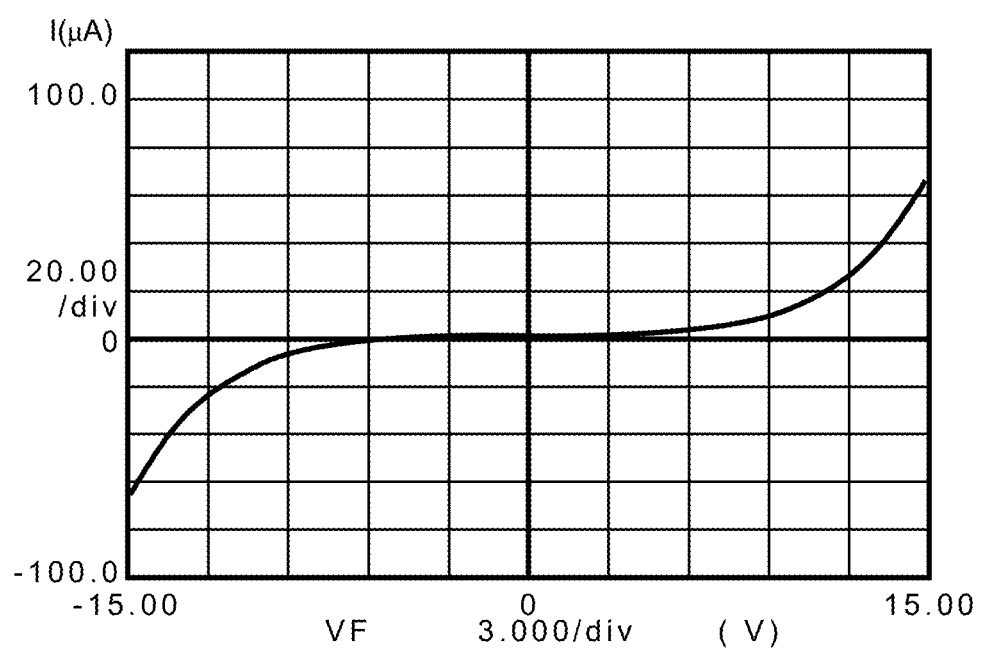
FIG. 35 is a linear graph of the current-voltage characteristics of the oxysilaborane film deposited as in Example 8, as measured by an HP-4145 parameter analyzer with the sweep signals obtained by a mercury probe.
Figure 36:
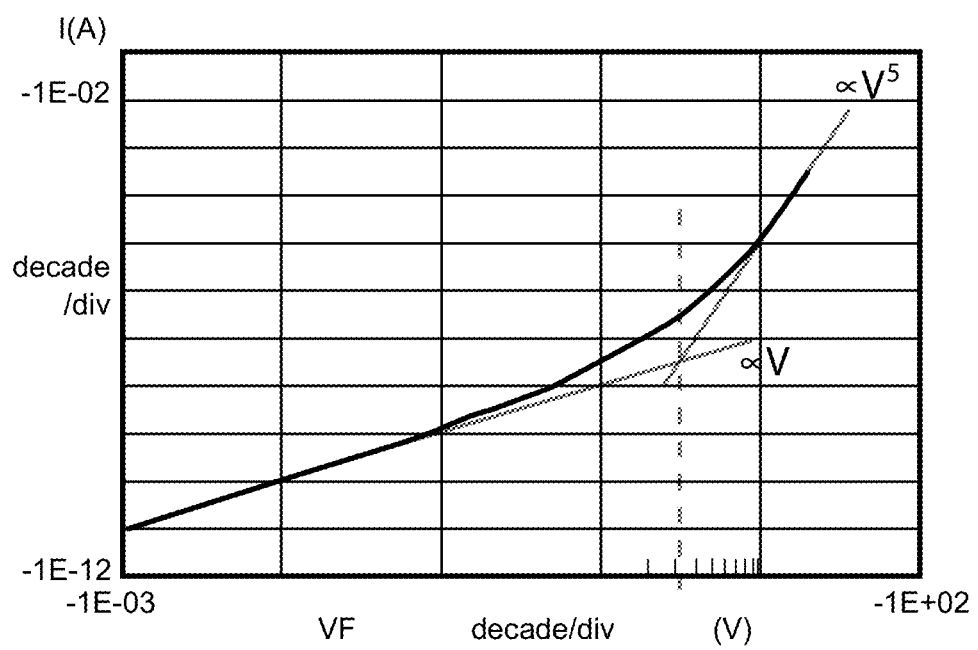
FIG. 36 is a log-log graph of the current-voltage characteristics of the oxysilaborane film deposited as in Example 8, as measured by an HP-4145 parameter analyzer with the sweep signals obtained by a mercury probe.

The procedure described in Example 7 was carried out with the sole exception that the flow rate of nitrous oxide was increased from 100 sccm to 300 sccm. The thickness of the thin oxysilaborane solid 412 was measured by variable-angle spectroscopic ellipsometry as being 126 nm. The XPS depth profile in FIG. 34 measured the relative atomic bulk concentrations of boron, silicon, and oxygen in the oxysilaborane solid 412 of this example as: 83.4%, 10.5%, and 6.2%. The impedance of the oxysilaborane solid 412 was measured by an HP-4145 parameter analyzer. The impedance characteristics of the oxysilaborane solid 412 are shown in FIGS. 35-36.

Example 9

Figure 37:
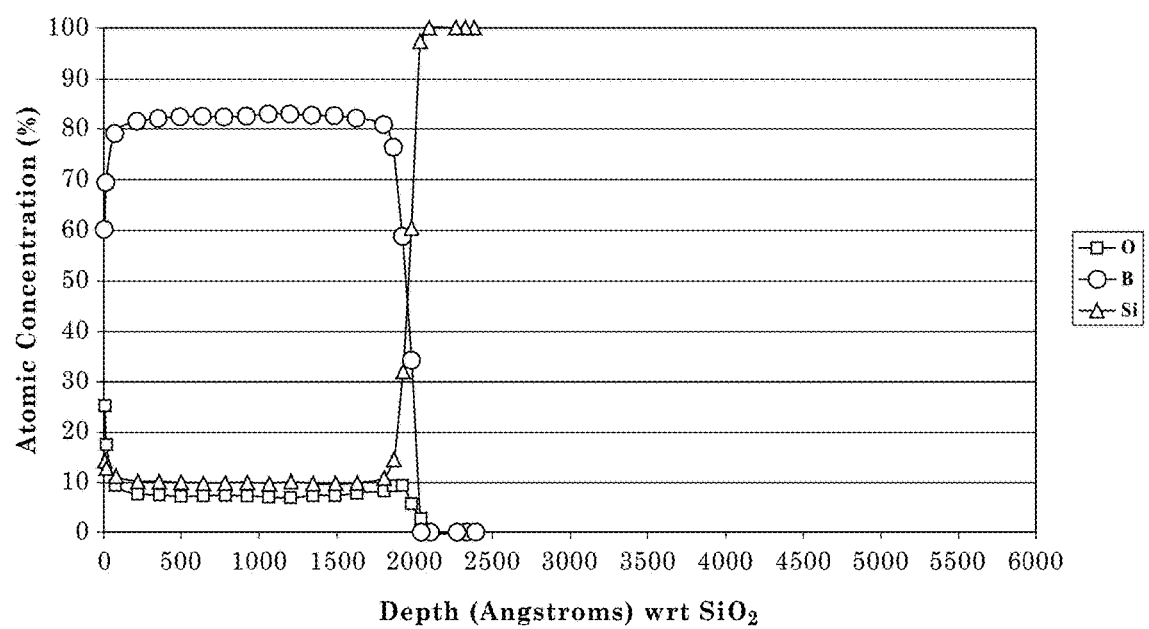
FIG. 37 is an x-ray photoelectron spectroscopy (XPS) depth profile of the oxysilaborane film as deposited in Example 9.
Figure 38:
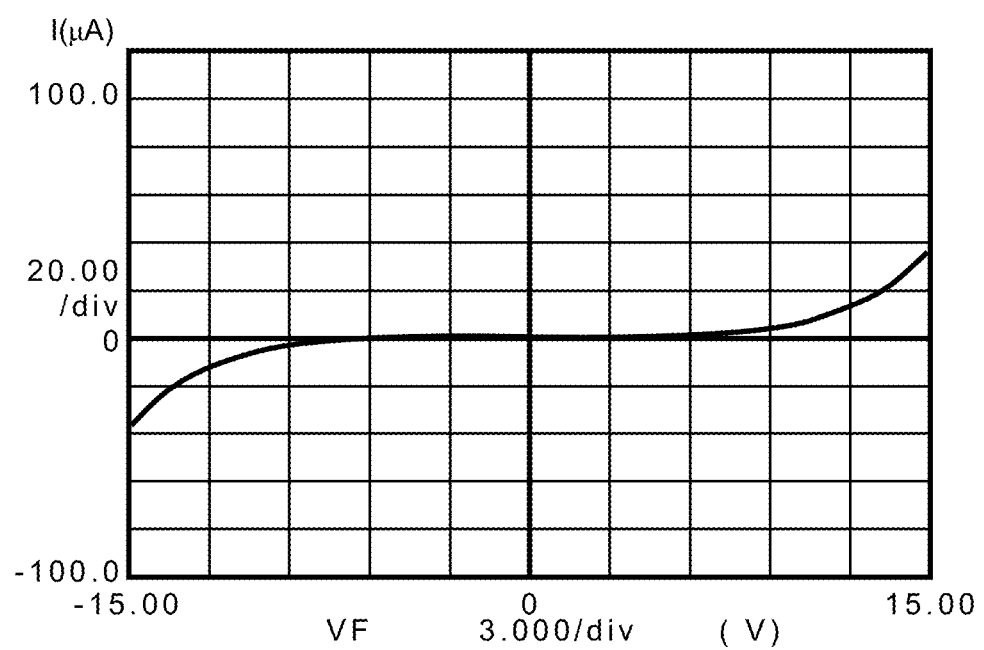
FIG. 38 is a linear graph of the current-voltage characteristics of the oxysilaborane film deposited as in Example 9, as measured by an HP-4145 parameter analyzer with the sweep signals obtained by a mercury probe.
Figure 39:
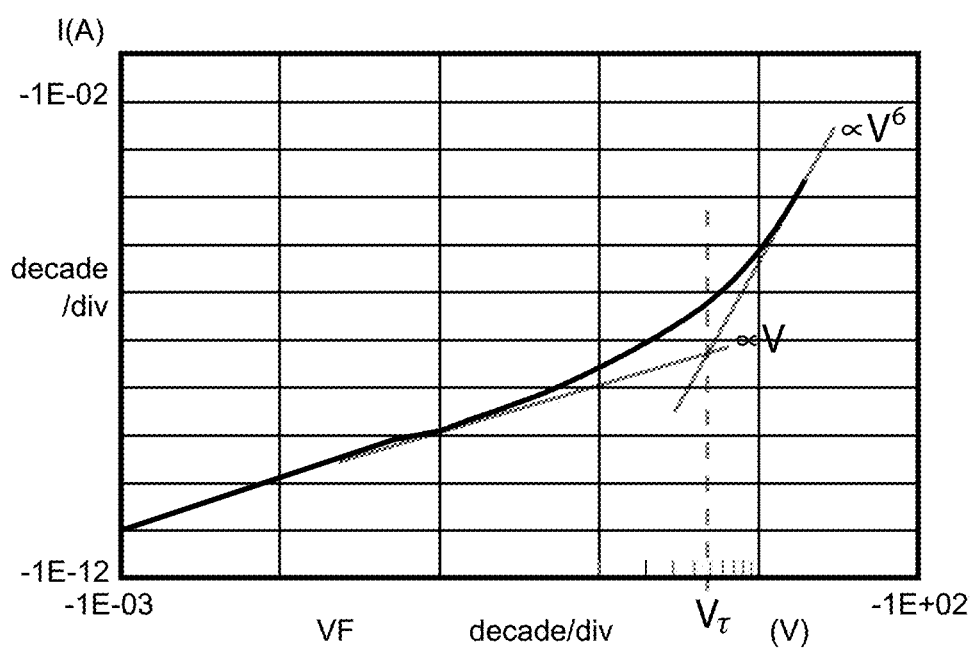
FIG. 39 is a log-log graph of the current-voltage characteristics of the oxysilaborane film deposited as in Example 9, as measured by an HP-4145 parameter analyzer with the sweep signals obtained by a mercury probe.

The procedure in Example 8 was carried out with the sole exception that the nitrous oxide flow rate was increased from 300 to 500 sccm. The thickness of the thin oxysilaborane solid 412 of this example was measured by variable-angle spectroscopic ellipsometry as 107 nm. The XPS depth profile in FIG. 37 established the relative atomic concentrations of boron, silicon and oxygen in the bulk oxysilaborane solid 412 of this example as being: 82.4%, 10.0%, and 7.6%. RBS and HFS analysis established the bulk relative atomic concentrations of boron, hydrogen, silicon, and oxygen: 66%, 20%, 9%, and 5%. The impedance of the oxysilaborane solid 412 of this example was measured by an HP-4145 parameter analyzer, with sweep signals obtained by a mercury probe. Linear and log-log graphs of the impedance characteristics of the oxysilaborane solid 412 of this example are in FIGS. 38-39.

The oxysilaborane solid 412 of this example is oxygen-rich, such that it does not exist within the preferred compositional range ($2 \leq x \leq 4$, $3 \leq y \leq 5$ and $0 \leq z \leq 2$) of self-assembled picocrystalline oxysilaborane $(B_{12}H_4)_x Si_y O_z$ but rather is contained in the broader compositional range ($0 \leq w \leq 5$, $2 \leq x \leq 4$, $2 \leq y \leq 5$, $0 \leq z \leq 3$) of oxysilaborane $(B_{12})_x Si_y O_z H_w$. It is significant that picocrystalline oxysilaborane unpins the surface Fermi level of monocrystalline silicon so as to modulate the surface electrochemical potential of monocrystalline silicon and, at the same time, to conduct electricity. In order to more fully appreciate such a property, it is purposeful to consider examples in which an electrochemical rectifier is formed with monocrystalline silicon.

It is heretofore impossible in the prior art to vary the electrochemical potential of a monocrystalline silicon region throughout the forbidden energy region, while conducting electric charge, due to an undesirable contact potential associated with mobile-charge diffusion between a monocrystalline silicon region and a conjoined solid of a different work function. This deficiency is remedied by self-assembled picocrystalline oxysilaborane by means of actual examples.

Example 10

Monocrystalline silicon was epitaxially deposited over a (001) boron-doped p-type monocrystalline substrate 421 with a 100 mm diameter and 525 μm thickness. The resistivity of the degenerate monocrystalline silicon substrate 421 was 0.02 Ω-cm, which corresponds to an acceptor concentration of $4 \times 10^{18}$ cm$^{-3}$. A nondegenerate p-type monocrystalline silicon layer 422 was deposited on the silicon substrate 421. The epitaxial silicon layer 422 had a thickness of 15 pm and a resistivity of 2 Ω-cm, which relates to an acceptor impurity concentration of $\sim 7 \times 10^{15}$ cm$^{-3}$. All oxide was removed by a hydrofluoric acid deglaze. After the acid deglaze, the silicon substrate 421 was inserted onto a resistively-heated susceptor in an EMCORE MOCVD reactor by a load-lock system isolating the deposition chamber from the ambient. The deposition chamber was mechanically pumped below 50 mtorr, whereupon a 3% mixture by volume of diborane in hydrogen $B_2H_6(3\%)/H_2(97\%)$ at the flow rate of 150 sccm and a 7% mixture by volume of silane in hydrogen $SiH_4(7\%)/H_2(93\%)$ at the flow rate of 300 sccm were introduced into the deposition chamber. Nitrous oxide $N_2O$ was introduced at a flow rate of 100 sccm.

The gases were permitted to mix before entering into the deposition chamber. Upon the stabilization of the reactant gases, the chamber pressure was regulated at 1.5 torr while the susceptor was rotated at 1100 rpm. The substrate temperature was the increased to 230° C. for 2 minutes. The susceptor temperature was then further increased to 260° C., whereupon it stabilized and the chemical reaction was permitted to proceed for 12 minutes. The susceptor heating was secured and the sample was permitted to cool below 80° C. in the reactant gases before it was removed from the deposition chamber. An oxysilaborane solid 423 was deposited. The thickness was measured by variable-angle spectroscopic ellipsometry as being 12.8 nm. Due to the thickness, the oxysilaborane solid 423 showed no additional coloration as a result of the solid deposition.

Figure 40:
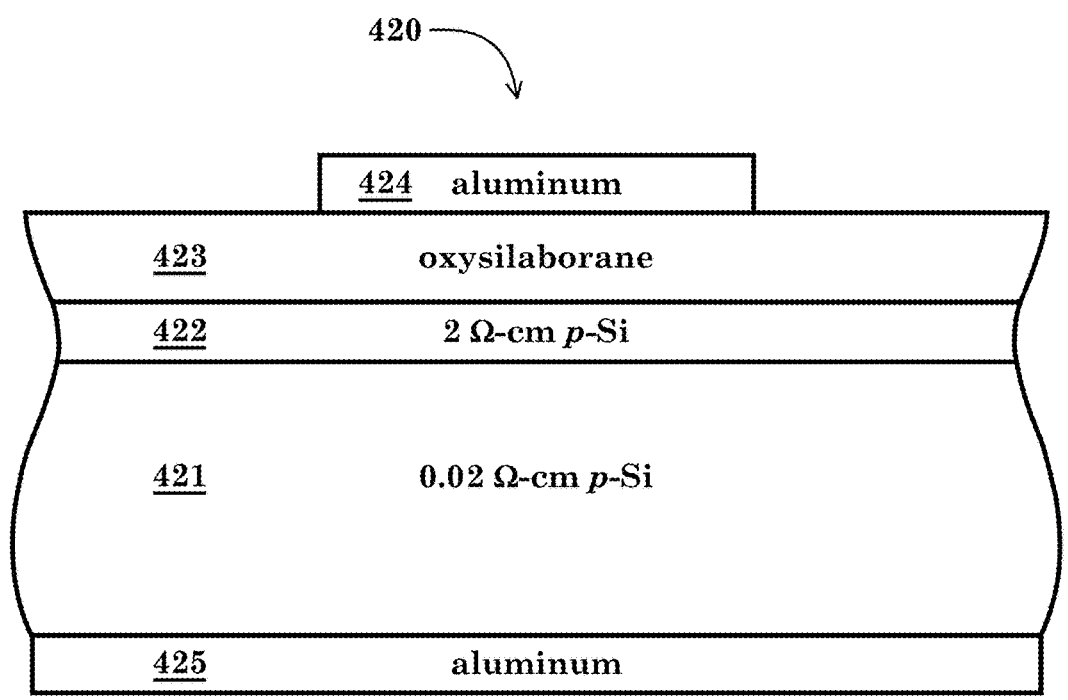
FIG. 40 is an illustration of a p-isotype electrochemical rectifier comprising an oxysilaborane film produced in accordance with Example 10.

Aluminum was evaporated over the substrate 421 backside in a bell jar evaporator, after which, a similar layer of aluminum was evaporated on the oxysilaborane solid 423 through a shadow mask in the bell jar evaporator. The topside aluminum formed the cathode electrode 424 and the backside aluminum formed the anode electrode 425, as shown in FIG. 40. The electrical characteristics of the p-isotype electrochemical rectifier 420 of this example were measured by an HP-4145 parameter analyzer, with sweep signals obtained from the anode and cathode electrodes 425 and 424 by means of microprobes. The linear current-voltage characteristics of the p-isotype electrochemical rectifier 420 of this example are shown at two different current-voltage ranges in FIGS. 41-42. The electrochemical rectifier 420 achieves an asymmetrical electrical conductance without the aid of a p-n junction by means of a variation in the surface electrochemical potential.

Figure 41:
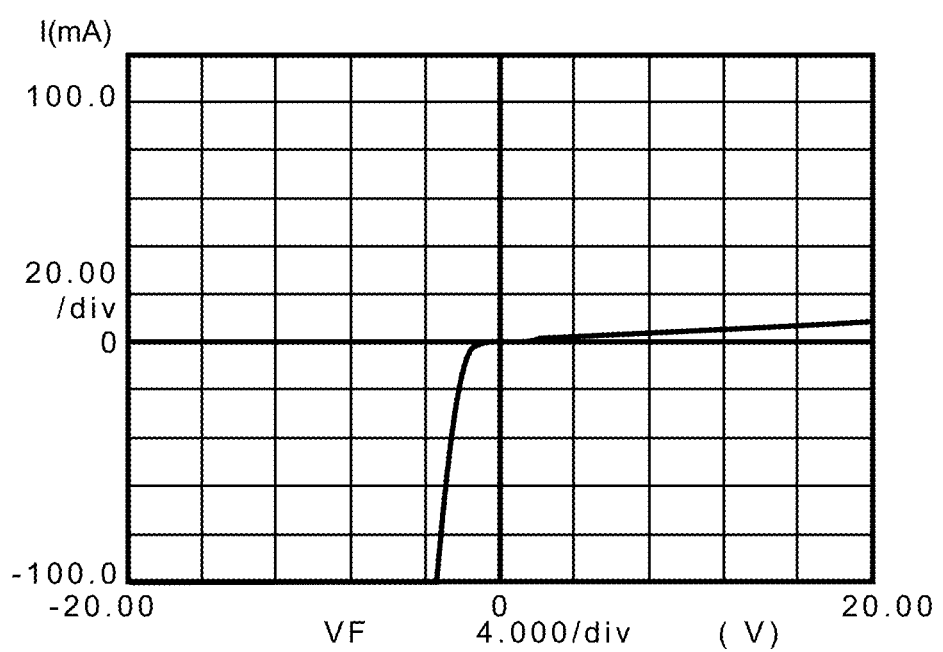
FIG. 41 is a linear graph of the current-voltage characteristics of the electrochemical rectifier of Example 10, as measured by an HP-4145 parameter analyzer with the sweep signals obtained from the anode and cathode electrodes by means of microprobes.
Figure 42:
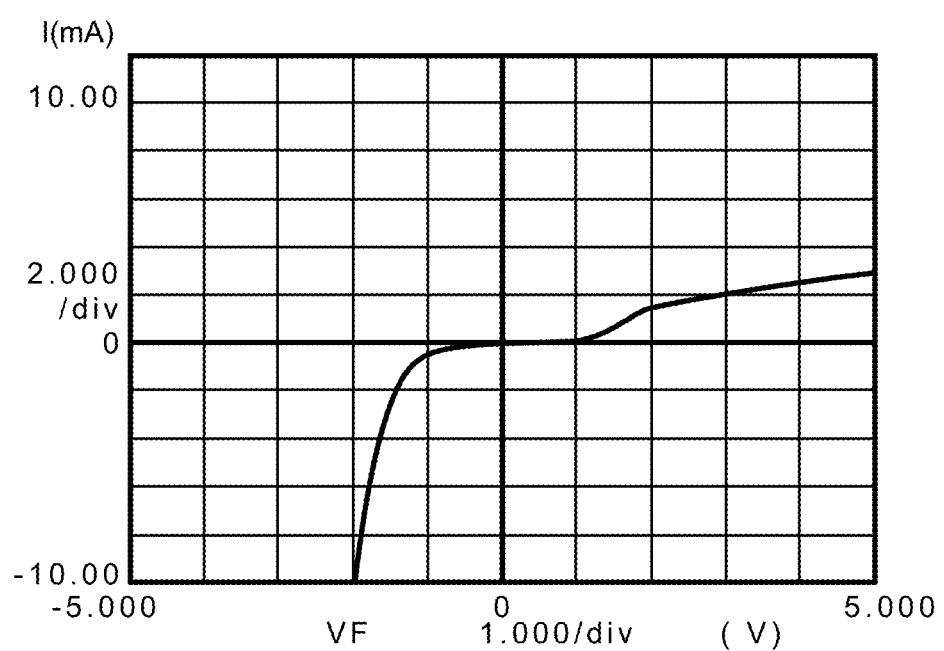
FIG. 42 is a linear graph of a different current-voltage range of the electrochemical rectifier of Example 10, as measured by an HP-4145 parameter analyzer with the sweep signals obtained from the anode and cathode electrodes by means of microprobes.
Figure 43:
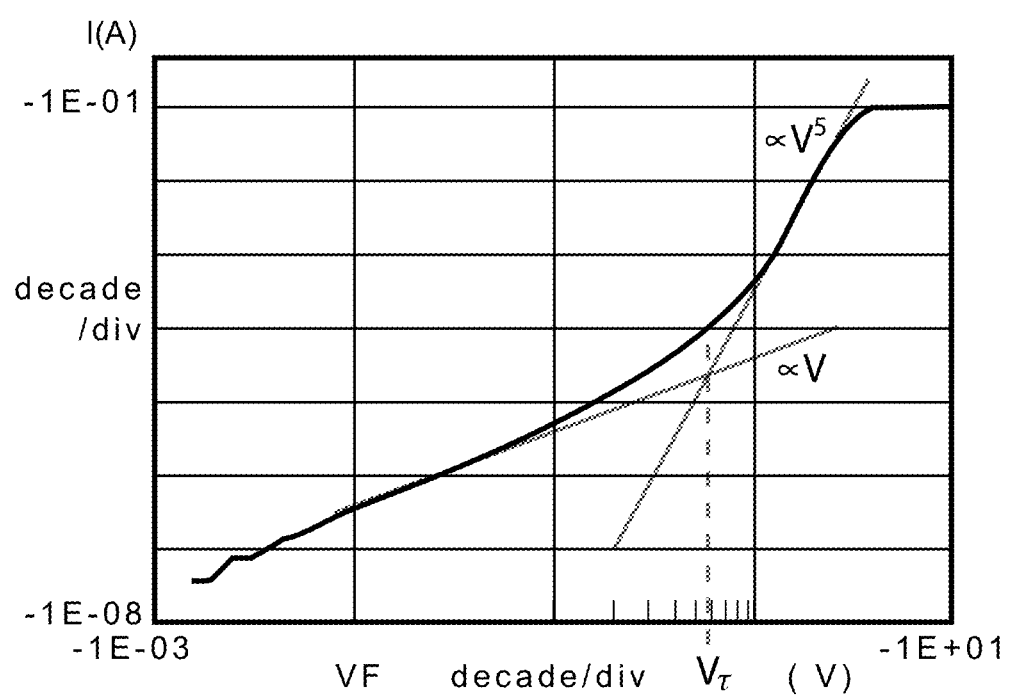
FIG. 43 is a log-log graph of the current-voltage characteristics of the electrochemical rectifier of Example 10, as measured by an HP-4145 parameter analyzer with the sweep signals obtained from the anode and cathode electrodes by means of microprobes.
Figure 44:
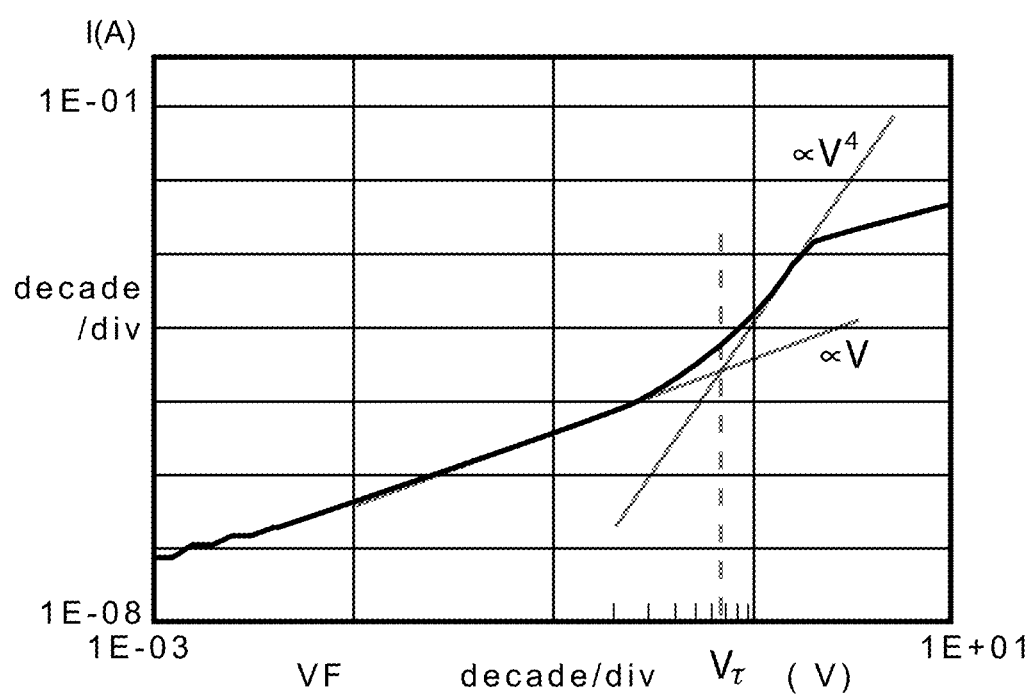
FIG. 44 is a log-log graph of the current-voltage characteristics of the electrochemical rectifier of Example 10, as measured by an HP-4145 parameter analyzer with the sweep signals obtained from the anode and cathode electrodes by means of microprobes.

As shown in FIG. 41, a greater current results when the cathode electrode 424 is negatively-biased (forward-biased) relative to the anode electrode 425. Furthermore, when the cathode electrode 424 is positively-biased (reverse-biased) relative to the anode electrode 425, the much smaller current increases with an increased reverse bias beyond ~1V. The increased reverse-bias current is believed due, in part, to non-ideal processing conditions. Forward-bias and reverse-bias logarithm current-voltage plots are represented in FIGS. 43-44.

Example 11

Figure 45:
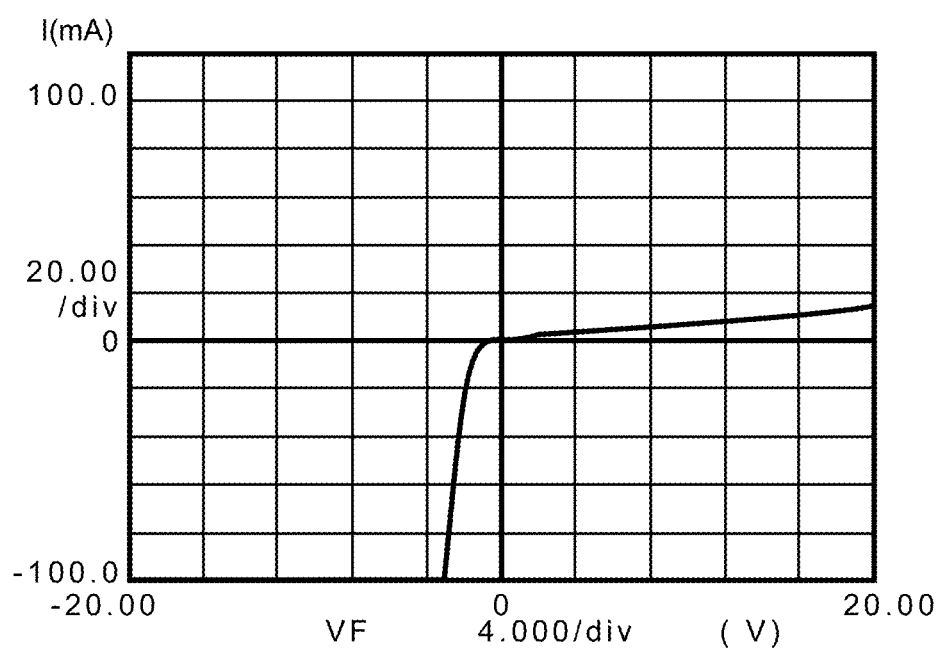
FIG. 45 is a linear graph of the current-voltage characteristics of the electrochemical rectifier of Example 11, as measured by an HP-4145 parameter analyzer with the sweep signals obtained from the anode and cathode electrodes by means of microprobes.
Figure 46:
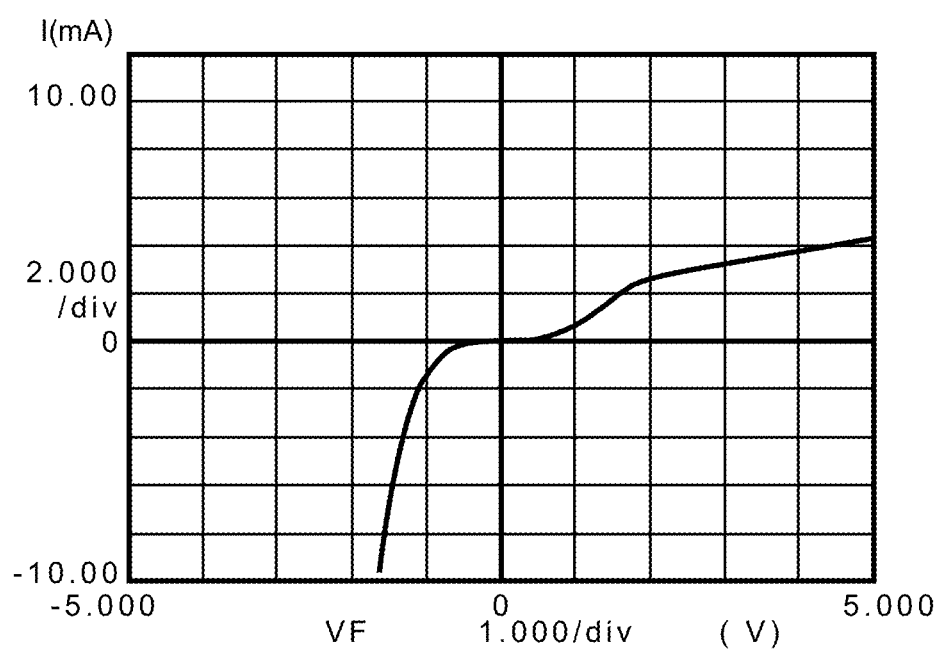
FIG. 46 is a linear graph of a different current-voltage range of the electrochemical rectifier of Example 11, as measured by an HP-4145 parameter analyzer with the sweep signals obtained from the anode and cathode electrodes by means of microprobes.
Figure 47:
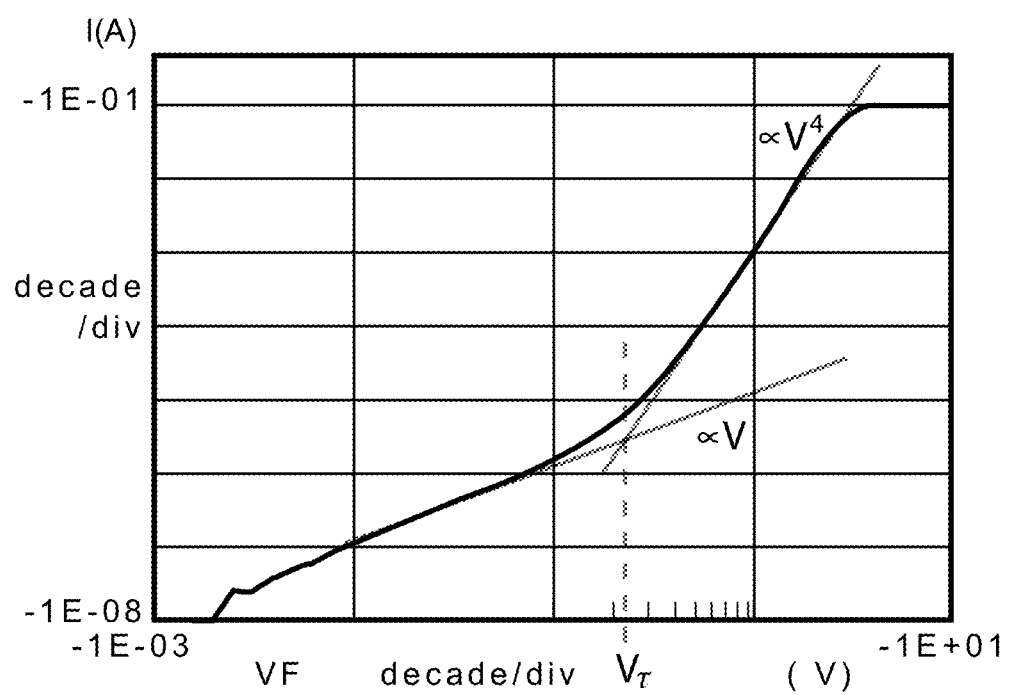
FIG. 47 is a log-log graph of the current-voltage characteristics of the electrochemical rectifier of Example 11, as measured by an HP-4145 parameter analyzer with the sweep signals obtained from the anode and cathode electrodes by means of microprobes.
Figure 48:
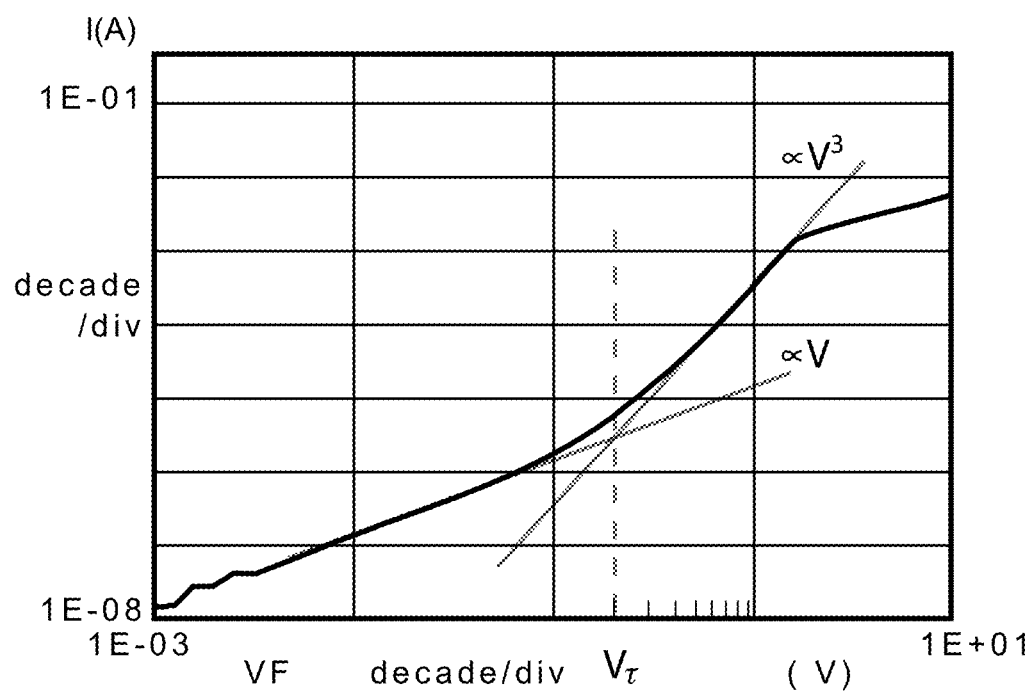
FIG. 48 is a log-log graph of the current-voltage characteristics of the electrochemical rectifier of Example 11, as measured by an HP-4145 parameter analyzer with the sweep signals obtained from the anode and cathode electrodes by means of microprobes.

The procedure described in Example 10 was carried out with the sole exception that the flow rate of nitrous oxide $N_2O$ was increased from 20 sccm to 65 sccm. The thickness of the oxysilaborane solid 423 was measured by variable-angle spectroscopic ellipsometry as 12.4 nm. The electrical characteristics of the p-isotype electrochemical rectifier 420 of this example were measured by an HP-4145 parameter analyzer, with sweep signals obtained from the anode and cathode electrodes 425 and 424 by microprobes. The linear current-voltage characteristics of the p-isotype electrochemical rectifier 420 of this example are shown at different ranges in FIGS. 45-46. Forward-bias and reverse-bias logarithm current-voltage plots are shown in FIGS. 47-48.

Example 12

Figure 50:
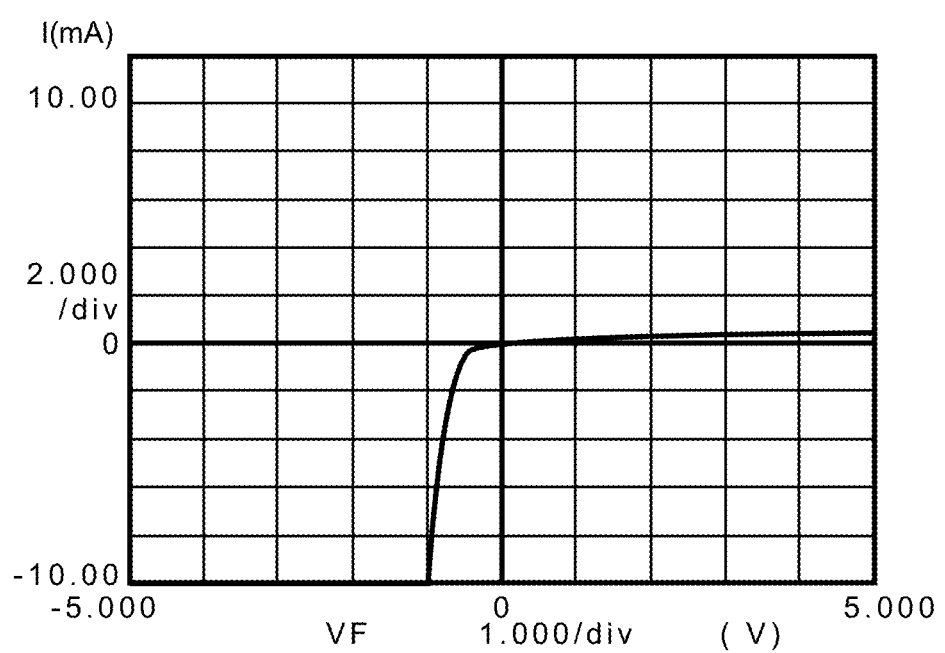
FIG. 50 is a linear graph of a second current-voltage range of the electrochemical rectifier of Example 12, as measured by an HP-4145 parameter analyzer with the sweep signals obtained from the anode and cathode electrodes by means of microprobes.
Figure 51:
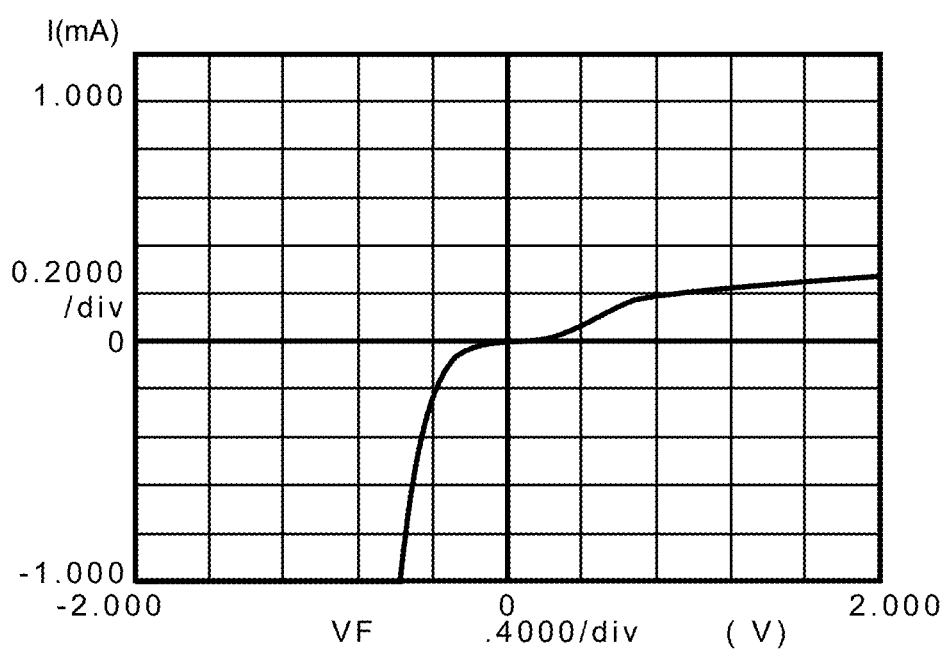
FIG. 51 is a linear graph of a third current-voltage range of the electrochemical rectifier of Example 12, as measured by an HP-4145 parameter analyzer with the sweep signals obtained from the anode and cathode electrodes by means of microprobes.

The procedure described above in Example 11 was carried out with the exception that the reaction time at 260° C. was decreased from 12 minutes to 6 minutes. The thickness of the oxysilaborane solid 423 of this present example was measured by variable-angle spectroscopic ellipsometry as 7.8 nm. The electrical characteristics of the p-isotype electrochemical rectifier 420 of this example were measured by an HP-4145 parameter analyzer, with sweep signals obtained from the anode and cathode electrodes 425 and 424 by two microprobes. Linear current-voltage characteristics of the p-isotype electrochemical rectifier 420 of the present example are shown at three different current-voltage ranges in FIGS. 49-51. The forward-bias and reverse-bias logarithm current-voltage characteristics are presented in FIGS. 52-53. The rectification properties of this example are improved relative to Examples 10-11 due, in large part, to the thinner solid 423. This demonstrates that film thickness affects electrical properties and that thin solids can, in some instances, have improved properties as compared to thicker solids.

Example 13

Figure 54:
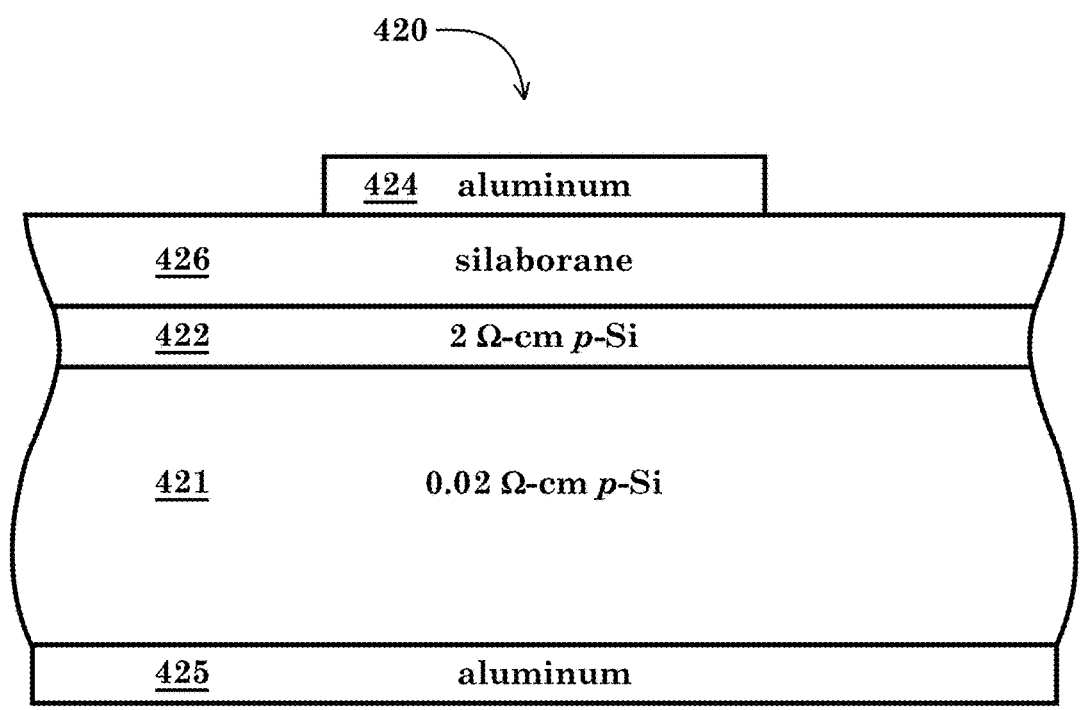
FIG. 54 is an illustration of an electrochemical device comprising a silaborane film produced in accordance with Example 13.
Figure 55:
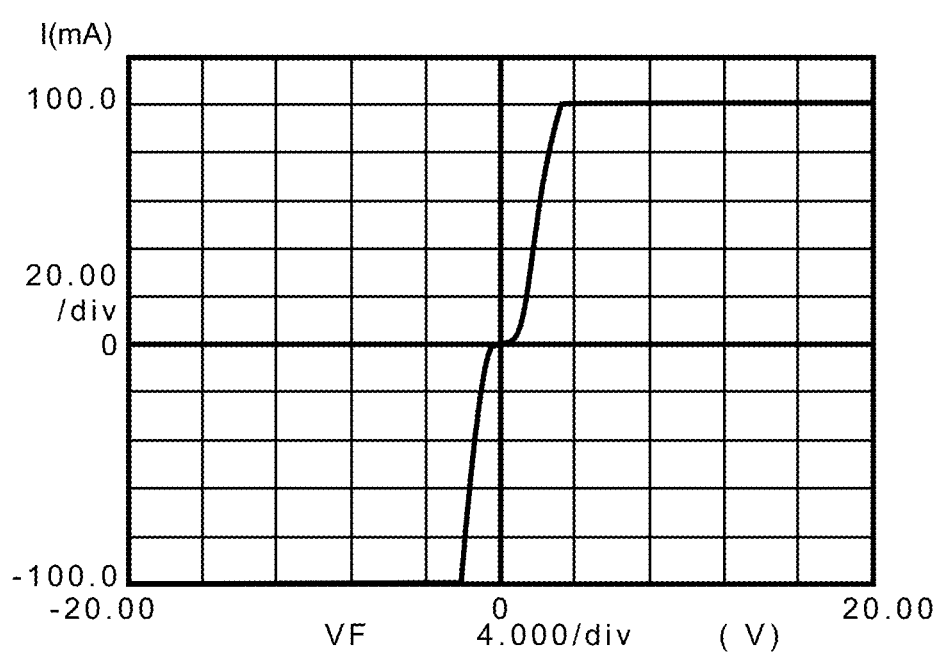
FIG. 55 is a linear graph of current-voltage characteristics of the electrochemical rectifier of FIG. 54, (Example 13) as measured by an HP-4145 parameter analyzer with the sweep signals obtained by means of microprobes.
Figure 56:
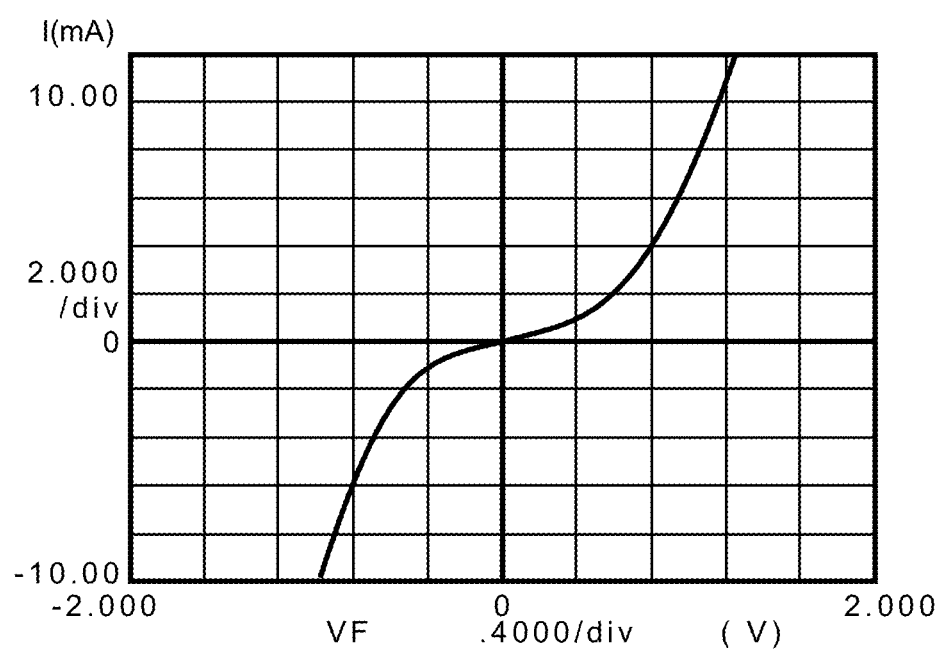
FIG. 56 is a linear graph of a second range of current-voltage characteristics of the electrochemical rectifier of FIG. 54 (Example 13), as measured by an HP-4145 parameter analyzer with the sweep signals obtained by means of microprobes.
Figure 57:
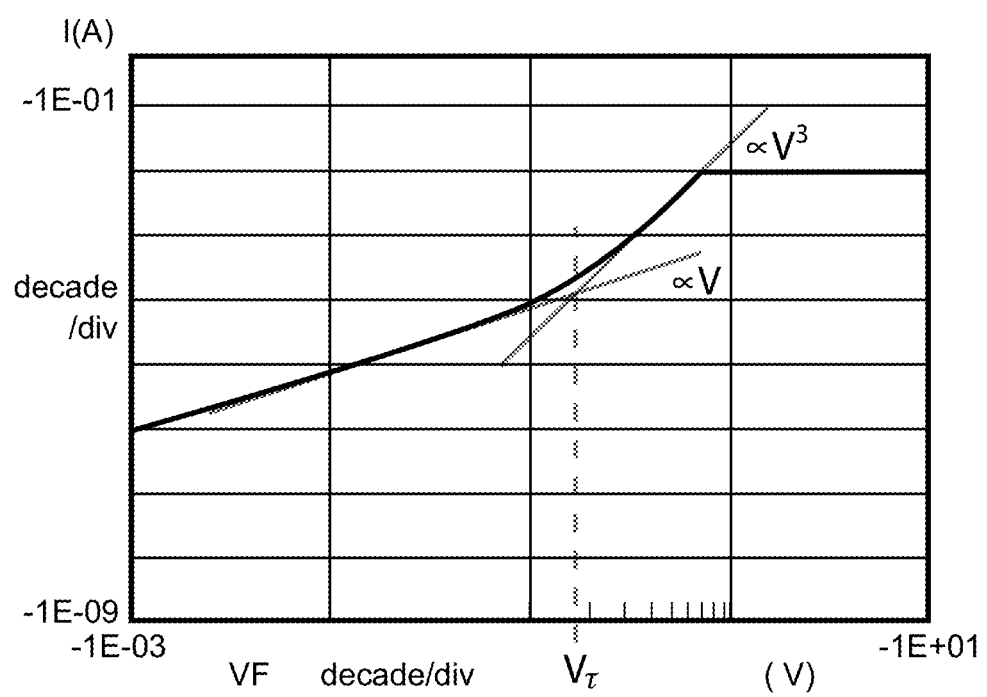
FIG. 57 is a log-log graph of the forward bias current-voltage characteristics of the rectifier of Example 13.
Figure 58:
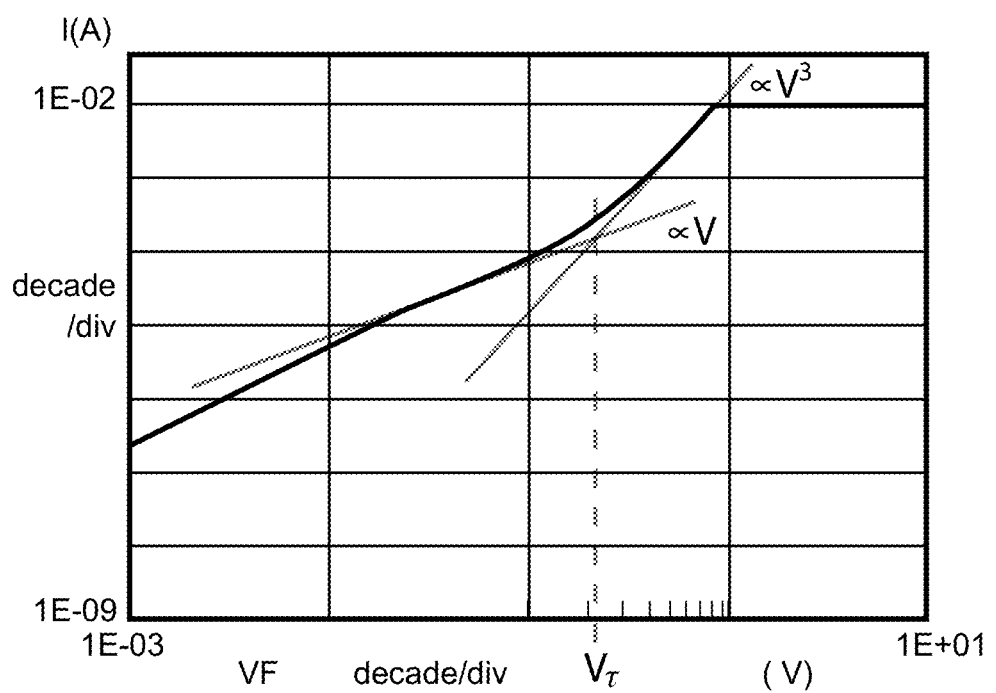
FIG. 58 is a log-log graph of the reverse bias current-voltage characteristics of the rectifier of Example 13.

The procedure in Example 12 was carried out with the exception that nitrous oxide $N_2O$ was never introduced. The thickness of the silaborane solid 426 represented in FIG. 54 was measured by variable-angle spectroscopic ellipsometry as 11.4 nm. The electrical characteristics of the device 420 were measured by an HP-4145 parameter analyzer, with sweep signals obtained from the anode and cathode electrodes 425 and 424 by means of microprobes. The linear current-voltage characteristics of the device 420 are shown in FIGS. 55-56. The forward-bias and reverse-bias logarithm current-voltage plots are shown in FIGS. 57-58.

Ignoring interfacial effects, the composition of the oxysilaborane solid 423 described in Examples 11-12 is prototypical picocrystalline oxysilaborane $(B_{12}{}^{2-}H_4)_4Si_4O_2{}^{2+}$ and the silaborane solid 426 of Example 13 is picocrystalline silaborane $(B_{12}H_4)_3Si_5$. Picocrystalline oxysilaborane $(B_{12}{}^{2-}H_4)_4Si_4O_2{}^{2+}$ and picocrystalline silaborane $(B_{12}H_4)_3Si_5$ exhibit different, albeit complementary, electrochemical properties. The profound difference between the two compositions is exemplified by the fundamental difference in the rectification of the electrochemical devices 420 in Example 12 and Example 13 due to the critical role of oxygen. The difference in devices 420 of these two examples is the oxygen concentration of the picocrystalline solids 423 and 426.

Figure 49:
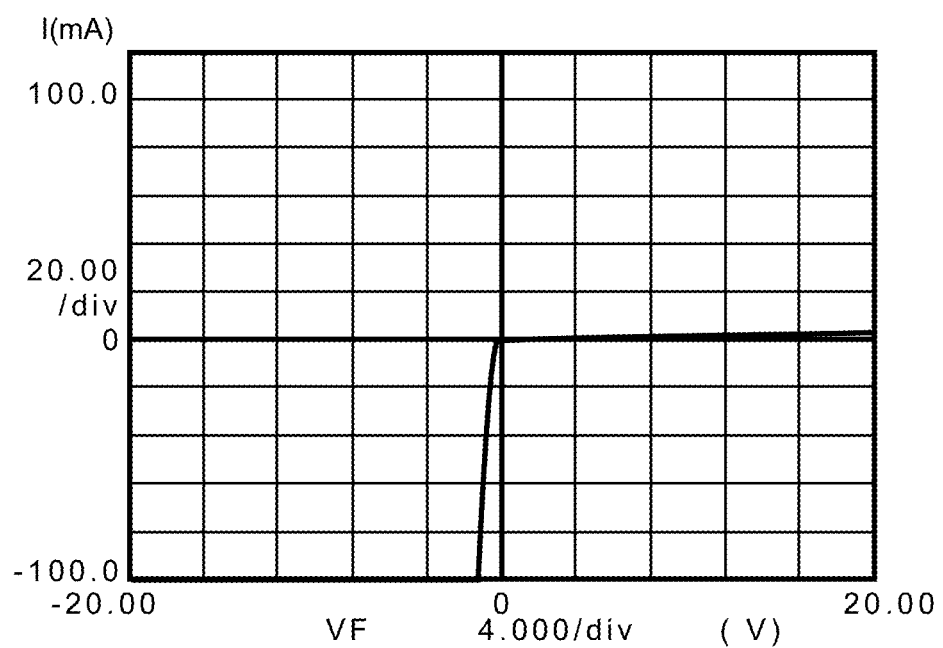
FIG. 49 is a linear graph of a first current-voltage range of the electrochemical rectifier of Example 12, as measured by an HP-4145 parameter analyzer with the sweep signals obtained from the anode and cathode electrodes by means of microprobes.
Figure 52:
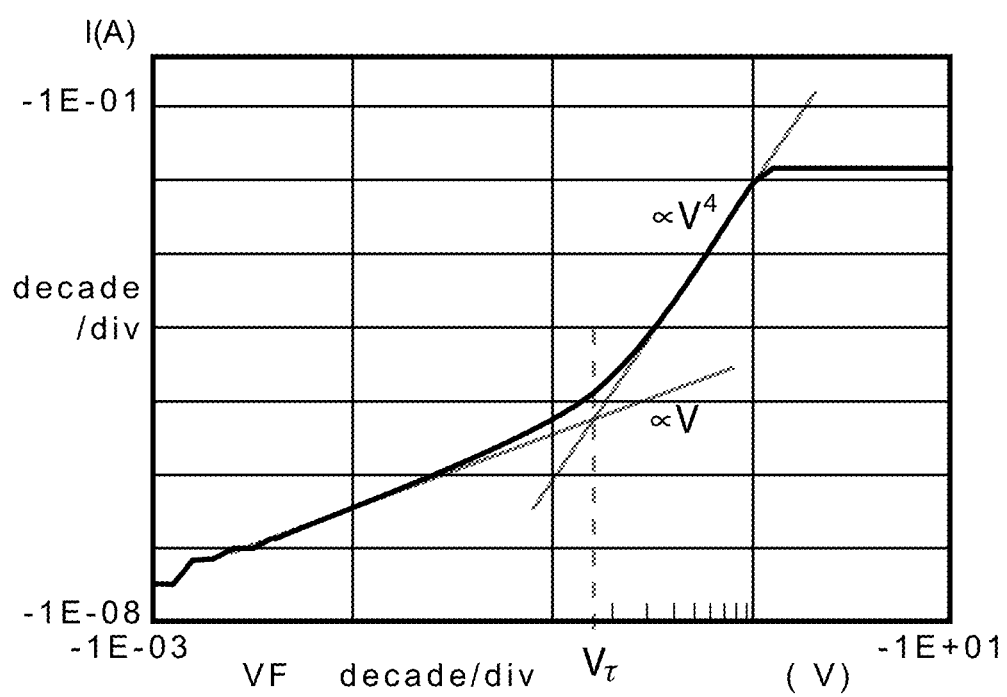
FIG. 52 is a log-log graph of the forward bias current-voltage characteristics of the rectifier of Example 12.
Figure 53:
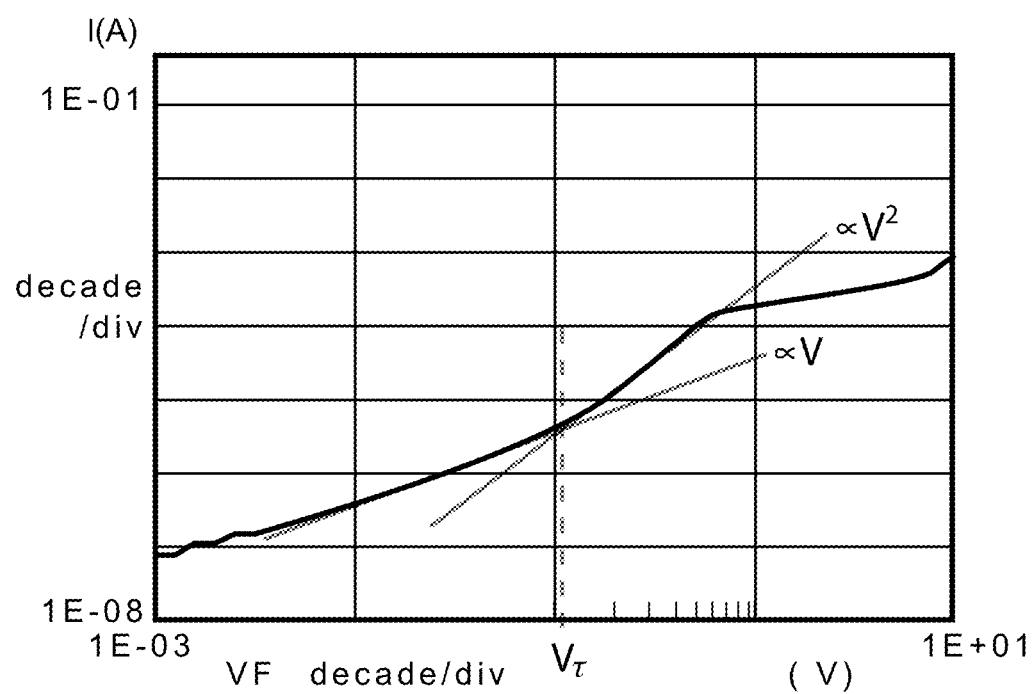
FIG. 53 is a log-log graph of the reverse bias current-voltage characteristics of the rectifier of Example 12.

Referring to FIG. 49, the electrical current of the p-isotype electrochemical rectifier 420 in Example 12 increases significantly as the cathode electrode 424 is increasingly forward-biased (i.e. negatively-biased) relative to the anode electrode 425. As represented in FIG. 52, the forward-bias current in the p-isotype electrochemical rectifier 420 in Example 12 increases linearly with the bias voltage at a low current and increases with a quartic voltage dependence beyond the relaxation voltage. The forward-bias current-voltage characteristic of the p-isotype rectifier 420 in Example 12 is space-charge-limited by the oxysilaborane film 423 beyond a relaxation voltage, whereupon the transit time is less than the relaxation time.

A different situation occurs when the electrochemical rectifier 420 is reverse-biased. Referring now to FIG. 49, the current of the p-isotype electrochemical rectifier 420 in Example 12 increases at a greatly reduced rate as the cathode electrode 424 is increasingly reverse-biased (i.e. positively-biased) relative to the anode electrode 425. This is due to the fact that the picocrystalline oxysilaborane solid 423 in Example 12 is ideally picocrystalline oxysilaborane $(B_{12}{}^{2-}H_4)_4Si_4O_2{}^{2+}$, which constitutes a solid in a closed-shell electronic configuration that supports a novel conduction current. The conduction current represented by the log-log graph in FIG. 52 is, in a number of ways, characteristic of a charge plasma injected in a semiconductor or dielectric. A good summary of this particular phenomenon is provided by Lampert and Mark in the book *Current Injection in Solids*, Academic Press, 1970, pp. 250-275.

Whenever a charge plasma is injected into a semiconductor or dielectric, the current density and voltage vary linearly until a sufficiently high level of charge injection gives rise to a space-charge-limited current density due to a breakdown in charge neutrality. High-level charge injection into a semiconductor tends to result in a quadratic dependence of a space-charge-limited current density on voltage while high-level charge injection in a dielectric tends to result in a cubic dependence of a space-charge-limited current density on voltage. The principal difference between a semiconductor and a dielectric is that the former is typically characterized by a large extrinsic mobile-charge concentration of a negative or positive polarity while the latter is characterized by a negligible mobile-charge concentration.

In principle, the log-log current-voltage characteristic of the electrochemical rectifier 420 in FIG. 52 should be characteristic of a charge plasma injected into a dielectric, given that the oxysilaborane solid 423 in Example 12 has a bulk composition of picocrystalline oxysilaborane $(B_{12}{}^{2-}H_4)_4Si_4O_2{}^{2+}$ with an ideally closed-shell electronic configuration similar to that of a dielectric. As established by Lampert and Mark in the previous reference, mobile-charge diffusion tends to dominate the plasma-injected current-voltage characteristics of a dielectric in a diffusion length of either contact—such that the current density varies exponentially with voltage. If the dielectric length is much greater than the diffusion length, mobile-charge drift dominates the plasma-injected current-voltage characteristics—such that the current varies linearly with voltage up to a relaxation voltage, where it is space-charge-limited with a cubic variation in current density with voltage.

For example, per the above reference by Lampert and Mark, a silicon p-i-n diode with a length of the intrinsic silicon region being 4 mm exhibits a space-charge-limited current-voltage characteristic with a cubic dependency of the current density upon the impressed voltage beyond a relaxation voltage of 10V. When the length of the intrinsic silicon region of the p-i-n diode was reduced to approximately 1 mm, the current density varied exponentially with an impressed voltage due to a dominance of mobile-charge diffusion. Referring, again, to FIG. 52, the electrochemical rectifier 420 in Example 12 possesses a drift space-charge-limited current-voltage characteristic in a thin oxysilaborane solid 423 of only 7.8 nm, which has the bulk composition of picocrystalline oxysilaborane $(B_{12}{}^{2-}H_4)_4Si_4O_2{}^{2+}$.

This is only possible if the extrinsic charge concentration is sufficiently large that the Debye length of the oxysilaborane solid 423 is less than approximately 4 nm. The extrinsic charge concentration $p_0$ of self-assembled picocrystalline oxysilaborane $(B_{12}H_4)_xSi_yO_z$ over the preferred compositional range ($2 \leq x \leq 4$, $3 \leq y \leq 5$ and $0 \leq z \leq 2$) is essentially constant at $p_0 \approx 10^{18}$ cm$^{-3}$. The extrinsic carrier concentration relates to the impurity doping concentration in monocrystalline silicon at the onset of bandgap narrowing. Picocrystalline oxysilaborane $(B_{12}H_4)_xSi_yO_z$ is a novel compound since it exhibits a closed-shell electronic configuration and, also, an extrinsic mobile-charge concentration near the onset of bandgap narrowing in silicon.

It is believed that a possible explanation of the atomic engineering of compositions, made in accordance with this invention, may be given with respect to the picocrystalline artificial borane atom 101 shown in FIG. 9. As previously discussed hereinabove, the boron icosahedron shown in FIG. 9 retains a nearly-symmetrical icosahedral arrangement of the boron nuclei 102 in defiance of the Jahn-Teller theorem. This is believed to be attributed to a lifting of the polyatomic electronic orbital degeneracies by a spin-orbit coupling. In conventional chemistry, the electrons reside in electronic shells in which electrons share a common principal quantum number n. Within each electronic shell there exist subshells in which electrons share a common azimuthal quantum number l associated with an orbital angular momentum. By convention, energy levels in a subshell with a common whole-integer azimuthal quantum number l=0, 1, 2, 3 are respectively denoted as s, p, d, f energy levels in accordance with conventional chemistry.

In conventional chemistry, the atomic and molecular energy levels are all assumed to obey Schrödinger's nonrelativistic wave equation. Although electrons are known to possess a spin angular momentum, spin is not comprehended by Schrödinger's nonrelativistic wave equation. As the result, electrons possessing a different spin angular momentum can occupy a common energy level characterized by a common azimuthal quantum number l associated with a whole-integer-quantized orbital angular momentum. Said orbital angular momentum degeneracy is lifted in the presence of spin-orbit coupling, such that energy levels associated with a whole-integer azimuthal quantum number l are split into doublets of energy levels associated with a half-integer-quantized total angular momentum. A splitting of energy levels by spin-orbit coupling is shown in FIG. 59.

Figure 59:
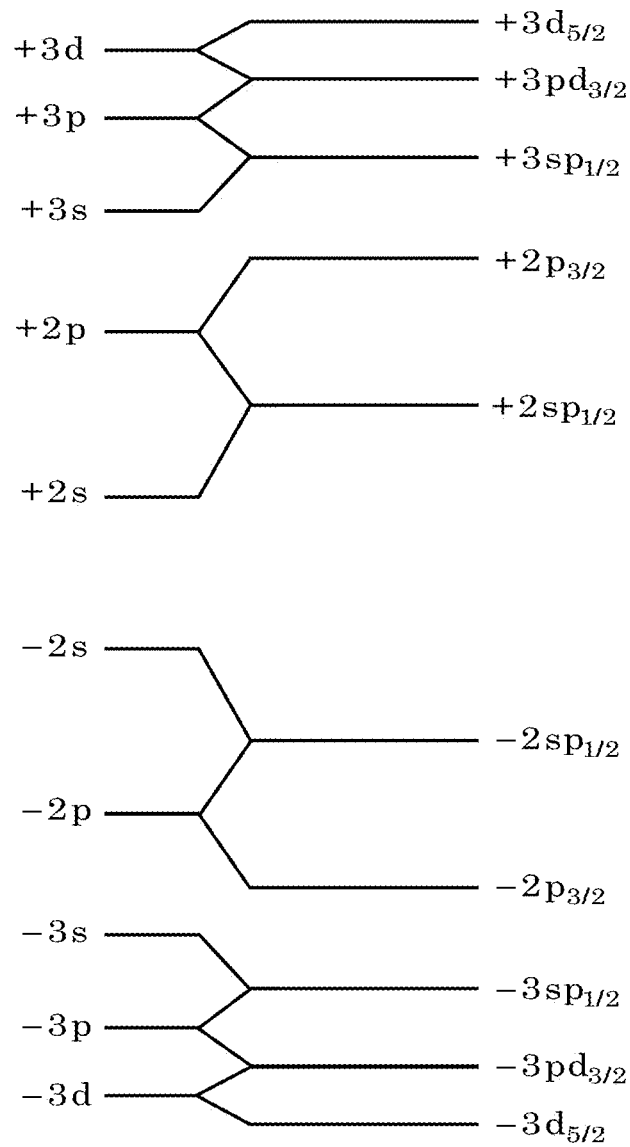
FIG. 59 is an energy level diagram that comprehends energy levels obeying Dirac's relativistic wave equation.

The energy levels in FIG. 59 constitute an energy diagram that comprehends energy levels obeying Dirac's relativistic wave equation in Table 3.3 on page 128 of the book by Sakurai entitled *Advanced Quantum Mechanics*, Benjamin/Cummings Publishing Company, 1984. For the purposes of explanation, consideration will be given to the energy level diagram in FIG. 59. The inner electrons of boron, which do not participate in chemical bonding, are in the n=1 shell. As a result, the n=1 shell is not shown in FIG. 59. The energy levels described by Schrödinger's nonrelativistic wave equation are strictly associated with a positive-definite energy. By convention, the n=+2 shell contains positive-definite energy levels in which there exist +2s and +2p subshells associated with a whole-integer-quantized orbital angular momentum. By convention, the n=+3 shell contains positive-definite energy levels in which there exist +3s, +3p and +3d subshells that are associated with a whole-integer-quantized orbital angular momentum.

In addition to these positive-definite energy levels, Dirac's relativistic wave equation requires an equal number of negative-definite energy levels, which are appropriately designated in FIG. 59. Spin-orbit coupling lifts the orbital angular momentum degeneracy as shown in FIG. 59. By means of example, the +2p energy level is split into the $+2p_{1/2}$ and $+2p_{3/2}$ energy levels by spin-orbit coupling. Observe, further, that the lifted $+2p_{1/2}$ energy level shares a common energy with the $+2s_{1/2}$ energy level, per Dirac's relativistic wave equation. This shared energy level is denoted as $+2sp_{1/2}$ in FIG. 59. The shared energy level $+2sp_{1/2}$ in FIG. 59 is referred to as a degenerate energy level in the literature. For reasons that bear upon preferred embodiments of this invention, the shared energy level $+2sp_{1/2}$ is hereinafter referred to as an "entangled energy level". The other orbitally degenerate energy levels in FIG. 59 are similarly lifted by spin-orbit coupling.

Figure 60:
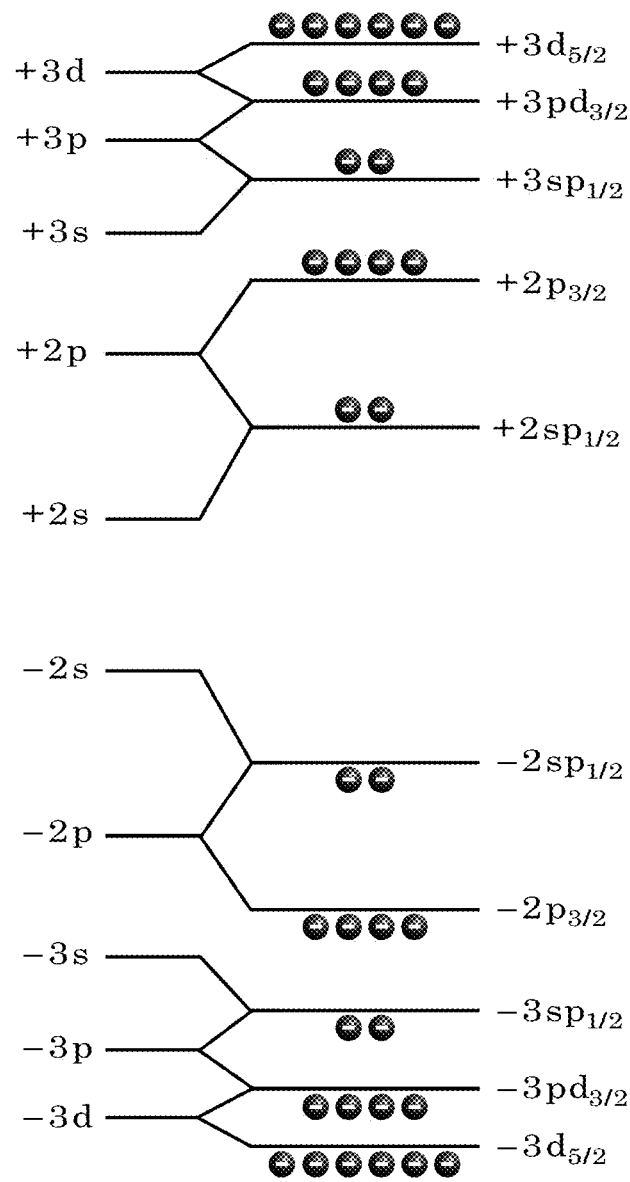
FIG. 60 is an energy level diagram depicting the occupied energy levels believed to be attained by the incorporation of a significant impurity atom, such as gold.

The positive-definite energy levels in FIG. 59 are hereinafter termed the antibonding energy levels while the negative-definite energy levels in FIG. 59 are termed the bonding energy levels. The total occupancy of the energy levels in FIG. 59 by valence electrons is represented in FIG. 60. All 36 valence electrons in FIG. 60 are required to bond the boron icosahedron of the picocrystalline artificial borane atom 101 in FIG. 9. It is first noted that the 36 valence electrons in the energy diagram in FIG. 60 are contained within the nearly-symmetrical boron icosahedron forming the artificial nucleus of a picocrystalline artificial borane atom 101. This manifests that there do not exist boron valence electrons in radial orbitals available for exo-icosahedral bonds to natural atoms or to other picocrystalline artificial borane atoms 101. Thus, the nearly-symmetrical boron icosahedron forming the artificial nucleus of a picocrystalline artificial borane atom 101 is a caged icosahedron, analogous to buckminsterfullerene, with no exo-icosahedral boron bonds.

The valence electrons in FIG. 60 result in an electronic closed-shell configuration in which none of the valence electrons can participate in electric charge conduction through space in picocrystalline oxysilaborane $(B_{12}H_4)_xSi_yO_z$. Charge conduction in picocrystalline oxysilaborane $(B_{12}H_4)_xSi_yO_z$ can be achieved in fundamentally different ways by means of an atomic engineering of the picocrystalline artificial borane atoms 101. The occupied energy levels in FIG. 60 can only be realized when the electron-hole pair generation rate is sufficiently high due to the incorporation of a significant impurity atom, such as gold. In the absence of the sufficient concentration of any significant impurity, such as gold, the valence electrons in FIG. 60 are believed to relax into an occupancy condition of the type represented in FIG. 61 in picocrystalline silaborane $(B_{12}H_4)_3Si_5$. It is believed that the occupancy of energy levels by valence electrons in FIG. 61 is characteristic of picocrystalline silaborane $(B_{12}H_4)_3Si_5$ prior to disproportionation.

Figure 61:
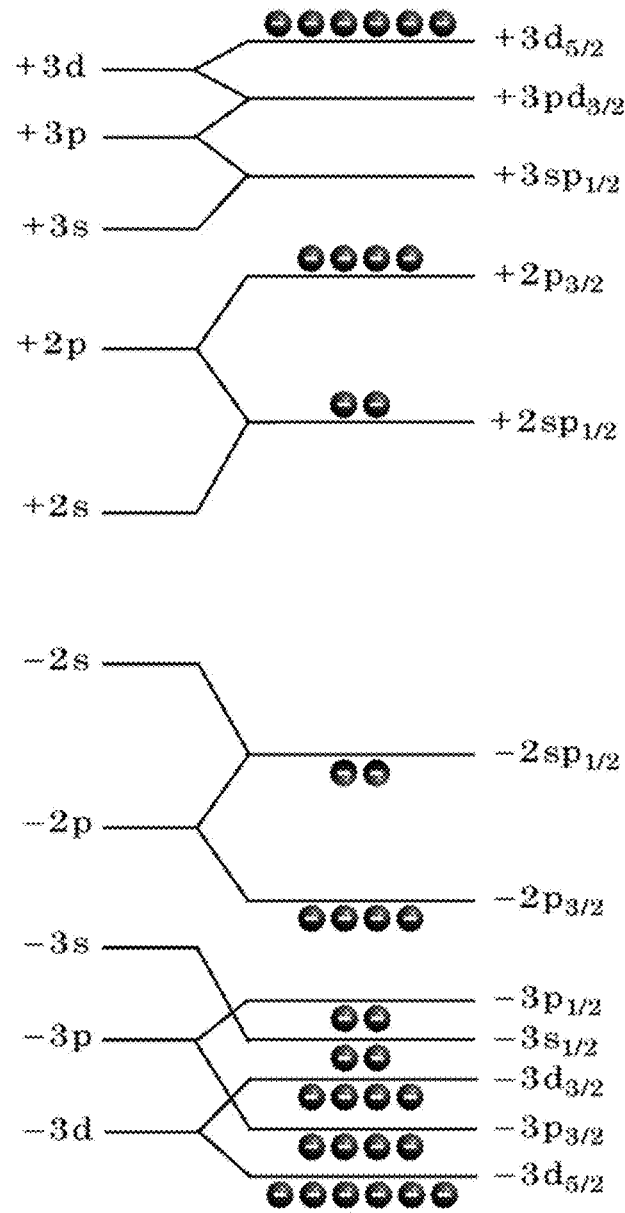
FIG. 61 is an energy level diagram depicting the occupied energy levels believed to be characteristic of picocrystalline silaborane $(B_{12}H_4)_3Si_5$ prior to disproportionation.

It is believed that all bonding energy levels in FIG. 61 are disentangled except for the $-2sp_{1/2}$ energy level. As discussed hereinabove, picocrystalline silaborane $(B_{12}H_4)_3Si_5$ exhibits a high electronegativity and, therefore, exhibits the strong tendency to undergo a disproportionation in which a pair of valence electrons is transferred from one picocrystalline artificial borane atom 101 to a neighboring picocrystalline artificial borane atom 101. By virtue of disproportionation, a picocrystalline artificial borane atom $B_{12}H_4$ 101 is positively ionized into a picocrystalline artificial borane atom $B_{12}^{2+}H_4$ 101 by a transfer of a pair of valence electrons to a neighboring picocrystalline artificial borane atom $B_{12}^{2-}H_4$ 101 that is thereby negatively ionized during disproportionation. The believed occupancy of the energy levels by valence electrons in negatively-ionized and positively-ionized picocrystalline artificial borane atoms $B_{12}^{2-}H_4$ and $B_{12}^{2+}H_4$ 101, due to disproportionation in picocrystalline silaborane $(B_{12}H_4)_3Si_5$, are respectively shown in FIGS. 62A-B.

The ionization of picocrystalline artificial borane atoms $B_{12}^{2-}H_4$ or $B_{12}^{2+}H_4$ 101 is due to the ionization of the artificial nuclei $B_{12}^{2-}$ or $B_{12}^{2+}$ without any change in the four artificial valence electrons $H_4$. The ability to ionize an artificial nucleus, without altering the artificial electrons, is responsible for a novel type of atomic engineering of picocrystalline oxysilaborane $(B_{12}H_4)_xSi_yO_z$ over the preferred compositional range ($2 \leq x \leq 4$, $3 \leq y \leq 5$ and $0 \leq z \leq 2$). The electronic closed-shell of the negatively-ionized picocrystalline artificial borane atom $B_{12}^{2-}H_4$ 101 in FIG. 62A ideally exhibits a vanishing electronegativity. Quite differently, the pair of holes of the positively-ionized picocrystalline artificial borane atom $B_{12}^{2+}H_4$ 101 in FIG. 62B exhibits a high electronegativity. It is significant that disproportionation ionizes picocrystalline artificial borane atoms $B_{12}H_4$ 101 into a trace concentration of charged picocrystalline artificial borane atoms $B_{12}^{2-}H_4$ and $B_{12}^{2+}H_4$ 101.

The trace concentration of positively-ionized picocrystalline artificial borane atoms $B_{12}^{2+}H_4$ 101 results in the extrinsic carrier concentration $p_0 \approx 10^{18}$ cm$^{-3}$ of picocrystalline silaborane $(B_{12}H_4)_3Si_5$. This is experimentally verified in Example 13. In this particular example, the acceptor doping of the silicon substrate 421 results an extrinsic carrier concentration of $p_0 \approx 4 \times 10^{18}$ cm$^{-3}$. The extrinsic carrier concentration of the nondegenerate p-type monocrystalline silicon layer 422 is $p_0 \approx 7 \times 10^{15}$ cm$^{-3}$. As a result, mobile holes are injected into the p-type monocrystalline silicon layer 422 from either the silicon substrate 421 or the picocrystalline silaborane $(B_{12}H_4)_3Si_5$ film 426 in Example 13, dependent upon the bias polarity of the anode and cathode electrodes 425 and 424. When the cathode electrode 424 is biased negative relative to the anode electrode 425, mobile holes are injected from the silicon substrate 421 into the p-type monocrystalline silicon layer 422.

Conversely, when the cathode electrode 424 is biased positive relative to the anode electrode 425, mobile holes are injected from the picocrystalline silaborane $(B_{12}H_4)_3Si_5$ film 426 into the p-type monocrystalline silicon layer 422. Referring now to the impedance characteristics in FIG. 55, it can be observed that the impedance of the electrochemical device 420 in Example 13 is approximately symmetrical with respect to the bias polarity such that no rectification exists. This condition is significantly altered in Example 12. By referring to FIGS. 49-53, it can be seen that that the incorporation of oxygen in the picocrystalline oxysilaborane $(B_{12}{}^{2-}H_4)_4Si_4O_2{}^{2+}$ film 423 causes the electrochemical device 420 in Example 12 to exhibit a high degree of rectification in comparison to the electrochemical device 420 in Example 13. The current in the electrochemical devices 420 in Examples 10-13 is a space-charge-limited drift current.

Figure 63:
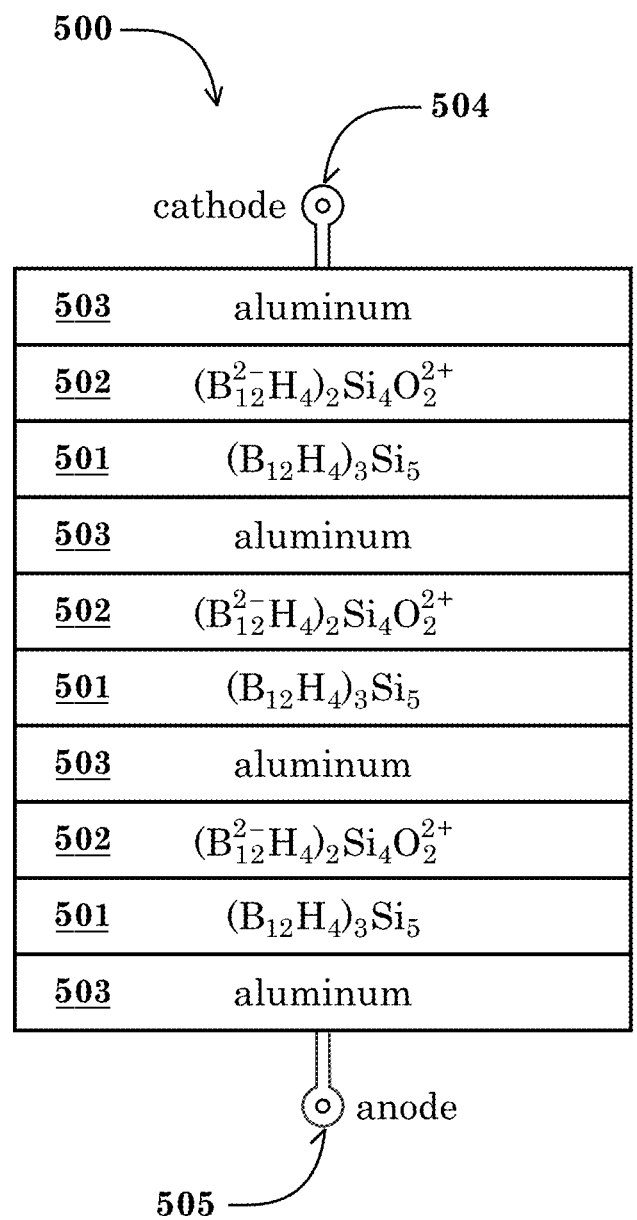
FIG. 63 depicts a thermophotovoltaic diode comprising multiple pairs of conjoined picocrystalline silaborane $(B_{12}H_4)_3Si_5$ regions and picocrystalline oxysilaborane $(B_{12}^{2-}H_4)_4Si_4O_2^{2+}$ regions intervened by aluminum regions.

The utility of the atomic engineering of picocrystalline artificial borane atoms 101 in picocrystalline silaborane $(B_{12}H_4)_3Si_5$ and picocrystalline oxysilaborane $(B_{12}{}^{2-}H_4)_4Si_4O_2{}^{2+}$ can be better understood by considering the believed operation of the thermophotovoltaic diode 500 in FIG. 63. The thermophotovoltaic diode 500 is comprised of an arbitrary number of multiple pairs of conjoined picocrystalline silaborane $(B_{12}H_4)_3Si_5$ regions 501 and picocrystalline oxysilaborane $(B_{12}{}^{2-}H_4)_4Si_4O_2{}^{2+}$ regions 502 intervened by aluminum regions 503. The atomic engineering of the picocrystalline artificial borane atoms 101 constituting the picocrystalline silaborane $(B_{12}H_4)_3Si_5$ regions 501 and picocrystalline oxysilaborane $(B_{12}{}^{2-}H_4)_4Si_4O_2{}^{2+}$ regions 502 can be understood by very briefly considering a generalization of the molecular orbital analysis by Longuet-Higgins and Roberts in their paper "The Electronic Structure of an Icosahedron of Boron," *Proceedings of the Royal Society A*, Vol. 230, 1955, p. 110.

An isolated natural boron atom possesses 3 valence electrons distributed amongst 4 orthonormal atomic orbitals: $\psi_i(s)$, $\psi_i(p_x)$, $\psi_i(p_y)$, and $\psi_i(p_z)$. These 4 orthonormal atomic orbitals are linearly independent of each other. When the 12 natural boron atoms are bonded together by three-center bonds, the atomic orbitals become intertwined, such that they are no longer linearly independent of each other. Although linearly-dependent intertwined atomic orbitals are difficult to analyze, they result in a molecular bond delocalization that supports novel electronic properties not sustainable in any other type of molecule. Following Longuet-Higgins and Roberts, a regular icosahedron is inscribed in a cube in the manner shown in FIG. 64. The golden mean $\varphi$ is ~1.618.

Figure 64:
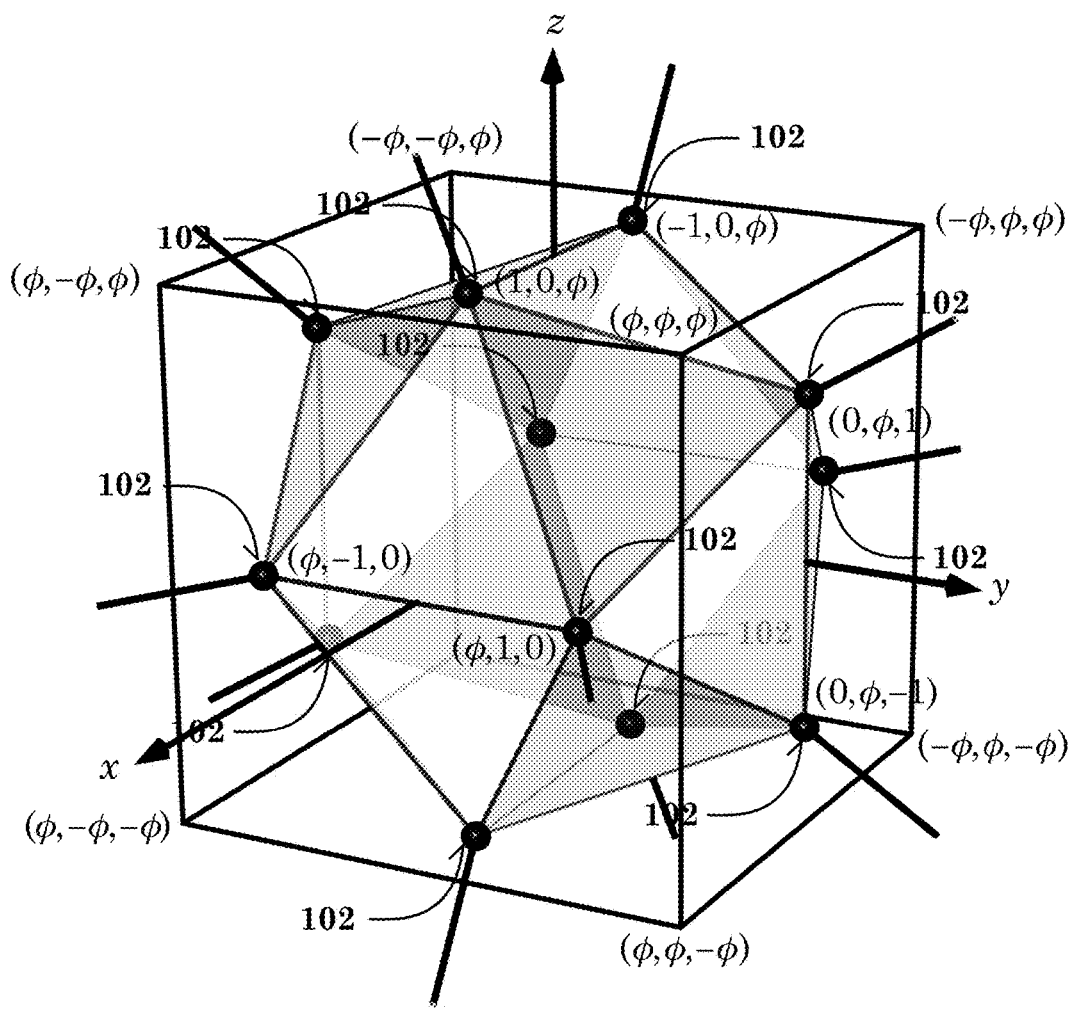
FIG. 64 depicts a regular icosahedron inscribed in a cube in the manner employed by Longuet-Higgins and Roberts.
Figure 65:
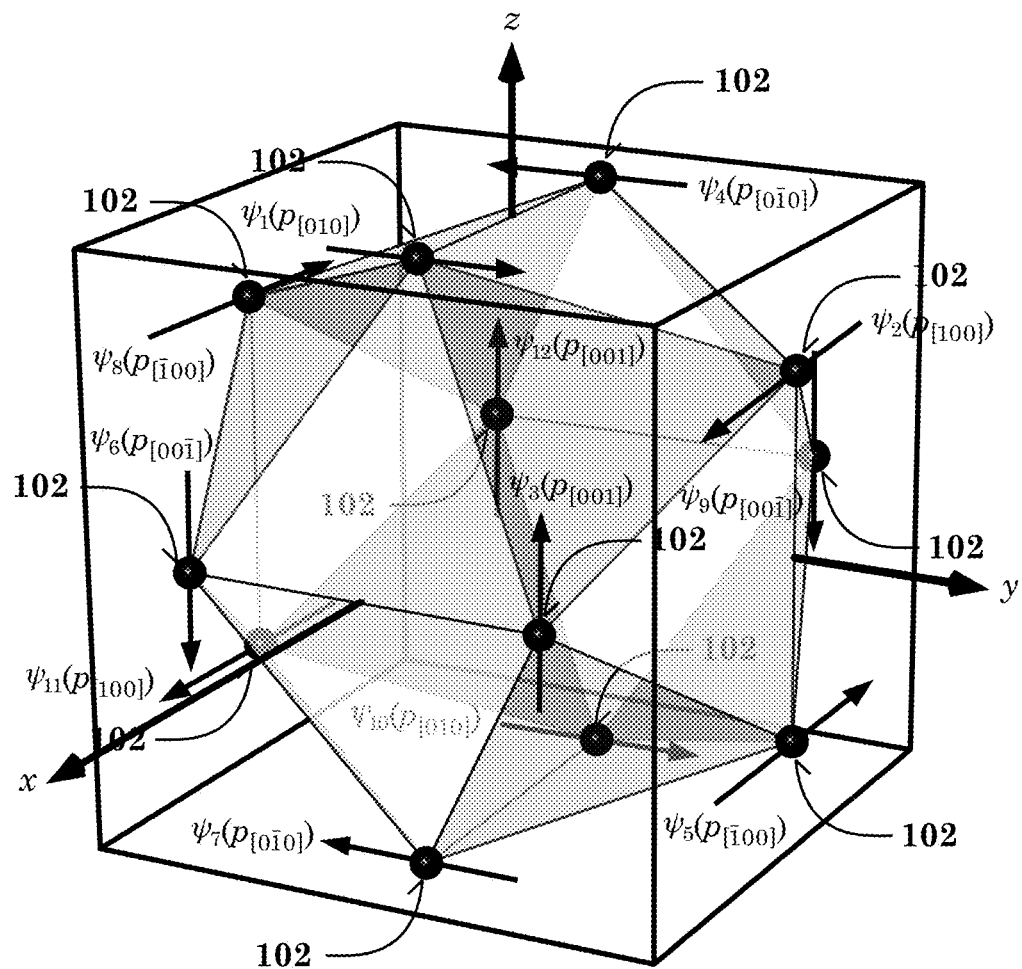
FIG. 65 depicts the 12 tangential atomic orbitals $\psi_i(p_{\{100\}})$ shown in FIG. 3 of the paper by Longuet-Higgins and Roberts, except for a different symbolism.
Figure 66:
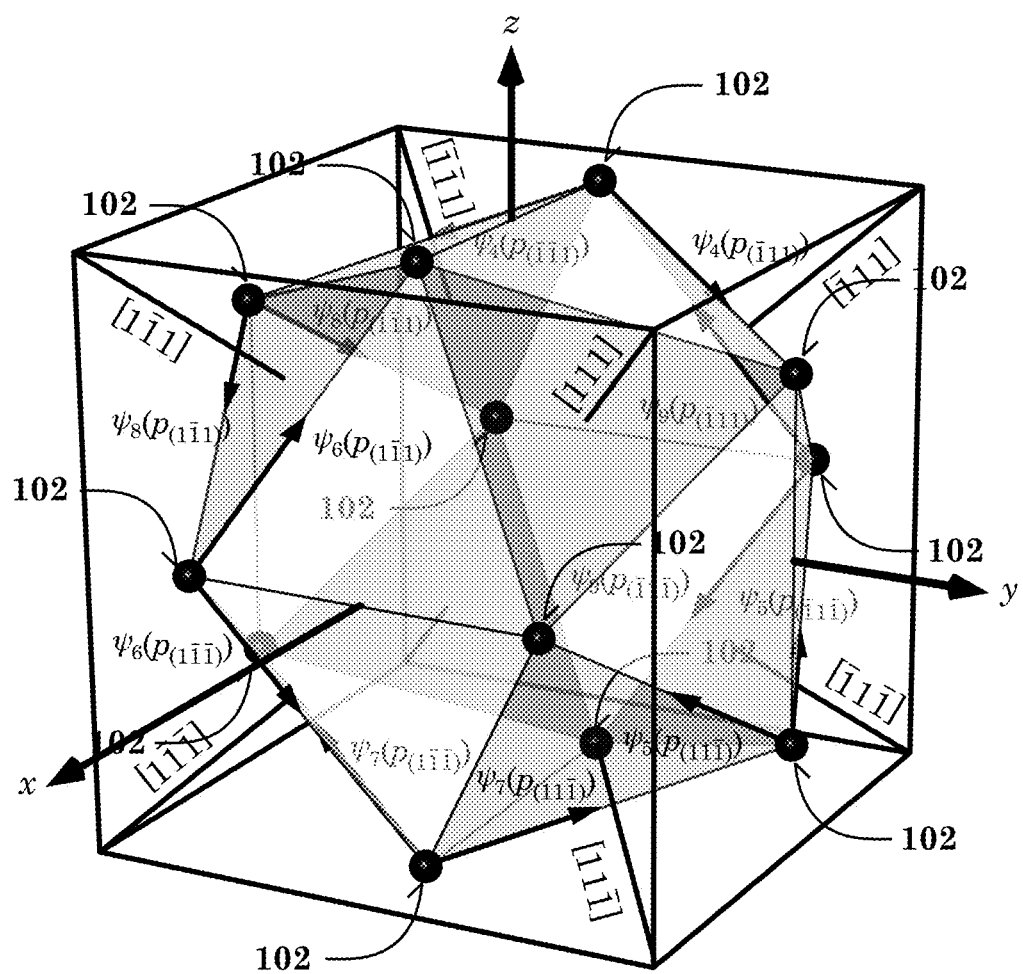
FIG. 66 depicts the 12 tangential atomic orbitals $\psi_i(p_{\{111\}})$ shown in FIG. 2 of the paper by Longuet-Higgins and Roberts, except for a different symbolism.

A natural boron nucleus 102 exists at each icosahedral vertex in FIG. 64. There exist 12 nondirectional atomic orbitals $\psi_i(s)$ and 12 radial atomic orbitals $\psi_i(p_r)$ associated with the 12 boron nuclei in FIG. 64, where i=1, 2, 3, . . . , 12. The 12 radial atomic orbitals $\psi_i(p_r)$ are directed along the 12 icosahedral axes of fivefold rotation. There further exist 24 tangential atomic orbitals. The 12 tangential atomic orbitals $\psi_i(p\langle_{100}\rangle)$ shown in FIG. 65 constitute those in FIG. 3 of the paper by Longuet-Higgins and Roberts, except for a very different symbolism. The 12 tangential atomic orbitals $\psi_i(p_{\{111\}})$ shown in FIG. 66 constitute those in FIG. 2 of the paper by Longuet-Higgins and Roberts, except for the symbolism. As used herein, the circumscribed cube is referred to as the laboratory frame field and the inscribed icosahedron is referred to as the molecular frame field.

Figure 67:
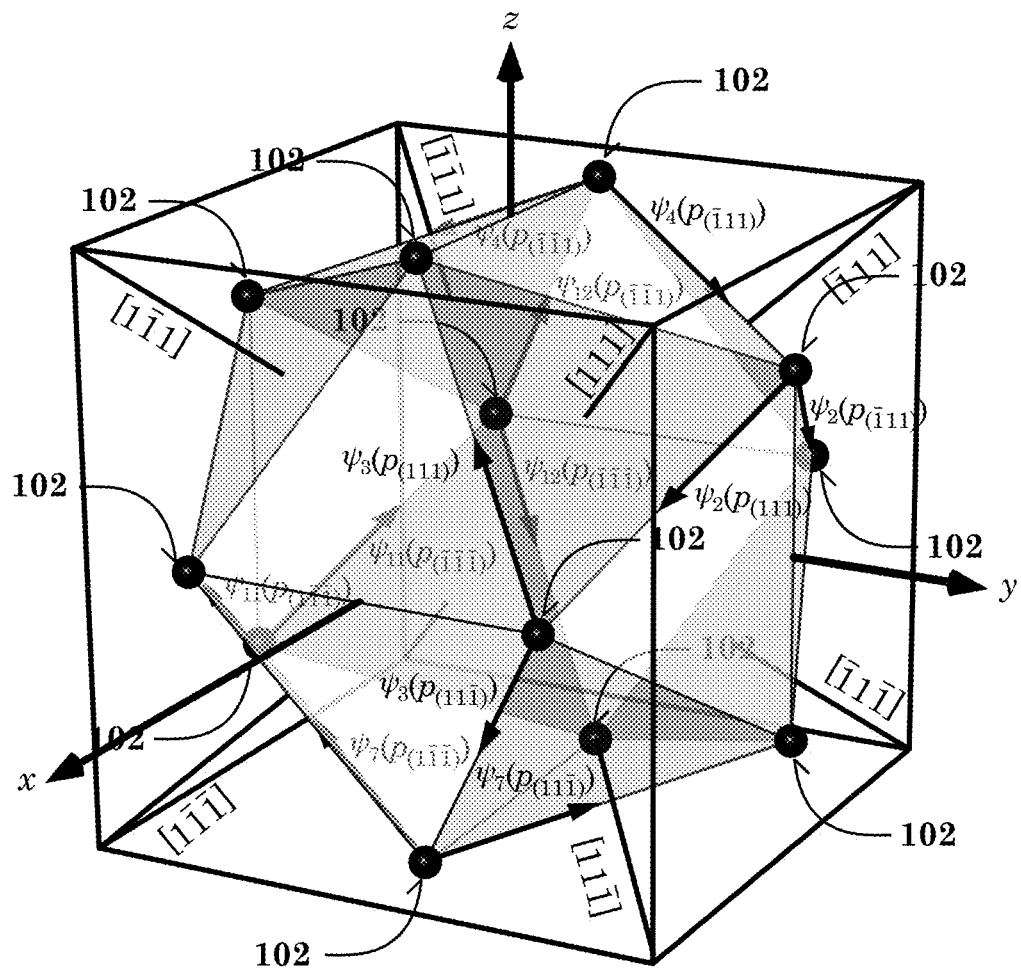
FIGS. 67-69 depict 3 additional delocalized equivalent sets of 12 tangential atomic orbitals $\psi_i(p_{\{111\}})$ that are proposed to exist due to the corotating Cartesian axes in the laboratory frame field of the circumscribed cube.
Figure 68:
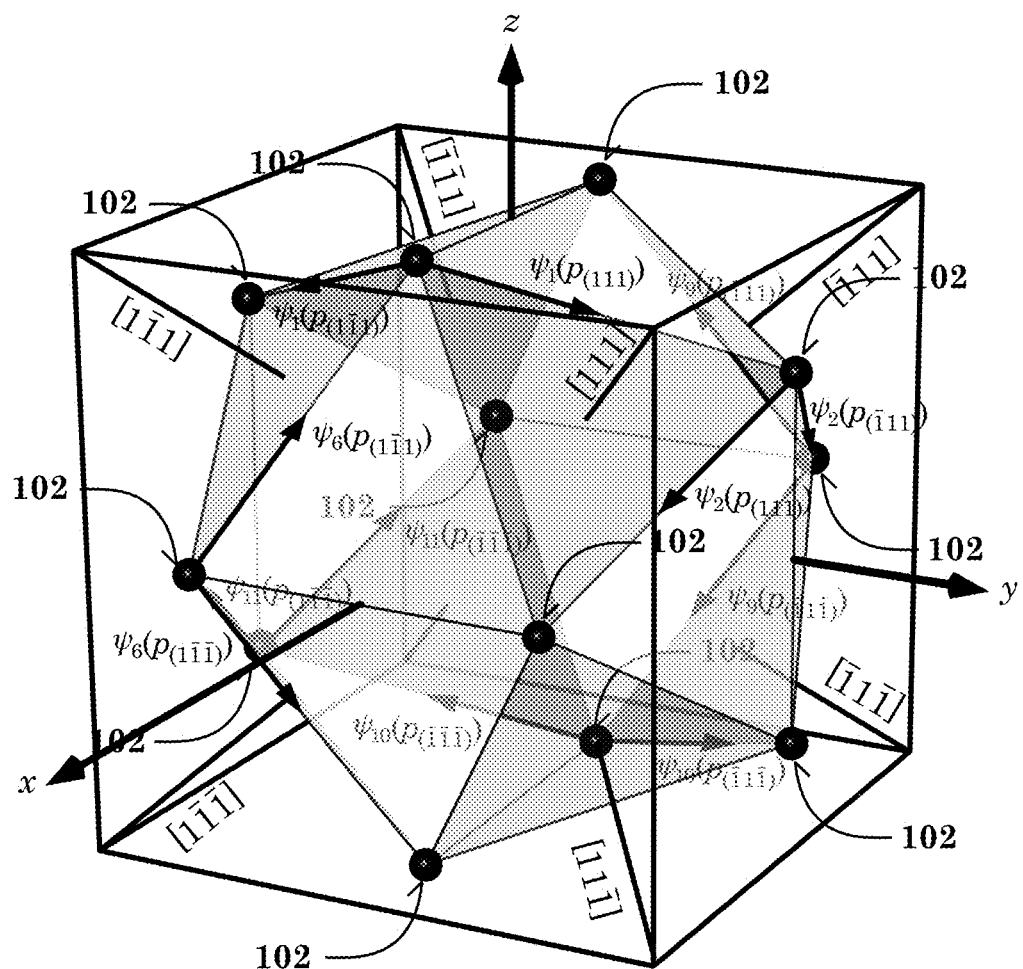
Figure 69:
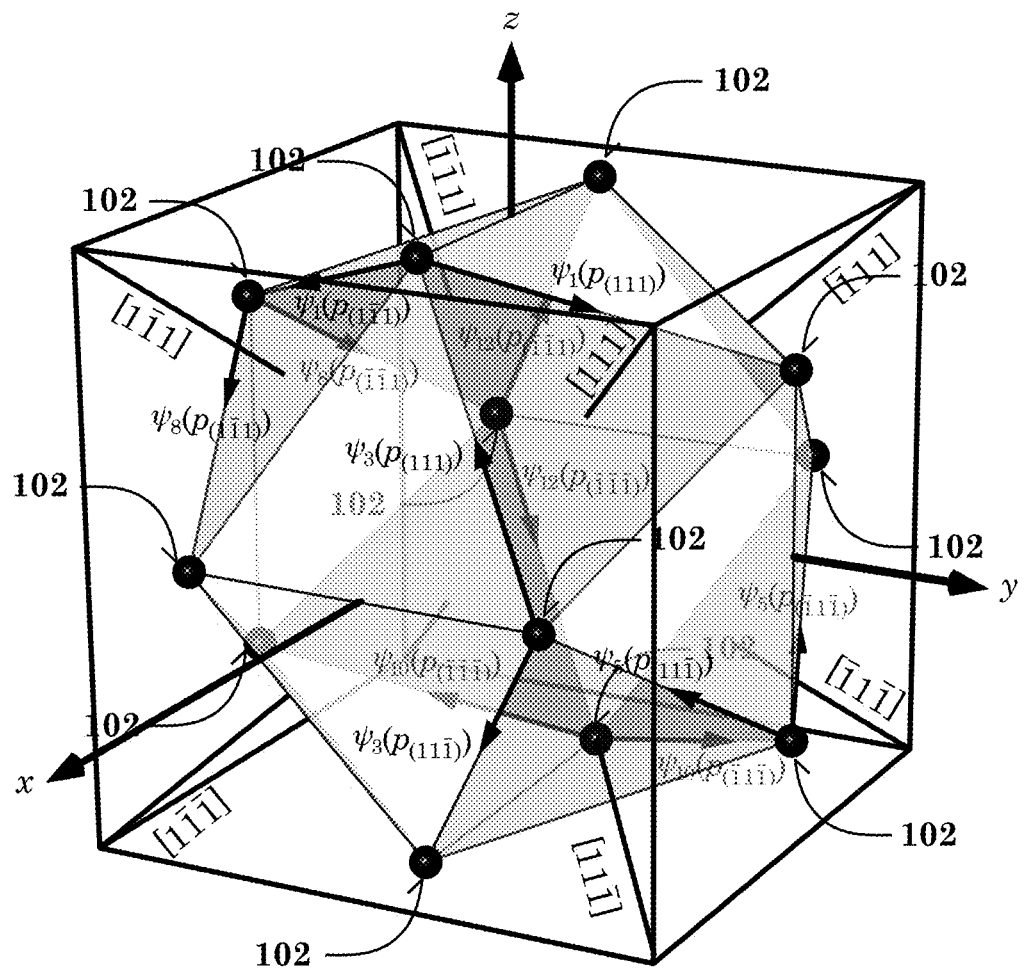

It follows that the 12 tangential atomic orbitals $\psi_i(p\langle_{100}\rangle)$ exist in the laboratory frame field while the 12 tangential atomic orbitals $\psi_i(p_{\{111\}})$ reside in the molecular frame field. This is quite important since the 120 symmetry operations of a regular icosahedron cause all three of the Cartesian axes in the laboratory frame to rotate, such that the displacement of the boron nuclei 102 in response to the 120 symmetry operations of a regular icosahedron cannot be fully described in the laboratory frame field. Due to the corotating Cartesian axes in the laboratory frame field of the circumscribed cube, there exist 3 other delocalized sets of 12 tangential atomic orbitals $\psi_i(p_{\{111\}})$ that are shown in FIGS. 67-69. The existence of 4 delocalized sets of 12 tangential atomic orbitals $\psi_i(p_{\{111\}})$ was not considered by Longuet-Higgins and Roberts in their molecular orbital analysis.

Figure 70:
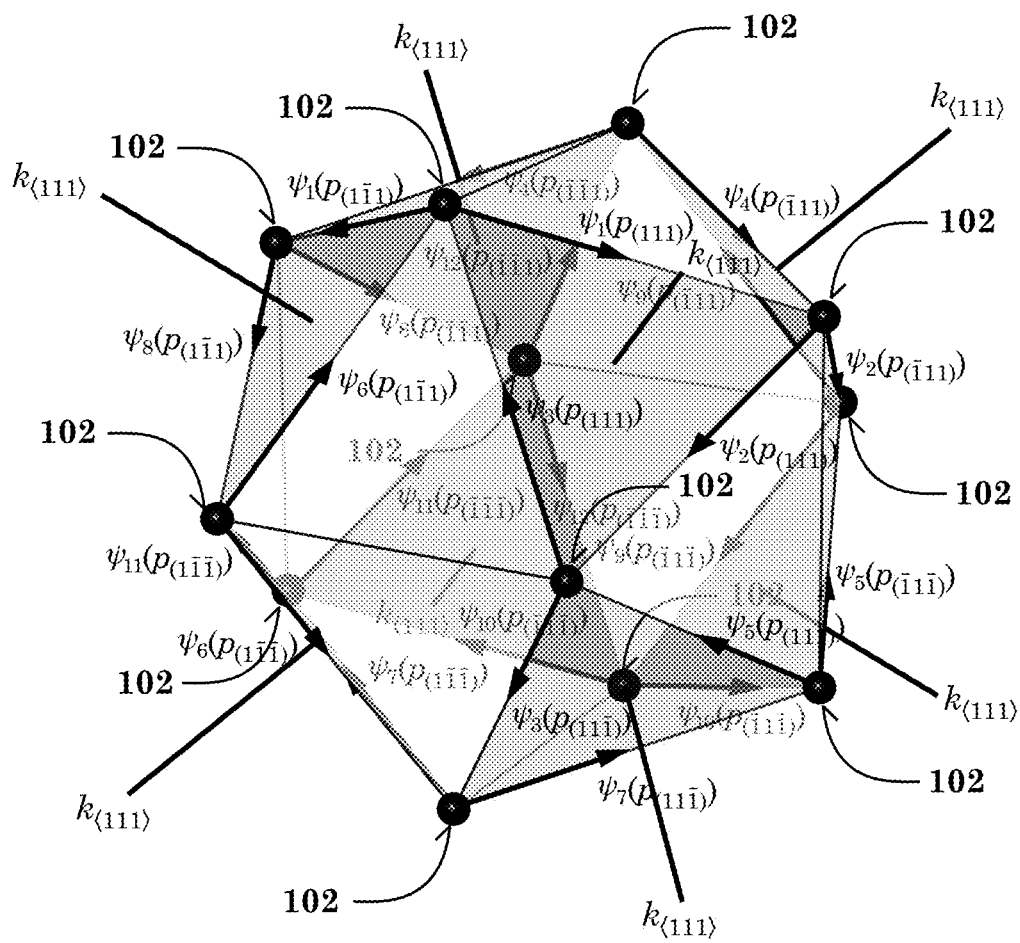
FIG. 70 depicts the proposed nearly-symmetrical nuclear configuration of a boron icosahedron wherein the three-center bonds are described in terms of the 24 delocalized tangential atomic orbitals $\psi_i(p_{\{111\}})$.

The generalization of the molecular orbital analysis by Longuet-Higgins and Roberts, to account for the full impact of the 120 icosahedral symmetry operations on the displacement of the boron nuclei 102, results in the symmetrical nuclear configuration of a boron icosahedron in FIG. 70. The three-center bonds of a boron icosahedron are described in terms of the 24 tangential atomic orbitals $\psi_i(p_{\{111\}})$ shown in FIG. 70. The generalized molecular orbital analysis results in a surprising finding: The 120 icosahedral symmetry operations result in a nearly-symmetrical boron icosahedron in which all 12 boron nuclei 102 are motionless, so as to support periodic rectilinear vibrations along the $k\langle_{111}\rangle$ wave vectors shown in FIG. 70. A possible explanation of this finding is provided when a nearly-symmetrical boron icosahedron is treated as a nearly-spherical spheroid.

The 24 nonorthogonal tangential atomic orbitals $\psi_i(p_{\{111\}})$ shown in FIG. 70 cannot be directly analyzed in terms of the 120 icosahedral symmetry operations. The 24 nonorthogonal tangential atomic orbitals $\psi_i(p_{\{111\}})$ in FIG. 70 are represented in terms of molecular orbitals that can be described in terms of orthogonal irreducible representations of a regular icosahedron. The nearly-twelvefold-degenerate antibonding molecular orbital cluster $\Psi_Y(T_{1g}, G_g, H_u)$ is believed to be associated with: 1) the threefold-degenerate icosahedral irreducible representation $T_{1g}$, (2) the fourfold-degenerate icosahedral irreducible representation $G_g$, and also (3) the fivefold-degenerate icosahedral irreducible representation $H_u$. These three icosahedral irreducible representations are strictly associated with the surface spherical harmonics of an icosahedron.

In a like way, the nearly-twelvefold-degenerate bonding molecular orbital cluster of electrons $\Psi_Y(T_{1u}, G_u, H_g)$ is believed to be associated with: 1) the threefold-degenerate icosahedral irreducible representation $T_{1u}$, (2) the fourfold-degenerate icosahedral irreducible representation $G_u$, and also (3) the fivefold-degenerate icosahedral irreducible representation $H_g$. Whereas the fourfold-degenerate icosahedral irreducible representation $G_u$ is associated with surface spherical harmonics of an icosahedron, the threefold-degenerate icosahedral irreducible representation $T_{1u}$ and fivefold-degenerate icosahedral irreducible representation $H_g$ are, more generally, associated with the radial and surface spherical harmonics of an icosahedron. It is believed that the nearly-twelvefold-degenerate antibonding molecular orbital cluster of electrons $\Psi_Y(T_{1g}, G_g, H_u)$ is ideally associated with +2s, +2p, +3s, +3p, +3d energy levels in FIG. 60. It is believed that the conjugated nearly-twelvefold-degenerate bonding molecular orbital cluster of 12 electrons $\Psi_Y(T_{1u}, G_u, H_g)$ is associated with −2s, −2p, −3s, −3p, −3d energy levels in FIG. 60.

Figure 71:
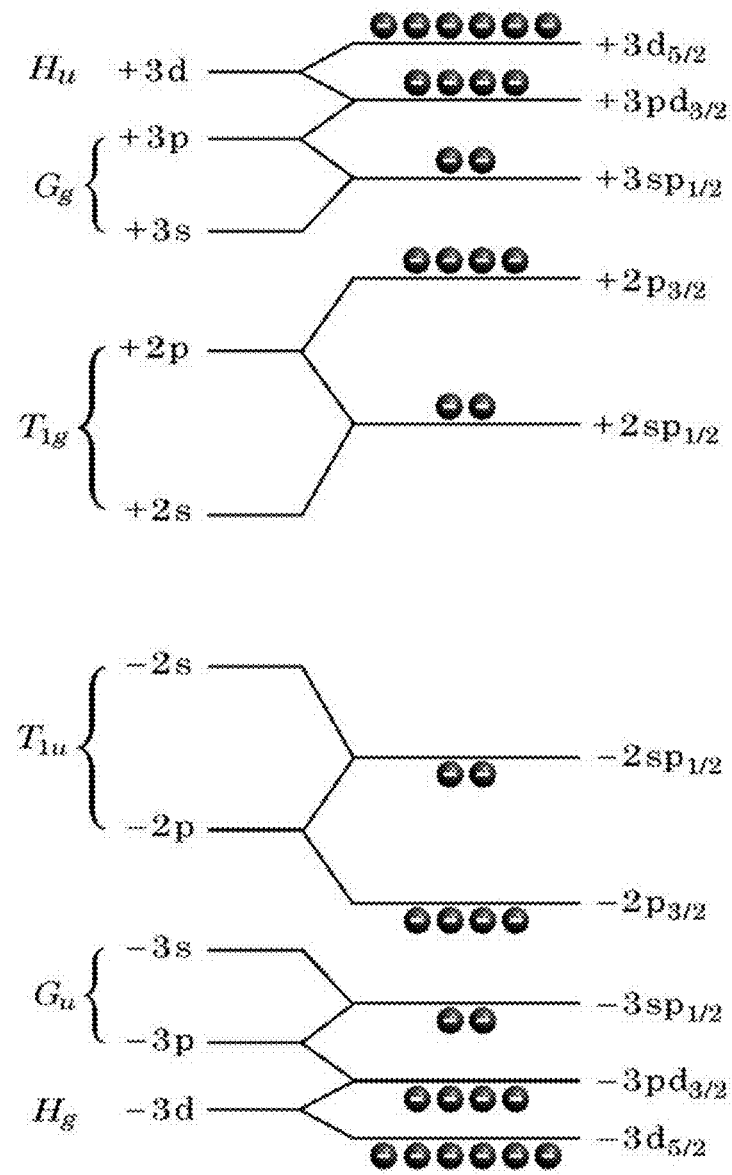
FIG. 71 depicts an energy diagram showing the proposed energy levels of the clustered valence electrons of the regular boron icosahedron shown in FIG. 70.

The above-described clustering of valence electron energy levels in a regular boron icosahedron is portrayed in FIG. 71. The whole-integer-quantized energy levels are lifted by spin-orbit coupling into half-integer-quantized energy levels in the manner shown in FIG. 71. It is to be understood that the actual separation of energy levels is exaggerated in FIG. 71. There is a good reason for representing the energy levels of a regular boron icosahedron in terms of the icosahedral irreducible representations. The 120 symmetry operations of a regular icosahedron are unique in that they cause the rotation of the Cartesian axes in the laboratory frame field of the circumscribed cube in FIG. 64. As a result, a rotation and translation of the boron nuclei 102 cannot be described in terms of the threefold-degenerate Cartesian axes, along which the 12 tangential atomic orbitals $\psi_i(p\langle_{100}\rangle)$ are parallel. This is remedied by representing the 24 tangential atomic orbitals $\psi_i(p_{\{111\}})$ by the threefold-degenerate icosahedral irreducible representation $T_{1g}$ associated with rotation and the threefold-degenerate icosahedral irreducible representation $T_{1u}$ associated with translation.

By so doing, it was proven that the 120 symmetry operations of a regular icosahedron result in no icosahedral rotation and confine all icosahedral translation along the rectilinear axes of the $k\langle_{111}\rangle$ wave vectors shown in FIG. 70. This is particularly surprising in that the 24 tangential atomic orbitals $\psi_i(p_{\{111\}})$ in FIG. 70 are represented by normalized vectors constrained to the boron nuclei 102, which are themselves motionless. All icosahedral displacement is ideally confined to the 4 rectilinear axes connecting the opposite pairs of icosahedral faces normal to the $k\langle_{111}\rangle$ wave vectors in FIG. 70. This condition actually makes sense since the peak electron density of the three-center chemical bonds, comprised by the 24 tangential atomic orbitals $\psi_i(p_{\{111\}})$ in FIG. 70, ideally resides at the geometric center of the 8 {111} icosahedral faces shown in FIG. 70.

The valence electrons in the antibonding intraicosahedral orbitals of a regular boron icosahedron are within the nearly-twelvefold-degenerate molecular orbital cluster $\Psi_Y(T_{1g}, G_g, H_u)$ while the valence electrons in the bonding intraicosahedral orbitals of a regular boron icosahedron are within the nearly-twelvefold-degenerate molecular orbital cluster $\Psi_Y(T_{1u}, G_u, H_g)$. The nearly-twelvefold-degenerate antibonding molecular orbital cluster $\Psi_Y(T_{1g}, G_g, H_u)$ of valence electrons is believed to support a delocalized peak electron density near the geometric center of the 4 {111} icosahedral faces normal to the $k\langle_{111}\rangle$ wave vectors of the picocrystalline artificial borane atom 101 in FIG. 9. The nearly-twelvefold-degenerate bonding molecular orbital cluster $\Psi_Y(T_{1u}, G_u, H_g)$ of valence electrons is believed to support a delocalized peak electron density at the geometric center of the opposite {111} icosahedral faces of the picocrystalline artificial borane atom 101 in FIG. 9.

In this manner, the positive-definite half-integer-quantized energy levels in FIG. 71 are associated with the lifting of the nearly-twelvefold-degenerate antibonding molecular orbitals $\Psi_Y(T_{1g}, G_g, H_u)$ by spin-orbit coupling. In a like way, the negative-definite half-integer-quantized energy levels in FIG. 71 are associated with a lifting of the nearly-twelvefold-degenerate bonding molecular orbitals $\Psi_Y(T_{1u}, G_u, H_g)$ by spin-orbit coupling. The lifting of the orbital degeneracies by spin-orbit coupling per FIG. 71 maintains a charge-conjugation symmetry pursuant to Dirac's relativistic wave equation. It is significant that the 36 valence electrons in FIG. 71 are associated with the chemical bonding of the artificial nucleus $B_{12}$ of a neutral picocrystalline artificial borane atom $B_{12}H_4$ 101. It is further significant that the 18 valence electrons in the half-integer-quantized antibonding intraicosahedral energy levels in FIG. 71 are associated with icosahedral rotation $T_{1g}$ while the 18 valence electrons in the half-integer-quantized bonding intraicosahedral energy levels in FIG. 71 are associated with icosahedral translation $T_{1u}$.

The 18 valence electrons in the half-integer-quantized, positive-definite antibonding energy levels and the 18 valence electrons in the half-integer-quantized, negative-definite bonding energy levels exist near the geometric center of opposite icosahedral faces amongst the delocalized pairs of icosahedral faces normal to the 4 $k\langle_{111}\rangle$ wave vectors of the picocrystalline artificial borane atom 101 in FIG. 9. The delocalization of valence electrons in half-integer-quantized energy levels gives rise to a type of atomic engineering that is novel to the picocrystalline oxysilaboranes of this invention. This type of atomic engineering is not possible in the fullerenes, since the molecular truncation of buckminsterfullerene eliminates any bond delocalization due to the fivefold rotation of a regular icosahedron. This type of atomic engineering is not possible in the boron-rich solids in the prior art since the boron icosahedra are deformed by Jahn-Teller distortions.

Figure 72:
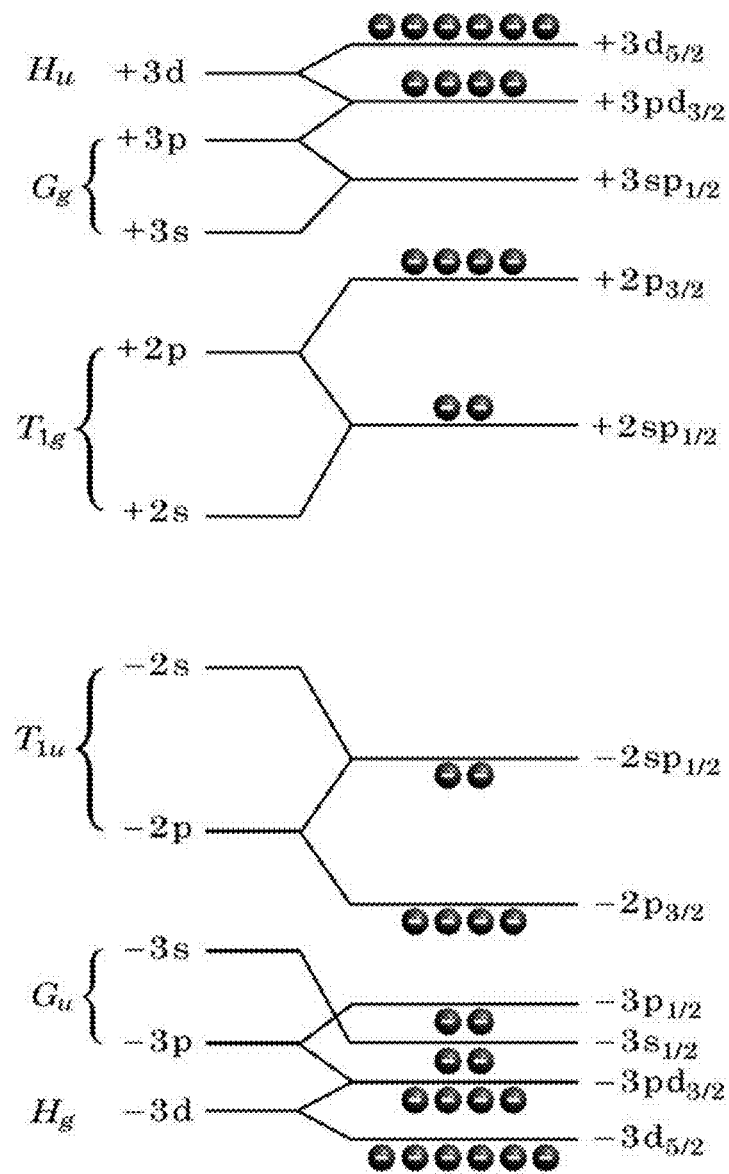
FIG. 72 depicts an energy diagram illustrating a proposed first disentanglement of the $-3sp_{1/2}$ energy level into the $-3s_{1/2}$ and $-3p_{1/2}$ energy levels, such that a pair of electrons fall from the $+3sp_{1/2}$ energy level.

There are two different elementary types of atomic engineering of the picocrystalline oxysilaboranes of this invention. One elementary type of atomic engineering involves the absence of any significant trace impurity, such that charge-conjugate symmetry is broken between the half-integer-quantized energy levels within the artificial nuclei $B_{12}$ of neutral picocrystalline artificial borane atoms $B_{12}H_4$ 101 per FIG. 61. Charge-conjugation symmetry is believed to be broken in an orderly manner by an ordered disentanglement of the half-integer-quantized bonding energy levels within the artificial nucleus $B_{12}$ of a neutral picocrystalline artificial borane atom $B_{12}H_4$ 101. It is believed that the $-3sp_{1/2}$ energy level is first disentangled into the $-3s_{1/2}$ and $-3p_{1/2}$ energy levels, such that a pair of electrons fall from the $+3sp_{1/2}$ energy level in the manner shown in FIG. 72. It is believed that the $-3pd_{3/2}$ energy level is thereafter disentangled into the $-3p_{3/2}$ and $-3d_{3/2}$ energy levels, such that two electrons fall from the $+3pd_{3/2}$ energy level in the manner shown in FIG. 73.

Figure 73:
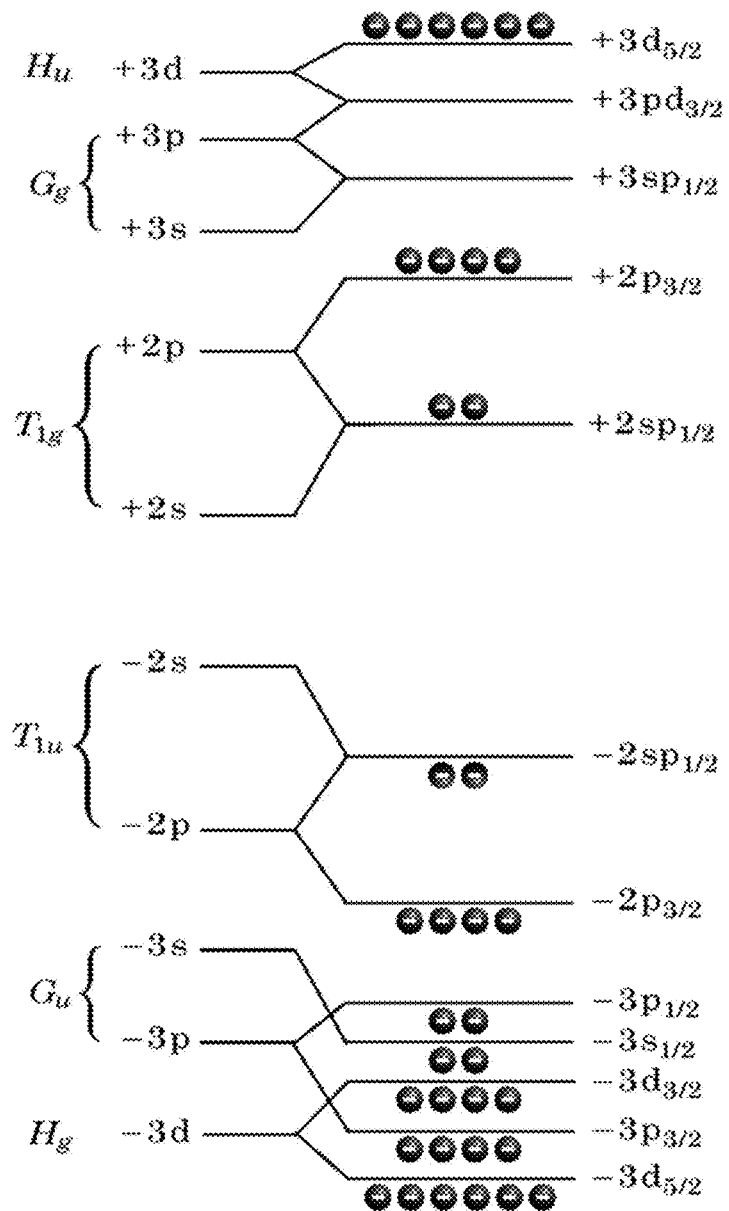
FIG. 73 depicts an energy diagram illustrating a second proposed disentanglement of the $-3pd_{3/2}$ energy level into the $-3p_{3/2}$ and $-3d_{3/2}$ energy levels, such that four electrons fall from the $+3pd_{3/2}$ energy level.

It is believed that the valence electron configuration in FIG. 73 is characteristic of the artificial nucleus of a neutral picocrystalline artificial borane atom $B_{12}H_4$ 101. Before discussing the utility of such a valence electron configuration, a possible explanation of the difference in the disentanglement of the half-integer-quantized antibonding and bonding energy levels in FIG. 73 is first provided. The threefold-degenerate $T_{1g}$, fourfold-degenerate $G_g$ and fivefold-degenerate $H_u$ icosahedral irreducible representations of the positive-definite antibonding energy levels in FIG. 73 are all associated with strictly the surface spherical harmonics. Very differently, the threefold-degenerate $T_{1u}$ and fivefold-degenerate $H_g$ icosahedral irreducible representations of the positive-definite antibonding energy levels in FIG. 73 are associated with both radial and surface spherical harmonics, such that a disentanglement due to a radial harmonic can occur.

Figure 74:
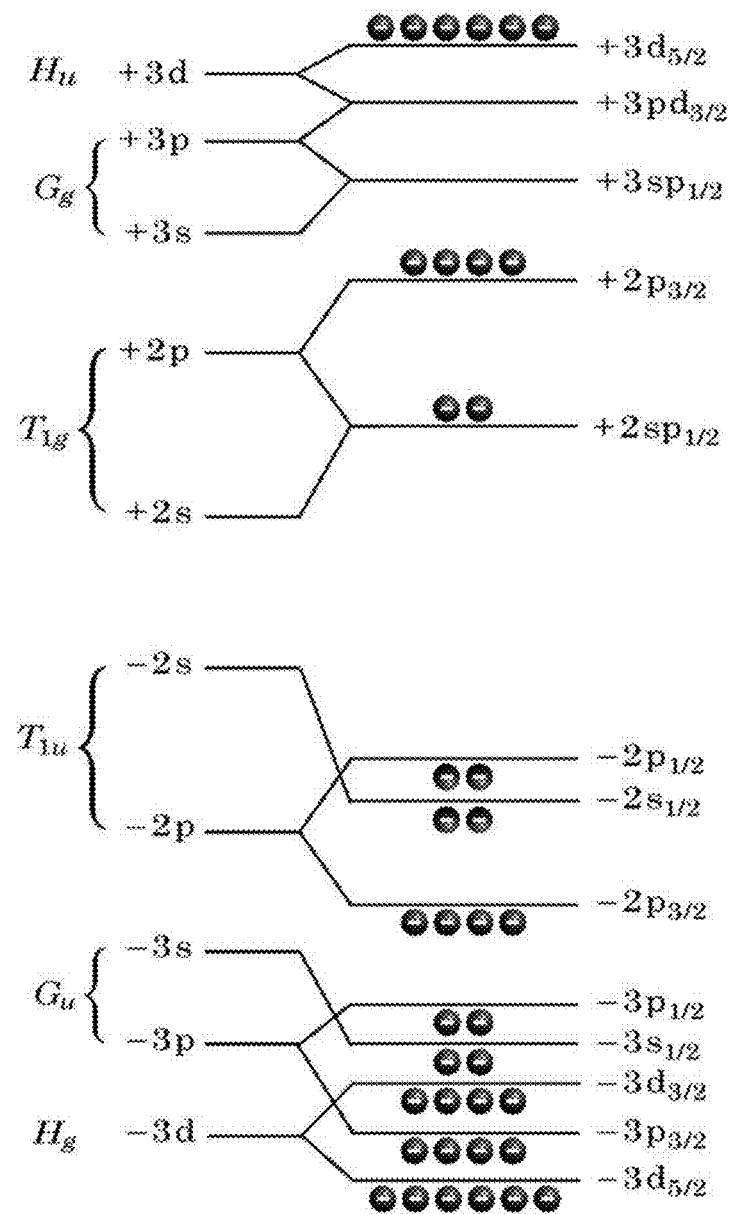
FIG. 74 depicts an energy diagram illustrating the proposed disentanglement of the $-2sp_{1/2}$ energy level in FIG. 62A.

The impact of the radial spherical harmonics can be understood in conjunction with the disproportionation of neutral picocrystalline artificial borane atoms $B_{12}H_4$ 101 into equal pairs of dianions $B_{12}{}^{2-}H_4$ 101 and dications $B_{12}{}^{2+}H_4$ 101 in the manner represented in FIGS. 62A-B. The disentanglement of the $-2sp_{1/2}$ energy level in FIG. 62A is more fully represented in FIG. 74. The disproportionation of neutral picocrystalline artificial borane atoms $B_{12}H_4$ 101 into equal pairs of dianions $B_{12}{}^{2-}H_4$ 101 and dications $B_{12}{}^{2+}H_4$ 101 occurs in the picocrystalline silaborane $(B_{12}H_4)_3Si_5$ regions 501 of the thermophotovoltaic diode 500 in FIG. 63. Picocrystalline artificial borane atoms $B_{12}{}^{2-}H_4$ 101 are negatively ionized in picocrystalline oxysilaborane $(B_{12}{}^{2-}H_4)_4Si_4O_2{}^{2+}$ regions 502 of the thermophotovoltaic diode 500 shown in FIG. 63.

The occupied electronic energy levels of the artificial nuclei of the first- and second-nearest neighbor picocrystalline artificial borane atoms 101 of a pair of conjoined picocrystalline silaborane $(B_{12}H_4)_3Si_5$ and picocrystalline oxysilaborane $(B_{12}{}^{2-}H_4)_4Si_4O_2{}^{2+}$ regions 501 and 502 are respectively shown in shown in FIGS. 75A-D relative to the metallurgical junction between said conjoined regions 501 and 502. It is emphasized that the occupied energy levels of the artificial nuclei $B_{12}{}^{2-}$ of negatively-ionized picocrystalline artificial borane atoms $B_{12}^{2-}H_4$ 101, comprising the picocrystalline oxysilaborane $(B_{12}^{2-}H_4)_4Si_4O_2^{2+}$ region 502, support a vanishing electronegativity in the ideal limit. Very differently, the occupied energy levels of the artificial nuclei $B_{12}$ of the neutral picocrystalline artificial borane atoms $B_{12}H_4$ 101, forming the conjoined picocrystalline silaborane $(B_{12}H_4)_3Si_5$ region 501, support the capture of electrons due to a high electronegativity.

As discussed above, the trace concentration $p_0 \approx 10^{18}$ cm$^{-3}$ of neutral picocrystalline artificial borane atoms $B_{12}H_4$ 101 in a picocrystalline silaborane $(B_{12}H_4)_3Si_5$ region 501 undergo a disproportionation into neighboring pairs of ionized picocrystalline artificial borane atoms $B_{12}^{2-}H_4$ and $B_{12}^{2+}H_4$ 101. The occupied electronic energy levels of the artificial nuclei $B_{12}^{2-}$ and $B_{12}^{2+}$ of certain neighboring picocrystalline artificial borane atoms $B_{12}^{2-}H_4$ and $B_{12}^{2+}H_4$ 101 within a picocrystalline silaborane $(B_{12}H_4)_3Si_5$ region 501 are represented in FIGS. 76A-B. It bears emphasizing that the energy levels shown in FIGS. 76A-B represent a trace concentration $p_0 \approx 10^{18}$ cm$^{-3}$ responsible for a charge conduction in the thermophotovoltaic diode 500. Due to the high electronegativity of the artificial nucleus $B_{12}^{2+}$ in FIG. 76B and the low electronegativity of the artificial nucleus $B_{12}^{2-}$ in FIG. 76C, mobile charge diffusion spontaneously occurs in the manner shown in FIGS. 77A-D.

Figures 77A, 77B, 77C, 77D:
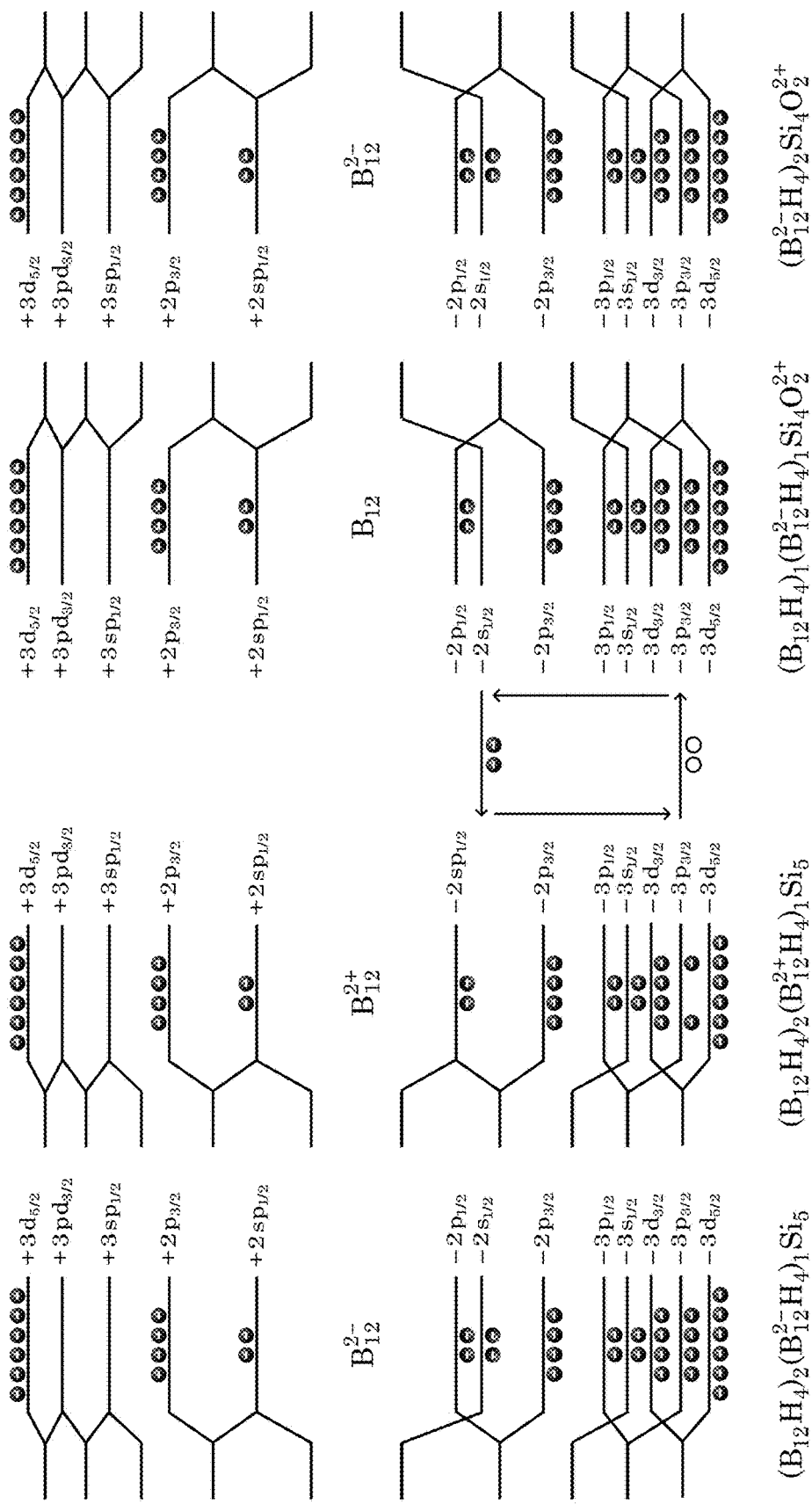
FIGS. 77A-D depicts a proposed spontaneous mobile charge diffusion mechanism.

A pair of mobile holes spontaneously diffuses from the artificial nucleus $B_{12}^{2+}$ in FIG. 77B towards the artificial nucleus $B_{12}$ in FIG. 77C while also, at the same time, a pair of mobile electrons spontaneously diffuses from the artificial nucleus $B_{12}$ in FIG. 77C towards the artificial nucleus $B_{12}^{2+}$ in FIG. 77B. It is believed that the entanglement of the $-2sp_{1/2}$ energy level in FIG. 77B causes the diffused mobile holes and mobile electrons in FIGS. 77A-D to exist in two different discrete energy levels. By way of convention, the pair of electrons diffusing from the $-2s_{1/2}$ energy level in FIG. 77C is represented by $|-2s_{1/2}^2\rangle$ and, in a similar manner, the pair of holes diffusing from the $-3p_{3/2}$ energy level in FIG. 77B is represented by $|-3p_{3/2}^2\rangle$. The latter convention exploits the fact that, when completely occupied by 4 electrons, the $-3p_{3/2}^2$ energy level in FIG. 77B would be represented by $|-3p_{3/2}^4\rangle$. It follows that $|-3p_{3/2}^2\rangle$ represents a pair of missing electrons, and thus a pair of holes, in the $-3p_{3/2}$ energy level in FIG. 77B.

The existence of a pair of mobile electrons $|-2s_{1/2}^2\rangle$ and a pair of mobile holes $|-3p_{3/2}^2\rangle$ in two different energy levels, separated by a microwave energy difference, supports a novelty and utility of preferred embodiments of this invention. This can be better comprehended by considering the occupied energy levels in FIGS. 78A-D. The mobile holes $|-3p_{3/2}^2\rangle$ diffusing from the artificial nucleus $B_{12}^{2+}$ in FIG. 77B fall down into the $-2s_{1/2}$ energy level so as to result in the pair of mobile holes $|-2s_{1/2}^0\rangle$ shown in FIG. 78C while, at the same time, mobile electrons $|-2s_{1/2}^2\rangle$ diffusing from the artificial nucleus $B_{12}$ in FIG. 77C are elevated into the $-3p_{3/2}$ energy level so as to give rise to a quasi-stable tetrad of electrons $|-3_{3/2}^4\rangle$ shown in FIG. 78B. The elevation of the two electrons into the $-3p_{3/2}$ energy level is believed due to the entangled $-2sp_{1/2}$ energy level in FIG. 78B that is believed, in turn, due to intertwined rotational, vibrational, and electronic degrees of freedom.

A disentanglement of the $-2sp_{1/2}$ energy level by spin-orbit coupling necessitates 45 micro-electron-volts of energy. In the absence of any such disentanglement, this energy is believed to be manifested in a vibrational energy along the $k\langle 111\rangle$ wave vectors of the picocrystalline artificial borane atoms 101. The 45 micro-electron-volts thereby corresponds to a vibrational frequency of 10.9 GHz, which is below the maximum frequency (160 GHz) of the cosmic background radiation. Thus, any radiation of a frequency greater than cosmic background radiation is capable of exciting electrons from the entangled $-2sp_{1/2}$ energy level into the disentangled $-3p_{3/2}$ energy level, in the manner represented in FIG. 78B. It warrants mention that terrestrial radiation emitted by the earth is at an infrared frequency which is well above the frequency of the cosmic background radiation. This allows the thermophotovoltaic diode 500 to harvest infrared terrestrial radiation.

The energy levels in FIGS. 78A-D are transformed into those in FIGS. 79A-D due to disproportionation. The cycle described by FIGS. 75A-D through FIGS. 79A-D can, in principle, be indefinitely continued. The continuous cyclic generation of mobile electron-hole pairs $|-2s_{1/2}^2\rangle$ and $|-3p_{3/2}^2\rangle$ in the thermophotovoltaic diode 500 in FIG. 63 causes the diffusion of mobile holes $|-3p_{3/2}^2\rangle$ from each picocrystalline silaborane $(B_{12}H_4)_3Si_5$ region 501, in the form of transformed mobile holes $|-2_{1/2}^0\rangle$, into the conjoined picocrystalline oxysilaborane $(B_{12}^{2-}H_4)_4Si_4O_2^{2+}$ region 502. The diffusion of mobile holes $|-2s_{1/2}^0\rangle$ into the picocrystalline oxysilaborane $(B_{12}^{2-}H_4)_4Si_4O_2^{2+}$ region 502 necessarily results in an accumulated space-charge region with a width of approximately two Debye lengths. Since the Debye length of the picocrystalline oxysilaborane $(B_{12}^{2-}H_4)_4Si_4O_2^{2+}$ region 502 is on the order of approximately 4 nm, then the width of said accumulated space-charge region is 8 nm. The electric current density is determined by the width of the picocrystalline oxysilaborane $(B_{12}^{2-}H_4)_4Si_4O_2^{2+}$ region 502.

If the width of the picocrystalline oxysilaborane $(B_{12}^{2-}H_4)_4Si_4O_2^{2+}$ region 502 is greater than approximately 8 nm, the space-charge-limited drift current density will be similar to that in FIGS. 49-53 of Example 12. Under this condition, no open-circuit voltage can exist between the cathode and anode electrodes 504 and 505 of the thermophotovoltaic diode 500 in FIG. 63. On the other hand, if the width of the picocrystalline oxysilaborane $(B_{12}^{2-}H_4)_4Si_4O_2^{2+}$ regions 502 is smaller than the Debye length (i.e. less than 4 nm), such that the space-charge-limited current is diffusion limited, then an open-circuit voltage between the cathode and anode electrodes 504 and 505 will be generated by the thermophotovoltaic diode 500 in FIG. 63. The thermophotovoltaic diode 500 formed by the picocrystalline oxysilaboranes $(B_{12}H_4)_xSi_yO_z$ over a preferred compositional range ($2 \leq x \leq 4$, $3 \leq y \leq 5$ and $0 \leq z \leq 2$) is novel in that it can transform terrestrial heat radiation directly into electricity in the dark at the ambient temperature by a direct energy transformation.

This novel and useful application of the picocrystalline oxysilaboranes $(B_{12}H_4)_xSi_yO_z$ of the present invention is due to an atomic engineering that supports a controlled variation in the electronegativity of the picocrystalline artificial borane atoms 101 over a preferred compositional range ($2 \leq x \leq 4$, $3 \leq y \leq 5$ and $0 \leq z \leq 2$). Although the particular conjoined regions 501 and 502 of the thermophotovoltaic diode 500 shown in FIG. 63 are picocrystalline silaborane $(B_{12}H_4)_3Si_5$ and picocrystalline oxysilaborane $(B_{12}^{2-}H_4)_4Si_4O_2^{2+}$ respectively, it is to be understood that any two species of picocrystalline oxysilaborane $(B_{12}H_4)_xSi_yO_z$ with a different electronegativity over the preferred compositional range ($2 \leq x \leq 4$, $3 \leq y \leq 5$ and $0 \leq z \leq 2$) could be employed. The novel and useful property of the picocrystalline oxysilaboranes $(B_{12}H_4)_xSi_yO_z$ pertains to the ability to radiatively generate mobile holes and mobile electrons at different microwave energy levels within picocrystalline artificial borane atoms 101 by means of spin-orbit coupling.

Although mobile holes $|-3p_{3/2}^2\rangle$ and mobile electrons $|-2s_{1/2}^2\rangle$ in a thermophotovoltaic diode 500 were associated hereinabove with very specific energy levels separated by more than 45 micro-electron-volts, it is to be understood that mobile holes and mobile electrons more generally exist in discrete energy levels separated by a microwave energy. This capability provides for the operation of a thermophotovoltaic diode, constituted by conjoined picocrystalline oxysilaboranes $(B_{12}H_4)_xSi_yO_z$ of this invention, to ideally operate at an ambient temperature and, more practically, to operate at the ambient temperature of the infrared terrestrial heat radiation emitted by earth. This is very different from a conventional thermophotovoltaic diode.

A conventional thermophotovoltaic diode in the prior art is comprised of a thermal emitter and a photovoltaic diode, with said thermal emitter being typically heated to a temperature above the photovoltaic diode. In a conventional photovoltaic diode, mobile electron-hole pairs are radiatively generated and separated such that mobile electrons are thereby excited into an extended conduction energy band (constituted by a continuum of antibonding molecular orbitals) and mobile holes are excited into an extended valence energy band (constituted by a continuum of bonding molecular orbitals). As used herein, an extended energy band is a large group of antibonding or bonding molecular orbitals respectively behaving as continuum of energy levels extending over a region of space well beyond the first- and second-nearest neighbor natural or artificial atoms, such that mobile electrons are displaced in space at a common energy amongst antibonding molecular orbitals and mobile holes are displaced in space at a different common energy amongst the bonding molecular orbitals. The forbidden energy region between the bottom of the conduction energy band and the top of the valence energy band limits the minimum temperature of the thermal emitter relative to the photovoltaic diode of a conventional thermophotovoltaic diode.

The discrete quantization of energy within the artificial nuclei (constituted by nearly-symmetrical icosahedra with natural boron nuclei 102 residing at the icosahedral vertices) of the picocrystalline artificial borane atoms 101 of this invention allows for an atomic engineering by which mobile holes can exist in different discrete energy levels, separated by a microwave energy, within bonding molecular suborbitals that are confined in space amongst first- and second-nearest neighbor picocrystalline artificial borane atoms 101. By means of this type of atomic engineering, mobile holes and mobile electrons can be generated and separated into discrete energy levels, with a forbidden energy region on the order of 45 micro-electron-volts, so as to be displaced over space at different energy levels. Since the forbidden energy region between discrete energy levels within the artificial nuclei of the picocrystalline artificial borane atoms 101 is on the order of 45 micro-electron-volts, then a continued generation of mobile electron-hole pairs at different energy levels in the picocrystalline artificial borane atoms 101 of the thermophotovoltaic diode 500 in FIG. 63 can occur in response to microwave or infrared radiation in the dark and in thermal equilibrium.

One type of atomic engineering of picocrystalline artificial borane atoms 101 that can support a novel thermophotovoltaic diode capable of harvesting terrestrial radiation was described above. This type of atomic engineering utilizes a breakdown in the charge-conjugation symmetry in the artificial nuclei of picocrystalline artificial borane atoms 101. Another useful type of atomic engineering of the picocrystalline artificial borane atoms 101 maintains the charge-conjugation symmetry of the artificial nuclei. This second type of atomic engineering is achieved by means of the incorporation of a significant impurity atom, such as gold, so as to ideally occupy the energy levels of the picocrystalline artificial borane atoms 101 in the manner represented in FIG. 60. As previously described hereinabove, the 36 valence electrons in FIG. 60 are required to chemically bond the artificial nuclei of the picocrystalline artificial borane atoms 101 forming picocrystalline silaborane $(B_{12}H_4)_3Si_5$:Au and, thus, are not available to support a conduction current.

As used herein, the suffix ":Au" in $(B_{12}H_4)_3Si_5$:Au denotes the trace incorporation of natural gold atoms. The trace concentration of gold atoms in $(B_{12}H_4)_3Si_5$:Au is approximately the same as the extrinsic carrier concentration of $p_0 \approx 10^{18}$ cm$^{-3}$. By introducing oxygen, picocrystalline oxysilaborane $(B_{12}^{2-}H_4)_4Si_4O_2^{2+}$:Au becomes a conductive material with an electrical conductivity that is many orders of magnitude greater than the conductivity of picocrystalline oxysilaborane $(B_{12}^{2-}H_4)_4Si_4O_2^{2+}$. As used herein, the explicit absence of the suffix ":Au" is intended to denote that picocrystalline oxysilaborane $(B_{12}^{2-}H_4)_4Si_4O_2^{2+}$ is void of any detectable concentration of impurity gold atoms. An example of the incorporation of trace gold atoms is now provided.

Example 14

Figure 80:
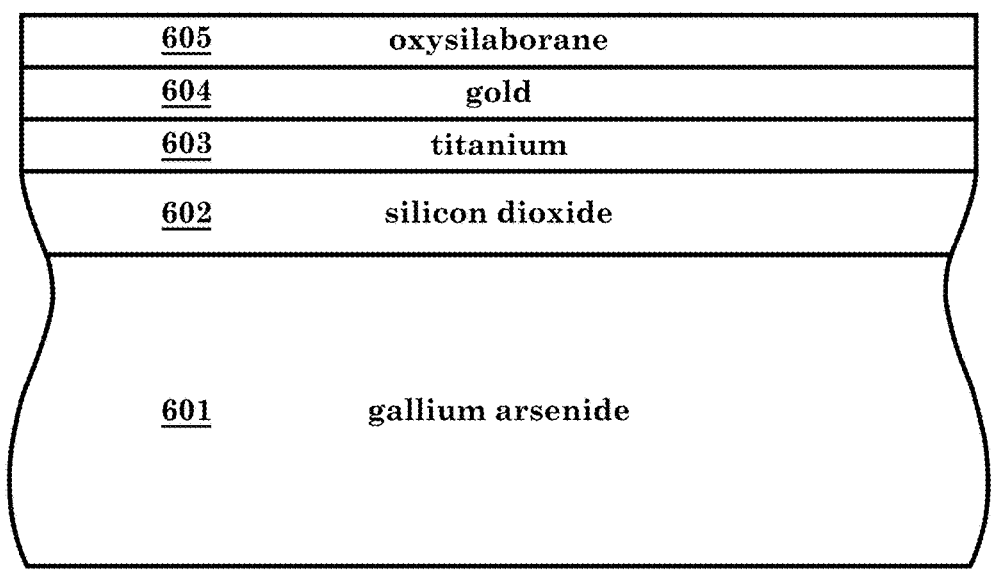
FIG. 80 is an illustration of a device comprising an oxysilaborane film and gold produced in accordance with Example 14.
Figure 81:
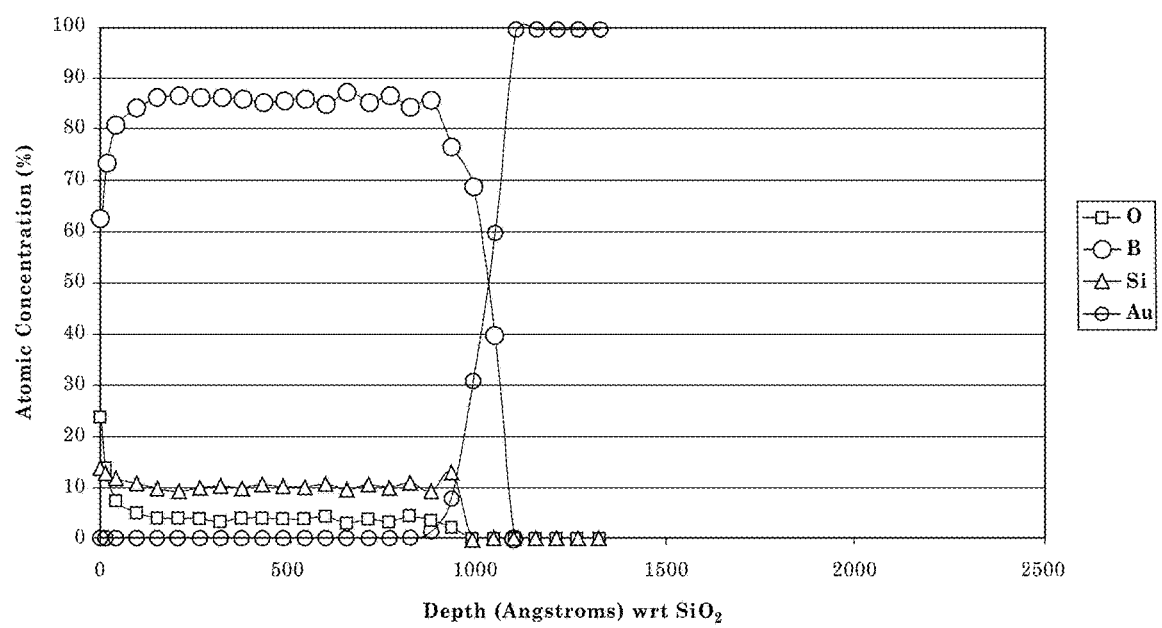
FIG. 81 is an x-ray photoelectron spectroscopy (XPS) depth profile of the oxysilaborane film as deposited in Example 14.

Referring to FIG. 80, a silicon dioxide film 602 was deposited over a gallium arsenide substrate 601. A titanium film 603 and a gold film 604 were evaporated over the silicon dioxide film 602. The substrate 601 was loaded onto a resistively-heated susceptor in a D-125 MOCVD chamber. The chamber was then mechanically pumped below 50 mtorr, whereupon a 3% mixture by volume of diborane in hydrogen $B_2H_6(3\%)/H_2(97\%)$ at the flow rate of 360 sccm and a 2% mixture by volume of monosilane in hydrogen $SiH_4(2\%)/H_2(98\%)$ at the flow rate of 1300 sccm were introduced into the chamber. At the same time, undiluted nitrous oxide $N_2O$ was introduced at the flow rate of 150 sccm. The gases were permitted to mix and to stabilize before entering the deposition chamber of the MOCVD reactor. Upon stabilization of the reactant gas flow rate, the chamber pressure was regulated at 20 torr and the molybdenum susceptor was rotated at 1100 rpm. The substrate temperature was increased to 240° C. by the resistively-heated rotating susceptor. After stabilizing at the deposition temperature of 240° C., the chemical reaction was allowed to proceed for 20 minutes, whereupon the susceptor heating was halted and the sample was permitted to cool to below 80° C. prior to removing it from the deposition chamber. An oxysilaborane film 605 was deposited over the gold film 604, as shown in FIG. 80. The film thickness was measured by variable-angle spectroscopic ellipsometry to be 91.8 nm. The XPS depth profile in FIG. 81 established that the respective relative atomic concentrations of boron, silicon and oxygen in the oxysilaborane film 605 are: 85.2%, 10.0%, and 3.8%.

Figure 82:
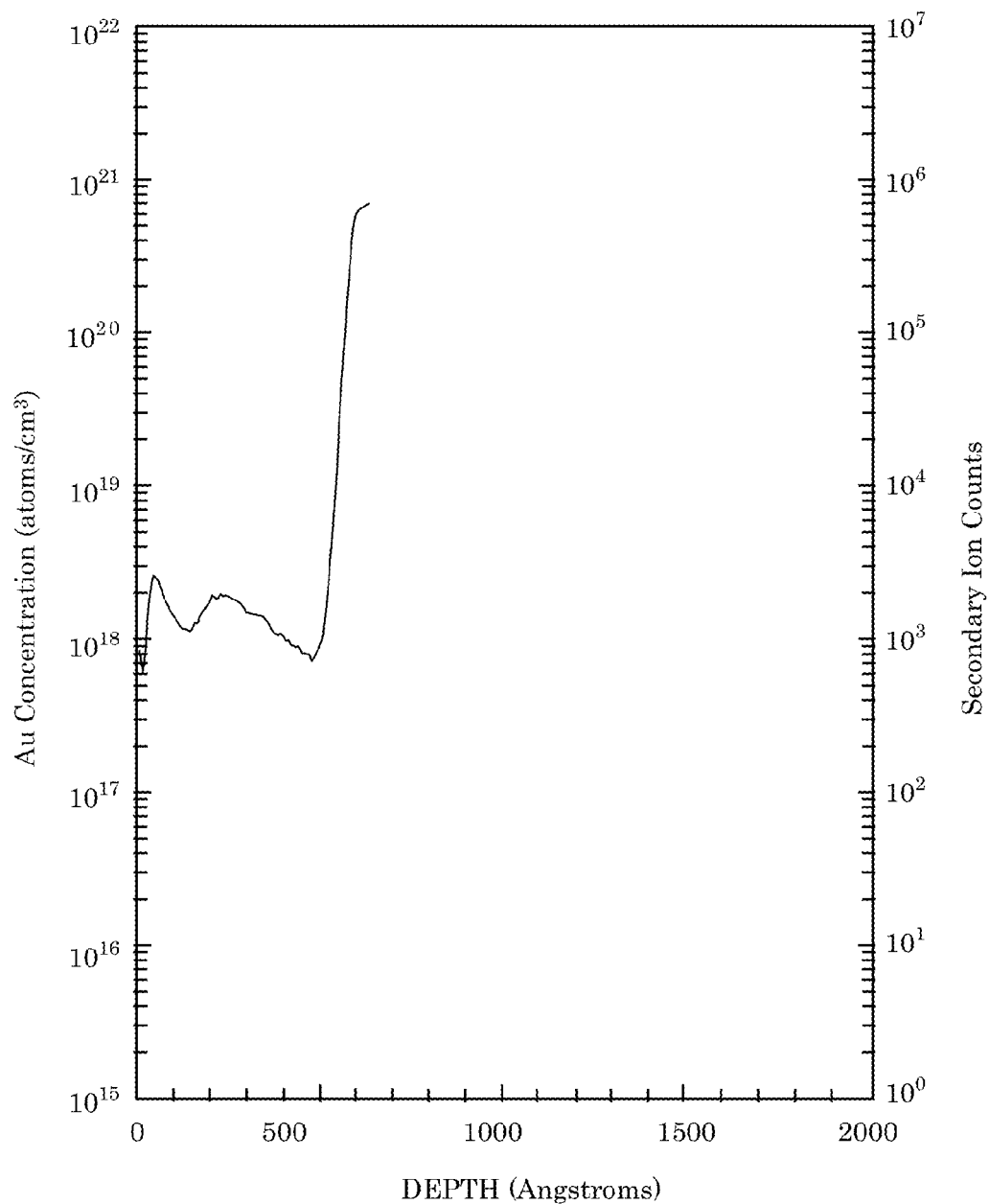
FIG. 82 is a secondary ion mass spectroscopy (SIMS) performed to measure a trace impurity concentration of gold in the oxysilaborane film 605 of Example 14.
Figure 83:
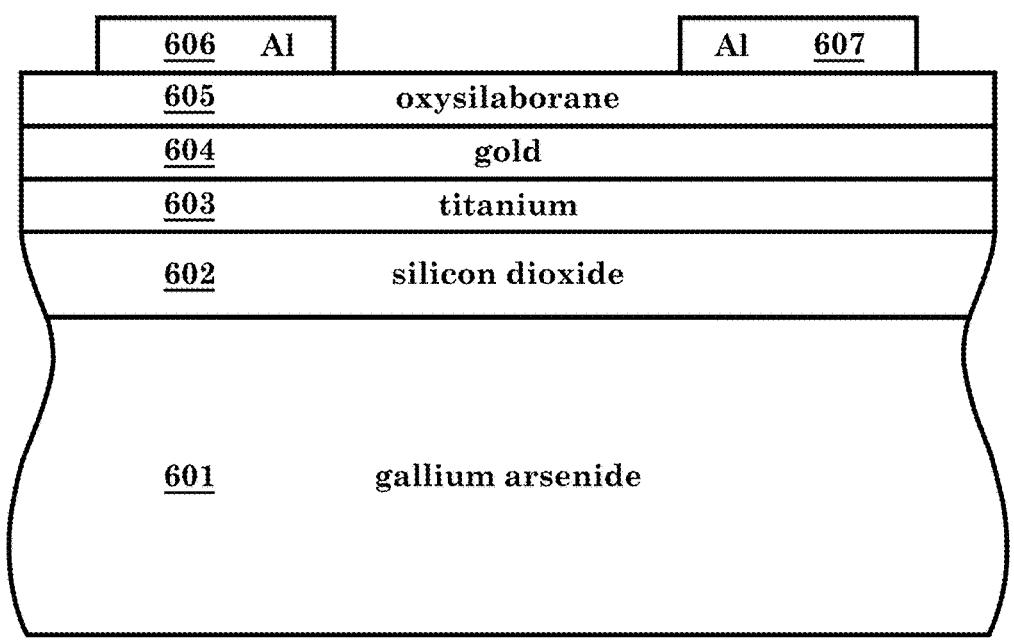
FIG. 83 depicts metal electrodes 606 and 607 evaporated over the gold film containing device of Example 14.
Figure 84:
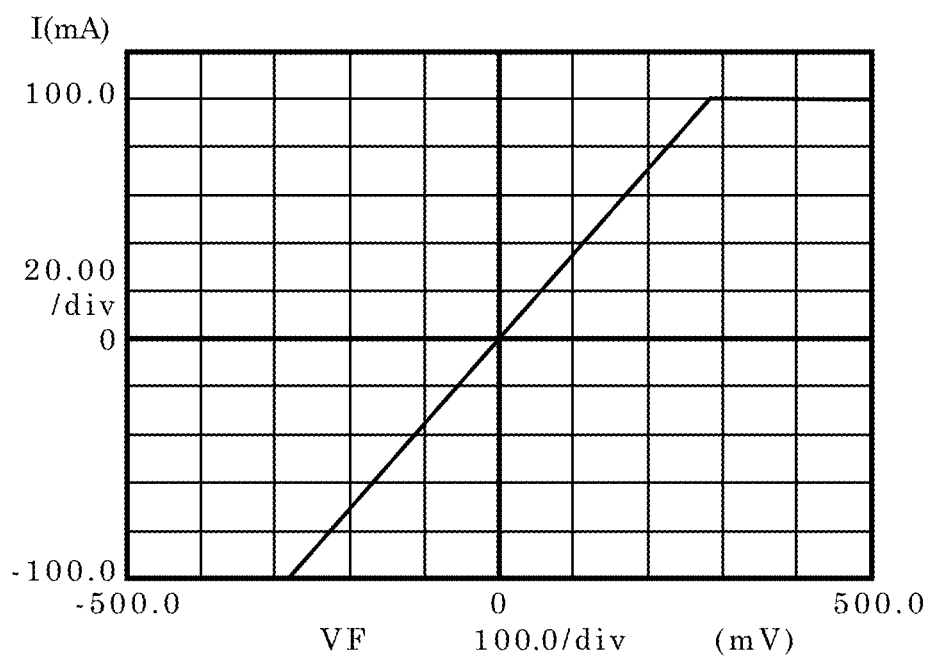
FIG. 84 is a graph of the current-voltage characteristics of the oxysilaborane film 605 of Example 14.

A secondary ion mass spectroscopy (SIMS) was then performed in order to measure a trace impurity concentration of gold in the oxysilaborane film 605. The SIMS depth profile in FIG. 82 measured the gold atomic concentration as being $\sim 10^{18}$ cm$^{-3}$. An RBS and HFS analysis measured the relative atomic concentrations of boron, hydrogen, silicon, and oxygen as being: 70%, 17%, 10%, and 3%. Metal electrodes 606 and 607 were evaporated over the gold film, per FIG. 83, by evaporating aluminum through a shadow mask in a bell jar evaporator. The current-voltage characteristic of the oxysilaborane film 605 was established by an HP-4145 parameter analyzer, with the sweep signals obtained by two microprobes positioned on the metal electrodes 606 and 607. The graph of the current-voltage characteristics of the oxysilaborane film 605 is shown in FIG. 84. The current-voltage characteristics of the oxysilaborane film 605 exhibit an ohmic conduction current, with a 2.9Ω resistance due to the microprobe measurement apparatus. The incorporation of gold as a trace impurity alters the electrical properties of the oxysilaborane film 605 by eliminating space-charge effects. The incorporation of trace gold impurities within oxysilaborane can be achieved by including a gold precursor in the formation gas resulting in the deposition of an oxysilaborane film. Suitable gold precursors are volatile organometallic dimethyl gold (III) complexes, with dimethyl gold (III) acetate $(CH_3)_2Au(OAc)$ being a preferred such gold precursor. The gold precursor can be introduced into the formation gas of oxysilaborane films by a hydrogen carrier gas in an MOCVD reactor. By incorporating trace gold impurities, the electrical conductance of picocrystalline oxysilaborane is substantially increased in a controlled manner.

Thus, one skilled in the art will recognize that layers of picocrystalline oxysilaboranes having varying amounts of oxygen and impurities such as gold can be deposited, for example by chemical vapor deposition techniques, so as to create electronic properties on a tailor-made basis by an atomic engineering of picocrystalline artificial borane atoms 101. All devices, variations and adaptations for using the novel compositions of matter disclosed herein are intended to fall within the scope of the appended claims.

What is claimed is:

1. A solid compound consisting essentially of the chemical elements of boron, silicon, hydrogen and optionally oxygen wherein boron is present in a higher atomic concentration than the other elements.

2. The compound of claim 1 having stoichiometric composition of: $(B_{12}H_w)_xSi_yO_z$ wherein $0 \leq w \leq 5$, $2 \leq x \leq 4$, $2 \leq y \leq 5$ and $0 \leq z \leq 3$.

3. The compound of claim 2 wherein w=4, x=3, y=5 and z=0.

4. The compound of claim 2 wherein w=4, x=2, y=4 and z=2.

5. The compound of claim 1 and further comprising a trace significant impurity of a coinage metal.

6. The compound of claim 1 and further comprising a trace significant impurity of gold.

7. The compound of any one of claims 1-6 wherein the atomic concentration of boron is from about 63% to about 89%.

8. The compound of claim 1 wherein oxygen is present.

9. The compound of claim 8 having stoichiometric composition of: $(B_{12}H_w)_xSi_yO_z$ wherein, $0 < w \leq 5$, $2 \leq x \leq 4$, $2 \leq y \leq 5$ and $0 < z \leq 3$.

10. The compound of claim 9 wherein w=4, x=2, y=4 and z=2.

11. The compound of claim 9 and further comprising a trace significant impurity of a coinage metal.

12. The compound of claim 9 and further comprising a trace significant impurity of gold.

13. The compound of any one of claims 8-12 wherein the atomic concentration of boron is from about 63% to about 89%.

14. The compound of claim 1 wherein the atomic concentration of at least boron, silicon and any optional oxygen present is measured by XPS.

15. A solid compound having stoichiometric composition of: $(B_{12}H_w)_xSi_yO_z$ wherein $0 \leq w \leq 5$, $2 \leq x \leq 4$, $2 \leq y \leq 5$ and $0 \leq z \leq 3$.

16. The compound of claim 15 wherein w=4, x=3, y=5 and z=0.

17. The compound of claim 15 wherein w=4, x=2, y=4 and z=2.

18. The compound of claim 15 wherein the atomic concentration of boron is from about 63% to about 89%.

19. A composition of matter wherein the compound of claim 15 is formed on a substrate comprising monocrystalline silicon.

20. A method of making a composition of matter, comprising:
a) providing a substrate in an enclosed chamber;
b) controllably introducing into the chamber a gas mixture comprising hydrogen, boron and silicon;
c) heating the substrate to a temperature in the range of from about 200 to about 350 degrees C. to form a composition on said substrate, said composition having the formula:

$(B_{12}H_w)_xSi_yO_z$, where: $0 \leq w \leq 5$, $2 \leq x \leq 4$, $2 \leq y \leq 5$ and $0 \leq z \leq 3$.

21. The method of claim 20 and further introducing a gas containing gold.

22. The method of claim 20 wherein said substrate is silicon.

23. The method of claim 20 and further comprising the step of minimizing hydration by isolating the enclosed chamber from ambient moisture.

24. The method of claim 22 wherein said composition is formed as an epitaxial layer on said substrate.

25. A solid compound comprising boron as the majority chemical element, hydrogen as a minority chemical element, and having:
a) no sharp x-ray diffraction peak for a diffraction angle 2θ when said compound is subjected to ω-2θ x-ray diffraction, wherein the x-ray angle of incidence ω is maintained at half of the diffraction angle 2θ, which is varied over $7° \leq 2θ \leq 80'$; and
b) one broad x-ray diffraction peak within the range of diffraction angles $32° < 2θ < 36°$ when said compound is subjected to ω-2θ x-ray diffraction, wherein the x-ray angle of incidence w is maintained at half of the diffraction angle 2θ, which is varied over $7° \leq 2θ \leq 80°$;
c) one broad x-ray diffraction peak at a diffraction angle 2θ contained in $12° < 2θ < 16°$ when said compound is subjected to ω-2θ x-ray diffraction, wherein the x-ray angle of incidence w is maintained at half of the diffraction angle 2θ, which is varied over $7° \leq 2θ \leq 80°$; and
d) a sharp x-ray diffraction peak for a fixed x-ray angle of incidence w that corresponds to half of a diffraction angle 2θ in the range $12° < 2θ < 16°$ when said compound is subjected to grazing-incidence x-ray diffraction, wherein the x-ray angle of incidence is fixed at an angle $ω \leq 8°$ and the diffraction angle is varied over the range $7° \leq 2θ \leq 80°$.

26. The compound of claim 25 specifically having stoichiometric composition of $(B_{12}H_w)_xSi_yO_z$ with $0 < w \leq 5$, $2 \leq x \leq 4$, $2 \leq y \leq 5$ and $0 \leq z \leq 3$.

27. The compound of claim 25 wherein an isotopic enrichment exists such that the ratio of boron $^{11}_5B$ to boron $^{10}_5B$ is lower than the naturally-occurring ratio.

* * * * *